US012702342B2

(12) United States Patent
Nguyen et al.

(10) Patent No.: US 12,702,342 B2
(45) Date of Patent: Aug. 11, 2026

(54) SINGLE ARM ECG MONITOR

(71) Applicant: HELPWEAR INC., Toronto (CA)

(72) Inventors: Frank Nguyen, Toronto (CA); Andre David Thomas Bertram, Toronto (CA)

(73) Assignee: HELPWEAR INC., Toronto (CA)

( * ) Notice: Subject to any disclaimer, the term of this patent is extended or adjusted under 35 U.S.C. 154(b) by 953 days.

(21) Appl. No.: 17/282,379

(22) PCT Filed: Nov. 5, 2019

(86) PCT No.: PCT/CA2019/051574
§ 371 (c)(1),
(2) Date: Apr. 1, 2021

(87) PCT Pub. No.: WO2020/093153
PCT Pub. Date: May 14, 2020

(65) Prior Publication Data

US 2021/0345932 A1 Nov. 11, 2021

Related U.S. Application Data

(60) Provisional application No. 62/755,758, filed on Nov. 5, 2018.

(51) Int. Cl.
*A61B 5/332* (2021.01)
*A61B 5/00* (2006.01)
(Continued)

(52) U.S. Cl.
CPC ............ *A61B 5/332* (2021.01); *A61B 5/0006* (2013.01); *A61B 5/14542* (2013.01);
(Continued)

(58) Field of Classification Search
CPC ... A61B 5/332; A61B 5/0006; A61B 5/14542; A61B 5/256; A61B 5/277; A61B 5/28; A61B 5/6824; A61B 5/7225
See application file for complete search history.

(56) References Cited

U.S. PATENT DOCUMENTS 11,363,958 B2 6/2022 Nguyen et al.
2010/0298661 A1* 11/2010 McCombie ........ G08B 21/0446 600/587

(Continued)

FOREIGN PATENT DOCUMENTS

CA 3021919 A1 9/2018
CN 102166119 B * 7/2012

(Continued)

OTHER PUBLICATIONS

W. Xia, Y. Zhou, Y. Fang and H. Liu, "ECG-Enhanced Multi-sensor Solution for Wearable Sports Devices," 2018 IEEE International Conference on Systems, Man, and Cybernetics (SMC), Miyazaki, Japan, 2018, pp. 1939-1944, doi: 10.1109/SMC.2018.00335. keywords: {Electrocardiography;Electromyography; (Year: 2018).*

(Continued)

*Primary Examiner* — Amanda L Steinberg
*Assistant Examiner* — Laura Hodge
(74) *Attorney, Agent, or Firm* — Fredrikson & Byon, P.A.

(57) ABSTRACT

A system for measuring the ECG of a user by having at least two sensors, all of which are attached to only one peripheral of the user. The system may also comprise a controller for determining ECG signals from the data received from the sensors. The system may be in the form of a wearable band on which the sensors and the controller are disposed. The sensors may be capacitive sensors, electrically coupled capacitive sensors, or electrodes. The sensors may be attached to one arm of a user. The sensors may be disposed on the inside and outside of the arm away from each other at the same axial position on the arm. The sensors may be disposed at axially different positions on the arm, for example, one at the wrist and the other at the shoulder of the user.

16 Claims, 51 Drawing Sheets

(51) Int. Cl.

| | |
|---|---|
| ***A61B 5/145*** | (2006.01) |
| ***A61B 5/256*** | (2021.01) |
| ***A61B 5/277*** | (2021.01) |
| ***A61B 5/28*** | (2021.01) |
| ***A61B 5/349*** | (2021.01) |

(52) U.S. Cl.

CPC .............. *A61B 5/256* (2021.01); *A61B 5/277* (2021.01); *A61B 5/28* (2021.01); *A61B 5/349* (2021.01); *A61B 5/6824* (2013.01); *A61B 5/7225* (2013.01); *A61B 2562/0214* (2013.01)

(56) References Cited

U.S. PATENT DOCUMENTS

| | | | | |
|---|---|---|---|---|
| 2012/0022385 | A1* | 1/2012 | Shimuta | A61B 5/308 600/509 |
| 2012/0035435 | A1 | 2/2012 | Choi et al. | |
| 2014/0100432 | A1 | 4/2014 | Golda et al. | |
| 2014/0213882 | A1* | 7/2014 | Chung | A61B 5/0006 600/372 |
| 2015/0038808 | A1* | 2/2015 | Shimuta | A61B 5/333 600/509 |
| 2017/0055869 | A1 | 3/2017 | Shin et al. | |
| 2018/0301224 | A1* | 10/2018 | Matichuk | G06K 19/07762 |
| 2021/0128001 | A1 | 5/2021 | Claytor | |
| 2021/0345932 | A1 | 11/2021 | Nguyen et al. | |

FOREIGN PATENT DOCUMENTS

| | | | | | |
|---|---|---|---|---|---|
| CN | 109044330 | A | * | 12/2018 | |
| CN | 110115576 | A | * | 8/2019 | A61B 5/0205 |
| JP | 2011156194 | A | * | 8/2011 | |
| KR | 20190034011 | A | * | 4/2019 | |
| WO | WO-2018129718 | A1 | * | 7/2018 | |
| WO | 2018170607 | A1 | | 9/2018 | |
| WO | 2020093153 | A1 | | 5/2020 | |

OTHER PUBLICATIONS

Zhang, Q., Zhou, D. & Zeng, X. Highly wearable cuff-less blood pressure and heart rate monitoring with single-arm electrocardiogram and photoplethysmogram signals. BioMed Eng OnLine 16, 23 (2017). https://doi.org/10.1186/s12938-017-0317-z (Year: 2017).*

International Search Report and Written Opinion issued in corresponding PCT/CA2019/051574 Feb. 5, 2020.

Hannula, M. et al.; "Development and Evaluation of One Arm Electrode Based ECF Measurement System" NBC 2008, Proceedings 20, pp. 234-237 2008.

* cited by examiner

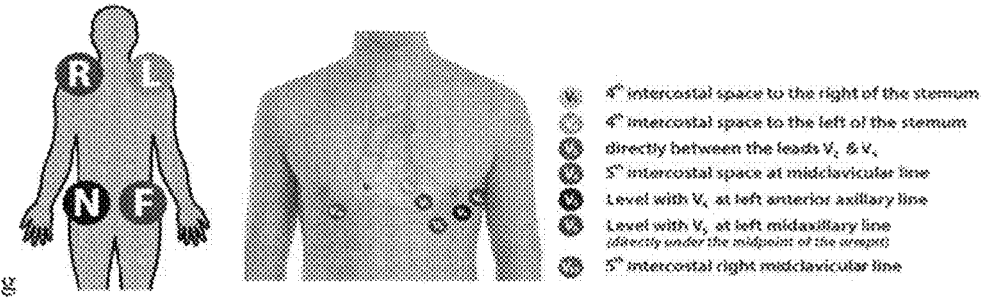
FIG. 1
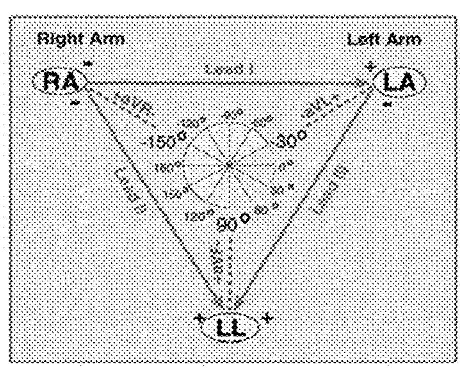
FIG. 2
| De/Re Polarisation | Direction relative to the electrode | Deflection |
|---|---|---|
| Depolarisation | Towards | ⋀ |
| Depolarisation | Away | ⋁ |
| Repolarisation | Towards | ⋁ |
| Repolarisation | Away | ⋀ |
FIG. 3

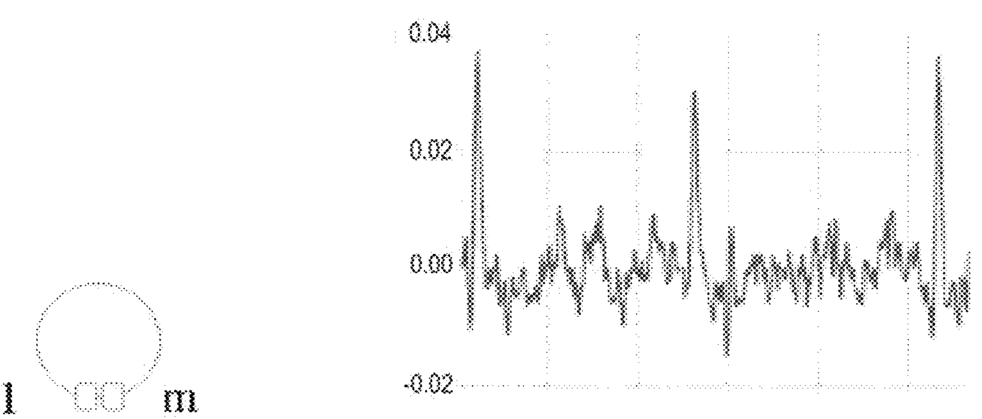
FIG. 43K
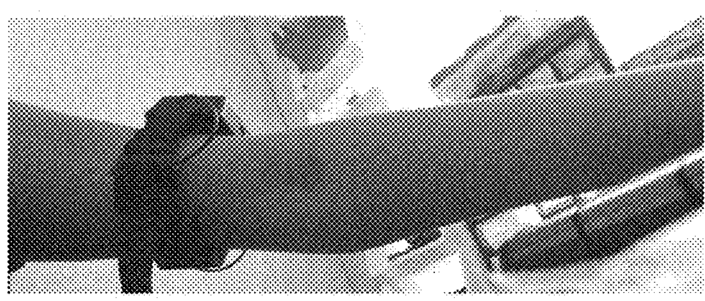
FIG. 44A
0.015
0.010
0.005
0.00
-0.005
l
m
FIG. 44B

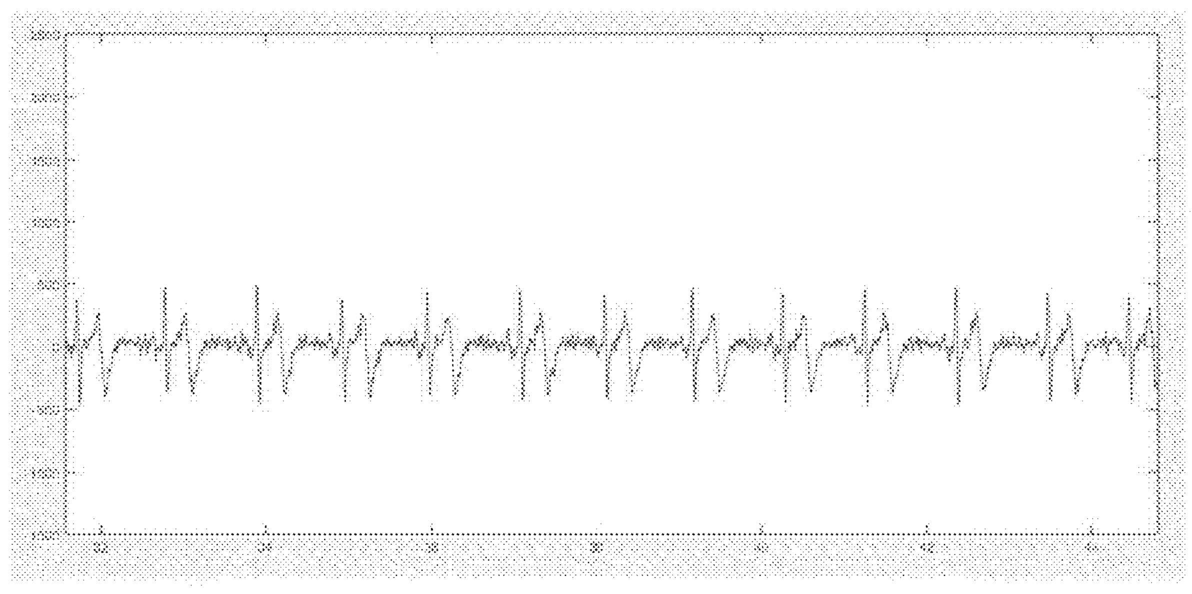
FIG. 55A
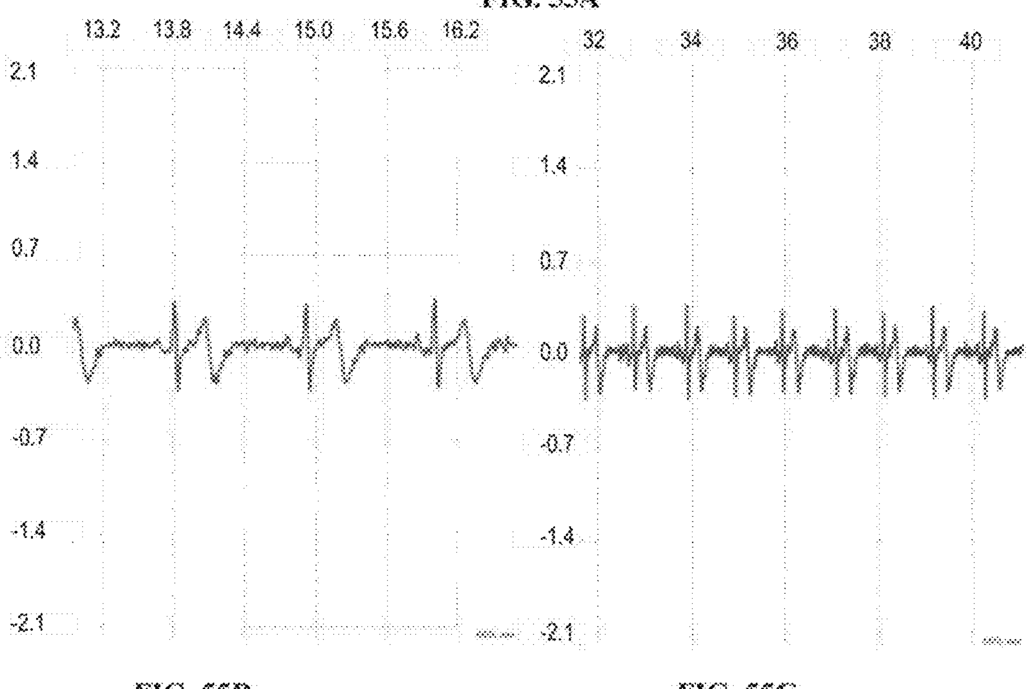
FIG. 55B
FIG. 55C

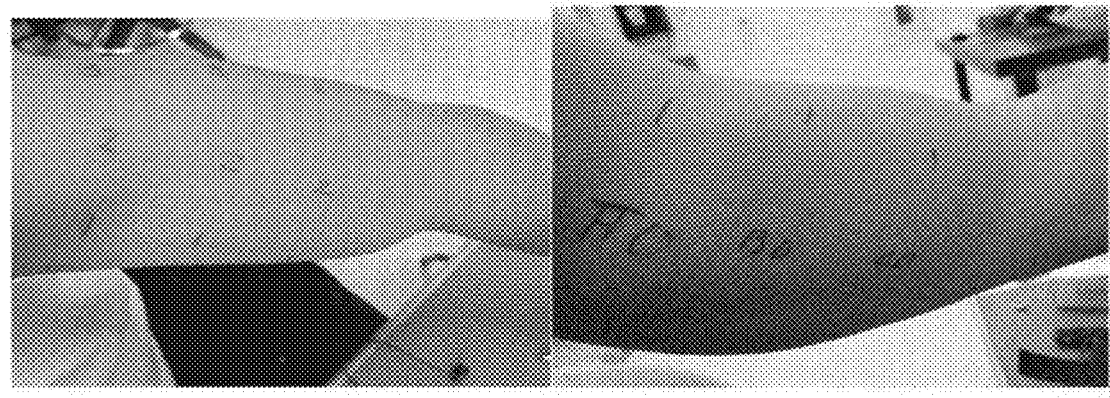
FIG. 57A
FIG. 57B
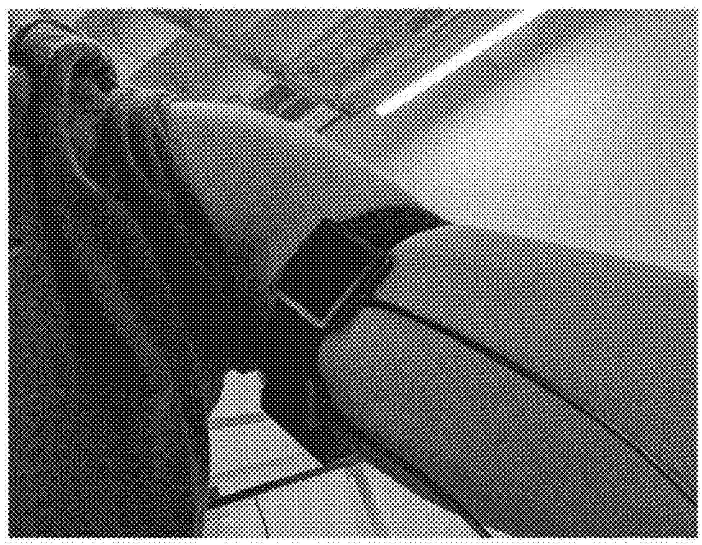
FIG. 58
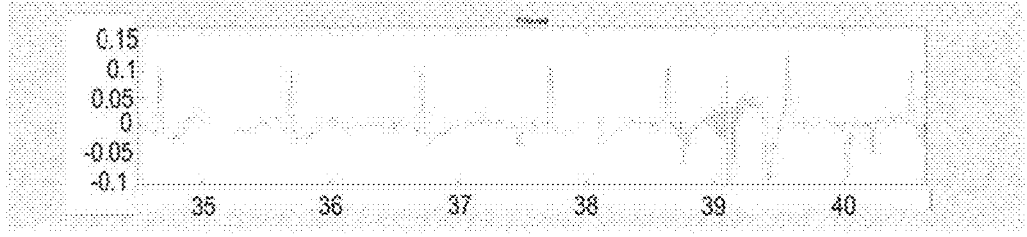
FIG. 59
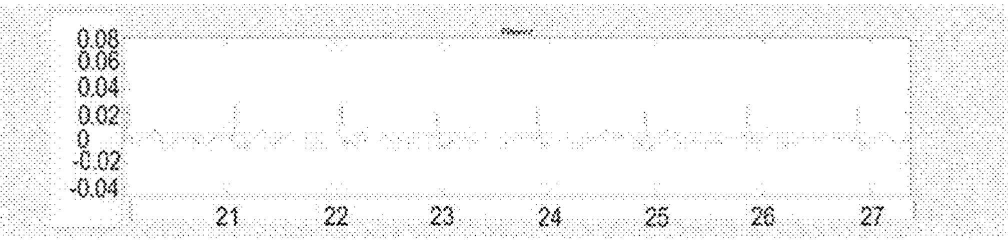

FIG. 60
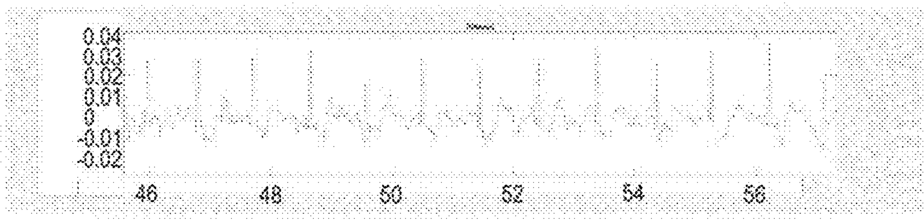
FIG. 61
FIG. 62
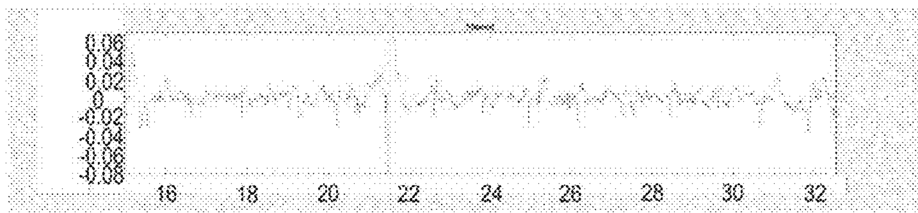
FIG. 63
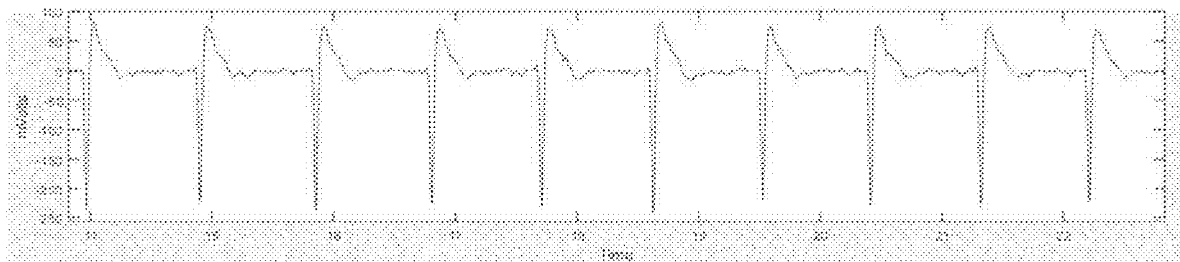
FIG. 64A
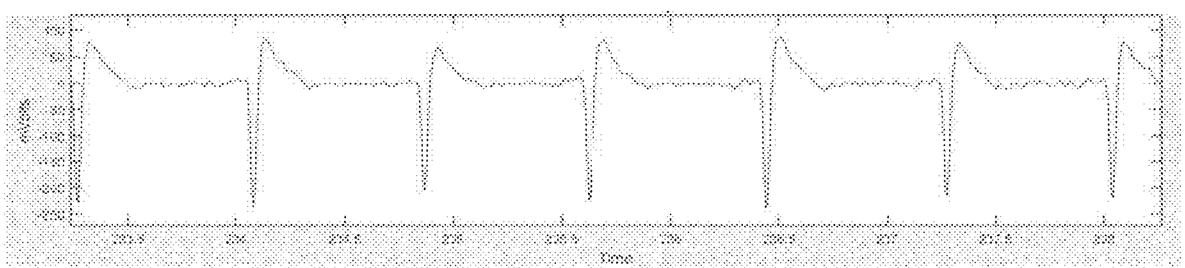
FIG. 64B

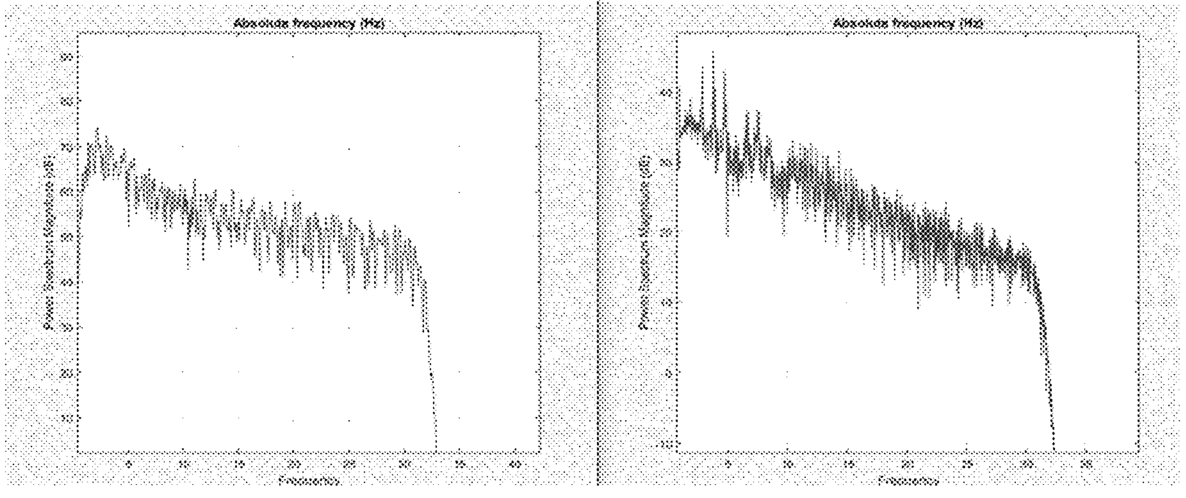
FIG. 69
FIG. 70A
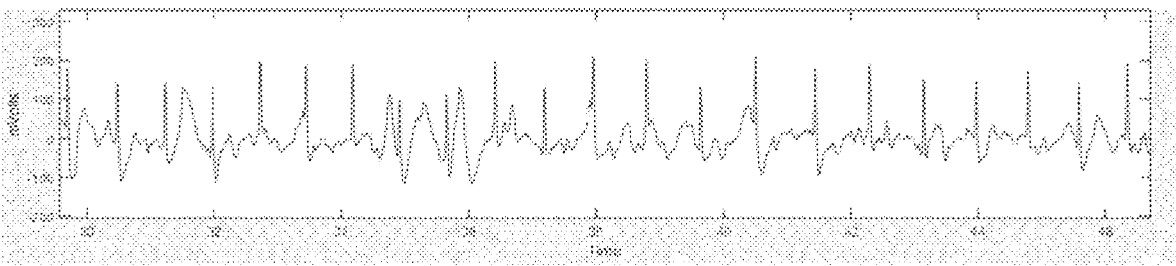
FIG. 70B

SINGLE ARM ECG MONITOR

CROSS-REFERENCE TO RELATED APPLICATION

This application is a U.S. nationalization under 35 U.S.C. § 371 of International Application No. PCT/CA2019/051574 filed Dec. 5, 2018, which claims the benefit of priority to U.S. provisional application Ser. No. 62/755,758 entitled "SINGLE ARM ECG MONITOR" filed Nov. 5, 2018, the entire contents of which are incorporated herein by reference.

TECHNICAL FIELD

This disclosure relates to the field of related to medical devices, in particular electrocardiogram (ECG) monitoring.

BACKGROUND

Current at-home ECG monitors are not cost effective and cumbersome for patients to wear while carrying out their daily lives. These data-centric devices neglect the need for a comfortable, easy to use, and highly clinic independent/at home centered system for a 24/7 at-home ECG monitor.

One difficulty for the patients using current ECG monitors is that the devices are tedious to put on and take off—patients typically do not have a firm enough understanding of the device to put it on themselves. This requires a trained clinician to put the device on the patient correctly (which in some cases results in patients having to drive back/forth to their clinic). This could be especially tolling on patients who live in remote places who must travel long distances to meet with their cardiologists. For example, a conventional heart-monitoring device is a Holter™ Monitor, which functions by placing electrodes at multiple conventional monitoring locations including, but not limited to, the chest of the patient. While this arrangement works for Holter Monitors, there is an unaddressed issue in that these electrodes and wires can fall out of place during the remote monitoring period. If that happens, it is difficult for the patients to put the device back on themselves. As a result, the patient may need to set up an appointment with their cardiac clinic just to put the Holter Monitor back on.

Another difficulty for patients with current ECG monitors includes patients' daily activities being restricted since they are not allowed to shower while wearing the device, and the need for multiple electrodes/wires placed around the patient torso is restricting to a patient's movements while at work or home.

Another difficulty for patients with current ECG monitors is that the current appearance of a Holter monitor can stigmatize patients, as they feel uncomfortable wearing or being seen wearing these devices by others.

Another difficulty is that current ECG monitors may not provide immediate review of a user's data thus restricting the physician's ability to provide real time care and preventing the patient from being involved in personally monitoring their health.

Another difficulty is that current ECGs are not cost effective, as just one patient using a single device would have to bear the costs including cost of the actual device, cost for using the software as a service (SaaS) including the time to analyze the data from the software, and time of the nurse/clinician to constants put on the device onto a patient each time.

Although there are some previous attempts at single-lead ECG devices, they require a sensor contacting the wrist of a user and another sensor contacting the other hand of the user at the same time to function. As such, it is not convenience to use such devices to monitor the ECG of the user continuously. Rather, such devices are often designed for intermittent use such as one-time security authentication.

SUMMARY

At least some example embodiments include a device that takes advantage of newly miniaturized electrocardiograph on the human peripherals. In some embodiments, the device records Electrocardiograph waveforms digitally for review by physician, with emphasis on critical events. In some embodiments, the device comprises a biometric monitoring system that implements the concepts of cardiovascular monitoring through pulse oximetry and/or electrocardiography (ECG).

In some embodiments, the device is in the form of a wearable band unit single arm unit that brings classical ECG monitoring from a multiple electrode torso device into as few as a single pair of electrodes placed on a patient's arm. The device may be able to detect all features of the ECG waveform that is required for clinical diagnosis, or health assessment including but not limited to the P wave, T wave, QRS wave. In addition, the device may extract critical ECG metrics to assist physicians in accurate clinical diagnostics. In some embodiments, the device is worn on one arm of the user to collect an ECG signal from a set of contacts, for example, electrodes on the device. In some embodiments, the contacts are connected into an analog front end and filtered. In some embodiments, the device transmits the data to a phone and/or wireless base station where data is further processed.

In some embodiments, the devices comprises a sensor, wireless microcontrollers, processing microcontrollers, gain and filter systems, and power regulators. The device is configured to detect ECG signals on a peripheral of a person, for example, on one arm of the person. The detected signal includes all parts of the ECG waveform necessary for clinical diagnosis, or health assessment. In some embodiments, for example, the device is worn on the user's left arm, which extracts an ECG from a set of sensors on the device. In some embodiments, the device may be worn in other parts of a user's body. The contacts, for example, electrodes, are connected into an analog front end of the device and the signal is filtered. The device then transmits data representing the signal to a phone/wireless base station where data is further processed.

In some embodiments, the sensors comprises contacts, capacitive sensors, electrically coupled capacitive sensors, or a combination thereof. In some embodiments, the sensors are disposed in the wearable band and contacts extend therefrom and be in contact with the user such that electrical signals from the user can be collected by the sensors. In some embodiments, the contacts are electrodes. In some embodiments, the contacts are integrated in the sensors and the contacts are in direct contact with the user where the sensors are positioned.

In some embodiments, the device includes an ECG monitoring system that is worn on the body, for example, the arm of the user.

In some embodiments, the device includes a contact system that includes electrodes that are placed on specific locations on the arm to optimize the ECG signals for certain parts of the user's body.

In some embodiments, the device comprises a system that is a wearable unit with wireless communication. In some embodiments, the device can connect to a base station or a phone.

In some embodiments, the device is configured to leverage the entire arm to collect different parts of an ECG signal. In some embodiments, the device is configured to leverage the implementation of dry capacitive sensors.

In some embodiments, the device is configured to obtain all key features of ECG data on a peripheral on the user's body. In some embodiments, the devices utilizes a variety of differential and single ended signals to obtain ECG data. In some embodiments, the device comprises integrated filtering and amplification.

In some embodiments, the device comprises shielding methods for reduction of radio frequency (RF), low frequency environment noise, and movement noise.

In some embodiments, the device is configured to work with other devices or sensors that provide biometrics and sensory data to, for example, to provide enhanced data. In some embodiments, the devices comprise implementation and circuit interfacing such that the device can work with other devices and sensors.

In some embodiments, the device comprises onboard gain changing and signal adjustments. In some embodiments, the device can detect signals when the user is in motion. In some embodiments, the device comprises a programmable gain control system.

Example embodiments relate to particular the locations of the wearable band unit on the arm of the user.

The device may provide the following aspects: 1) the device only requires one body part of the user, for example, one arm; 2) Less cumbersome to wear; 3) More flexibility for the user and restricts much less of a patient's daily activities, 4) Collect ECG resemblant data; 5) Easy to take on and off; 6) Does not require wet electrodes; 7) Works well when still; 8) Has a small form factor to reduce the stigma currently experienced by Holter users; 9) Provides real time results and notifies users of poor data which can be amended immediately; 10) Can be worn 24/7 over extend periods of time (longer than the Holter monitor standards of 48 to 72 hours).

An example embodiment is an electrocardiogram (ECG) system for detecting ECG signals from a user. The ECG system includes at least two contacts for disposition on only one peripheral of the user; at least two sensors for detecting electrical signals from the at least two contacts when disposed on the only one peripheral of the user; and at least one controller for determining an ECG signals from the electrical signals.

In an example embodiment, no sensors are collecting the electrical signals from any other parts of the user for the determining of the ECG signal.

In an example embodiment, each of the at least two sensors comprises a dry capacitive electrode sensor.

In an example embodiment, each of the at least two sensors comprises an electrically coupled capacitive sensor.

In an example embodiment, the only one peripheral of the user is an arm of the user.

In an example embodiment, the arm of the user is a left arm of the user.

In an example embodiment, the at least one controller determines a differential between at least two of the sensors for the determining of the ECG signal from the electrical signals.

In an example embodiment, the at least one controller includes a differential amplifier for the determining the differential.

In an example embodiment, the ECG system includes a wireless communication module for transmitting information including the electrical signals.

In an example embodiment, the at least one controller is configured to wirelessly receive the information and determining the ECG signals from the information.

In an example embodiment, the at least one controller comprises an application for determining the ECG signals from the information.

In an example embodiment, the ECG system includes a wearable band on which the at least two sensors are disposed, the wearable band being wearable on only the one peripheral of the user.

In an example embodiment, the ECG system includes a filter, shielding, and/or amplifier that is disposed in the wearable band.

In an example embodiment, the ECG system includes one or more sensors that are disposed in the wearable band for determining pulse oximetry or biometrics other than the ECG signal.

In an example embodiment, the contacts are positioned on a same axial length along the one peripheral of the user and the positions have different radial positions on the same axial length.

In an example embodiment, the positions are from mid bicep to an armpit of the user.

In an example embodiment, the positions are at the shoulder of the user.

In an example embodiment, the radial positions are radially opposite to each other with respect to the peripheral of the user.

In an example embodiment, the radial positions at about 90° to each other relative to the axis of the peripheral of the user.

In an example embodiment, the contacts are on different axial positions along the one peripheral of the user, wherein at least two of the sensors are configured to detect the electrical signals on the different axial positions.

In an example embodiment, the peripheral is an arm, one of the at least two contacts is positioned at the wrist of the arm and another one of the at least two contacts is positioned at a shoulder of the arm.

In an example embodiment, the peripheral is an arm, one of the at least two sensors is positioned at the wrist of the arm and another one of the at least two contacts is positioned at around a middle of a forearm of the arm.

In an example embodiment, the ECG system further includes a re-programmable gain control system interposed between the at least two sensors and the at least one controller.

In an example embodiment, the at least two sensors are in an open circuit configuration with respect to remaining parts of the user other than the only one peripheral. Grounding leads or plates are not required in some example embodiments.

Example embodiments also include a use of the system for detecting ECG signals of the user.

Another example embodiment is a method for ECG monitoring of a user. The method comprises detecting electrical signals from one peripheral of the user using at least two sensors, and determining an ECG signal from the electrical signals detected by the at least two sensors. In some embodiments, the determining includes determining a differential between the electrical signals detected by one of the at least two sensors and the electrical signals detected by another one of the at least two sensors. In some embodiments, the at least two sensors are in an open circuit configuration with respect to parts of user other than the only one peripheral.

BRIEF DESCRIPTION OF THE DRAWINGS

Reference will now be made, by way of example, to the accompanying drawings which show example embodiments, and in which:

FIG. 1 shows the conventional Standard ECG electrode placement from a 12 Lead device.

FIG. 2 shows the algorithm to calculate the main ECG leads.

FIG. 3 shows the deflections of the ECG signals.

FIGS. 43B-43K show the positions of the sensors and the corresponding signals when the device was attached at the upper part of the upper arm as shown in FIG. 43A, in which 1 means lateral and m means medial.

FIG. 44A shows the device attached at the lower part of the upper arm.

FIGS. 44B-44K show the positions of the sensors and the corresponding signals when the device was attached at the lower part of the upper arm as shown in FIG. 43A, in which 1 means lateral (on the other side of the arm relative to the radial artery), and m means medial (on the side of the arm close to the radial artery).

FIGS. 55A-55C show the results from the wrist using one embodiment of the device of this disclosure comprising capacitive sensors.

FIGS. 57A-57B show the coordination system on a user's arm to identify the area from which results were obtained.

FIG. 58 shows the method of strapping used to hold the electrodes in place.

FIG. 59 shows the result when the one sensor was placed at A0 and another sensor was placed at A3 in the coordination system shown in FIGS. 57A-57B.

FIG. 60 shows the result when one sensor was placed at B0 and another sensor was placed at B1 in the coordination system of FIGS. 57A-57B.

FIG. 61 shows the result when a sensor was placed at B0 and another sensor was placed at B2 in the coordination system of FIGS. 57A-57B.

FIG. 62 shows the result when a sensor was placed at B0 and another sensor was placed at B4 in the coordination system of FIGS. 57A-57B.

FIG. 63 shows the result when a sensor was placed at C0 and another sensor was placed at C4 in the coordination system of FIGS. 57A-57B.

FIG. 64A shows the result when the arms in pockets and at the power station.

FIG. 64B shows the result when the arms in pockets and away from the power station.

FIG. 69 shows another enlarged view of the comparison of the results with and without the RF shield, with the results the left side shows results with the RF shield, while the right side shows results without the RF shield.

FIGS. 70A and 70B show the results using conventional wet electrode and the device of this disclosure when the user is in normal walking motion, respectively.

DETAILED DESCRIPTION OF EXAMPLE EMBODIMENTS

Figure 4:
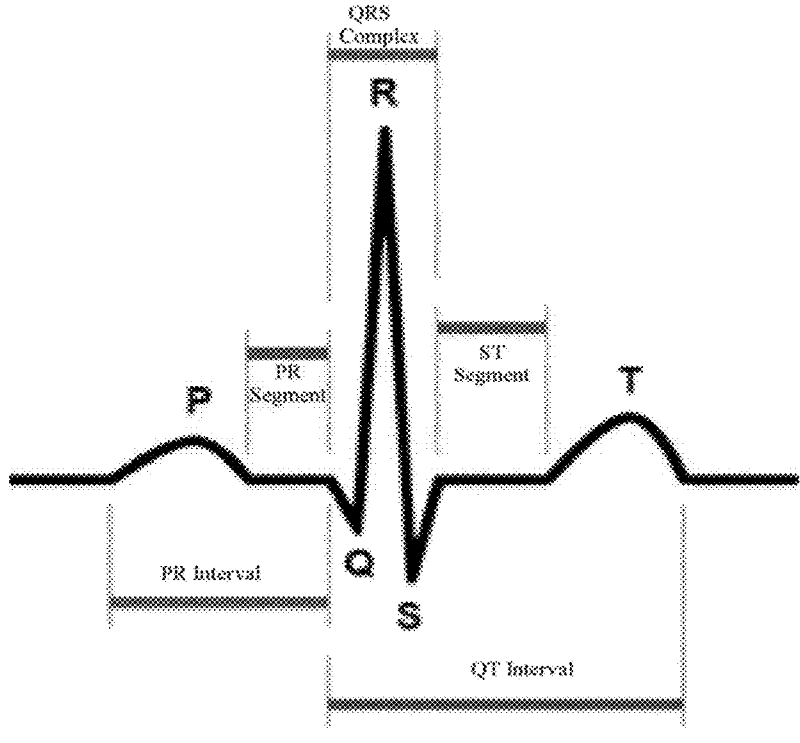
FIG. 4 shows a typical ECG of lead 2 of a healthy user.

The ECG (electrocardiogram) spatially analyzes the electrical signal produced by the heart's muscles. Electrodes are placed in specific locations around the body to gather different projections of these electrical signals. A differential signal between two or three of these signals creates a lead, which provides information about the condition of the heart.

A traditional 10 electrode ECG can produce 12 leads (see FIG. 1). Placements of these electrodes are critical in getting an accurate picture of the heart. The lead is a vector on which the electrical signals are analyzed on, thus electrode place equidistant from the heart and along this vector should produce the same results. The most commonly used leads are Lead 1, 2, 3 and the augmented Vector Right (aVR), augmented Vector Left (aVL), augmented Vector Foot (aVF) created using the Right Arm (RA), Left Arm (LA) and the Left Leg (LL) electrode. The fourth electrode on the Right Leg (RL) is used as a grounding reference electrode. FIG. 1 shows the placement of these electrodes.

Although the device of this disclosure uses an atypical electrode location, the fundamental theory of creating an ECG signal from these electrodes are the same.

Analysis of the collected Data: Each of the electrodes detects electrical potentials created from muscle contractions within the body. To recap muscle anatomy, a muscle, at its resting state, has an electrical potential of −70 mV. When contracting, the muscle's potential increases to +30 mV, this is called depolarisation. In order to contract a second time, the muscle must return to its resting state potential of −70 mV. Before it can do this it reach a −90 my potential to reset itself. This second process is called repolarization. The electrodes detect the depolarisation and repolarisation of muscles active in both the atria and ventricles of the heart. The ECG's signal deflection is either positive or negative depending on whether the heart's muscles are depolarising or repolarizing and the directions towards the electrodes these electrical signal are moving as shown in FIG. 3. Each electrode records these electrical signals over time.

Calculating the ECG Leads: The lead creation of the ECG signals is a differential calculation between two or three of the electrodes. In doing so the two electrodes give a spatial description of the heart's electrical activity along the Lead (a vector line). The 6 main Leads are Lead 1, 2, 3 and aVR, aVL, aVF. The differential equation to calculate these leads are summarized below and is illustrated in FIG. 2:

$$\text{Lead } I=LA-RA$$

$$\text{Lead } II=LL-RA$$

$$\text{Lead } III=LL-LA$$

$$aVR=RA-(LA+LL)/2$$

$$aVL=LA-(LL+RA)/2$$

$$aVF=LL-(LA+RA)/2$$

In the equation, LA, RA, and LL refer to the detected potential at the left arm, right arm, and left leg, respectively.

The device of this disclosure has contacts that are placed in an atypical location, thus producing a unique lead. In some embodiments, the contacts are integrated in the sensors. In some embodiments, the contacts extend away from the sensors. In some embodiments, the contacts are electrodes. However, the device follows the same fundamental method of collecting the user's ECG by detecting the depolarization/repolarization of the heart's muscle contractions along a vector between its two electrodes.

Feature Detection of an ECG: There are a variety of features that can be detected both visually and through digital signal processing, as discussed below. For example, FIG. 4 shows the healthy ECG signal from lead 2.

QRS Complex: This complex is caused due to the contraction of the ventricles. It begins with the depolarization of the interventricular fibers down the heart (the Q wave) thus resulting in a negative deflection. The length of the segment should be less than 0.04 seconds and should not exceed an amplitude of ¼ of the R-wave. The R-wave is depolarization of the remaining of the ventricles. It is positive deflection and is the largest amplitude. This feature is used to determine heart rate. The S wave is due to late depolarisation of the ventricles moving down the heart. It cause a slightly larger negative deflection than the Q wave. The entire QRS complex amplitude ranges from 120 mV and occurs for a duration of 0.08-0.12 seconds.

T Wave: The T wave represent the repolarisation of the ventricles. It has a magnitude of 20-30 mV and should be rounded in shape with a positive deflection.

P Wave: The P wave represents the depolarization of the atria. It results in a positive inflection of 10 mV. As the atria is a smaller muscle the muscle electrical activity is smaller. The P wave precedes the QRS complex and occur for 100-200 msec.

Overall System Design: The system comprises at least two sensors and at least one controller. The sensors collect signal from the user. The controller processes the data from the sensors to determine the ECG signals for the user.

Figure 5A:
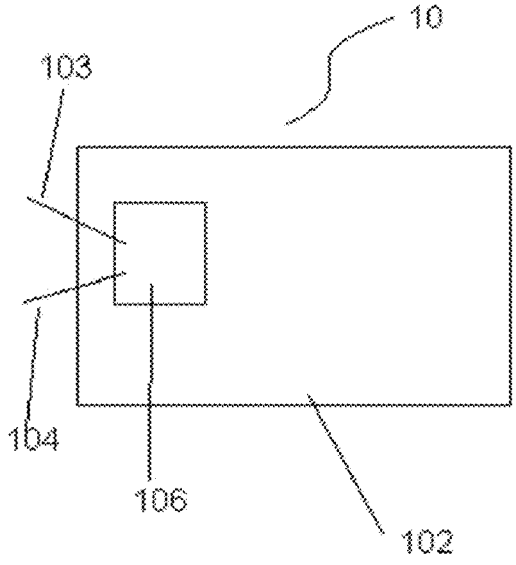

FIG. 5A shows one example configuration of the system. The system 10 comprises a device body 102, a controller 106 is disposed in the device body 102. Two sensors 103 and 104 are connected to the controller 106. In some embodiments, the controller 106 includes signal processing functions, for example, filtering and amplification of the signals collected by the sensors.

Figure 5B:
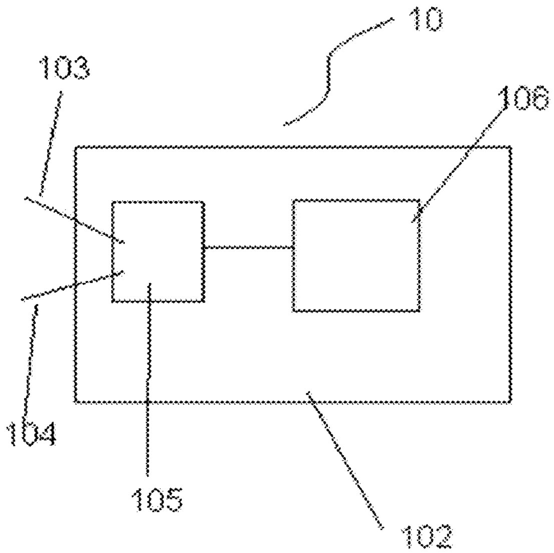

FIG. 5B shows another example configuration of the system. The system 10 comprises an additional signal processing unit 105 disposed between the sensors and the controller 106. For example, the signal processing unit 105 may provide amplification and filtering to the signals collected by the sensors 103 and 104.

Figure 5C:
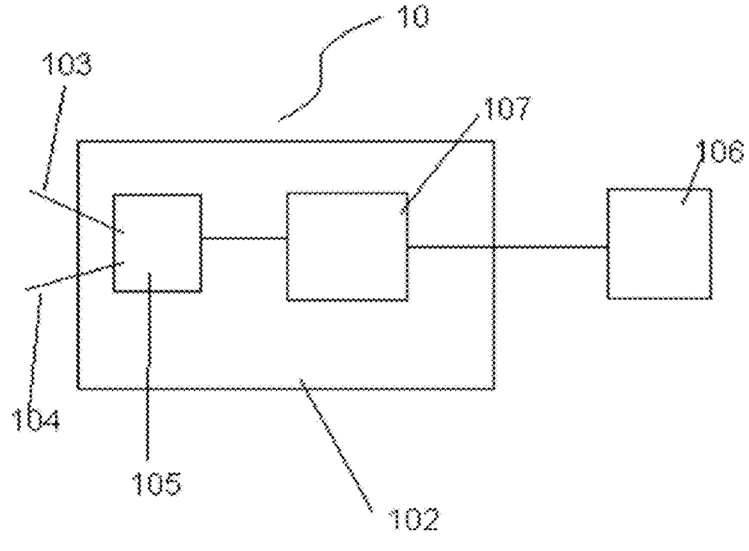

FIG. 5C shows another example configuration of the system. The system 10 comprises an additional transmission module 107. The controller 106 is disposed separately from the device body 102. The transmission module 107 is configured to send information including the signals collected by the sensors 103 and 104 to the controller 106. In some embodiments, the transmission is wired. In some embodiments, the transmission is wireless, for example, through Bluetooth™, WI-FI™, or radio frequency. In some embodiments, the signal-processing unit 105 is incorporated in the controller 106. In some embodiments, the controller 106 comprises a smart phone, for example, an Android™ phone or iPhone™ with applications installed thereon to process the information.

In these example configurations, one sensor 103 may be disposed in the device body 102 and the other sensor 104 may be disposed away from the device body 102.

Figure 6:
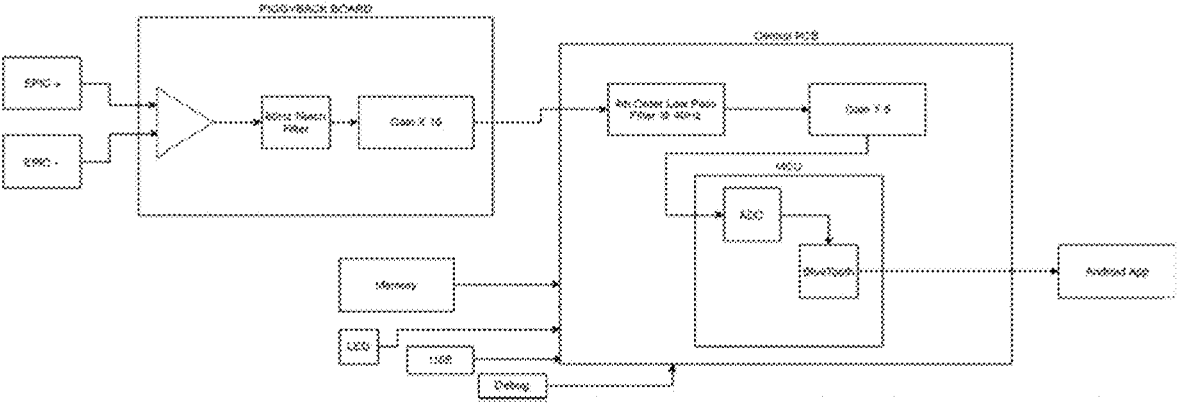
FIG. 6 shows the overall flowchart of one embodiment of the device of this disclosure.

This section explains the overall system design of the device of this disclosure. It will explain the process of how the signal is collected, processed, and presented on an external application, for example, an android application. An example, flow chart of the system is shown in FIG. 6. Further explanation about the system is described in the following sections.

In some embodiments, the device comprises two sensors that collect data from the user. In some embodiments, the data is passed through an amplifier. In some embodiments, the amplifier comprises instrumentation amplifier. In some embodiments, the amplifier is an opamp. In some embodiments, the amplified signals are filtered, for example, by a 60 Hz notch filter. In some embodiments, the filtered signals are amplified, for example, by a fixed ratio gain or a re-programmable gain control that has variable gain. The fixed ratio gain may be 10× gain. In some embodiments, the further amplified signals are filtered again, for example, by a low pass filter. In some examples, the low pass filter is a 4th order low pass filter. In some embodiments, the low pass filter is set at 40 Hz. In some embodiments, the filtered signals are again amplified, for example, by a fixed gain or re-programmable gain. In some examples, the fixed gain is 5× gain. In some embodiments, the amplified signals are digitized by at least one ADC. The digitized signals may be transmitted to a device for display or further processing. For example, the device may be an Android™ device with applications for processing the data received wirelessly, for example, by Bluetooth™ or other wireless means. In some instances, the digitized signals may be transmitted to a display.

Software Overview and Block Diagram: In some embodiments, the software system of the wearable band unit is divided into three section; external application, for example, an Android Application; Signal Processing Software; and Firmware.

External Application: The external application is the interface between the electronics and the user. It collects the signal sent by the device by wire or through wireless means. For example, the transmission of the signal may be through network cable, phone cable, WiFi, or Bluetooth™. The external application then applies additional software filtering and present the information visually to the user. In some embodiments, the external application calculates various metrics to assist patients and physicians in analyzing the data.

Figure 7:
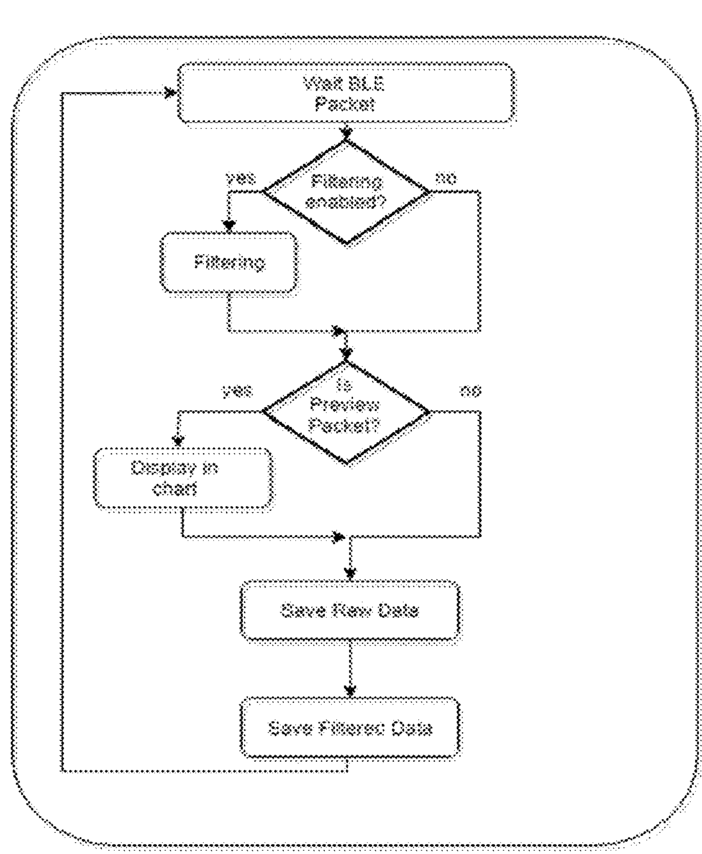
FIG. 7 shows the flow chart of data processing in one embodiment of an Android™ application of the device.

One embodiment of the process flow of the application is shown in FIG. 7. In some embodiments, the external application is an android application. In some embodiments, the device receives signals collected by the sensors through Bluetooth™ low energy (BLE). Depending on the configuration of the application, the signals received may be filtered. The application then determines whether a preview is configured, and provide a preview if it is configured. For example, the data may be displayed in the form of a chart. In any case, the signals received are saved. And filtering is performed in example embodiments, the filtered data may also be saved.

Signal Processing: Additional software signal processing is complete by the external application to improve the signal quality. These include: 1) Baseline drift correction algorithm (to reduce the low frequency noise); 2) A 60/50 Hz Notch filter (to reduce the power line noise); 3) Low pass filter (to reduce the high frequency noise)

Figure 8:
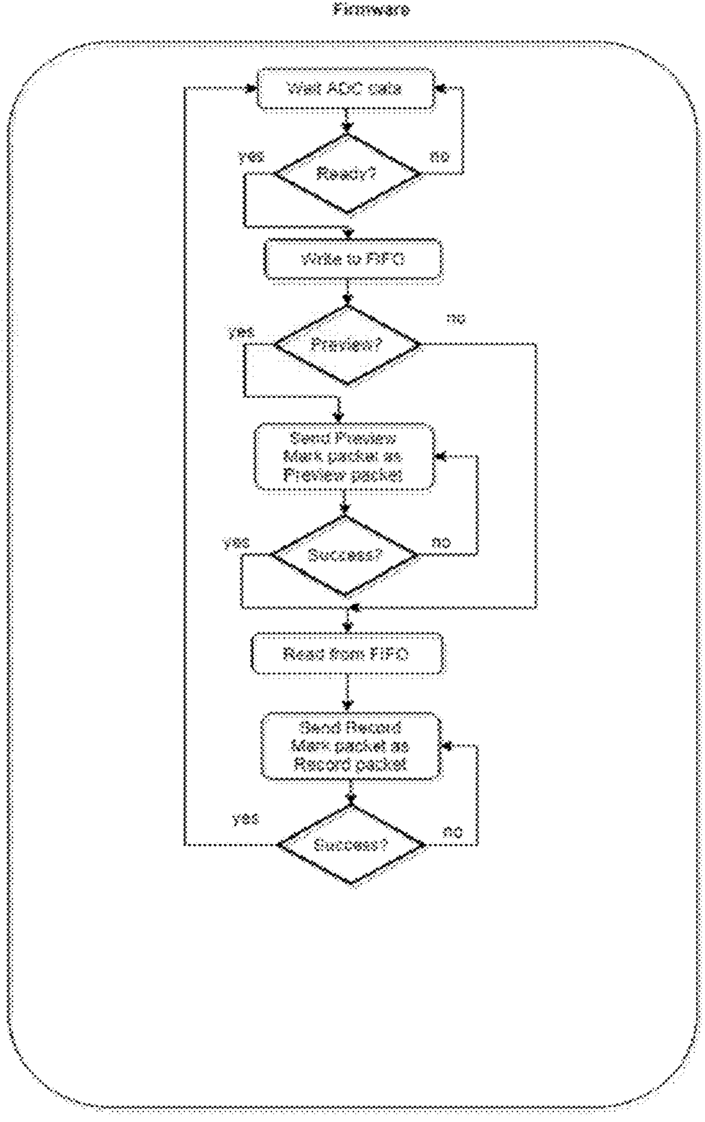
FIG. 8 shows the flow chart for data processing by the firmware.

Firmware: The firmware enables the device's hardware to function. Its application is simply a method data collection, data storage and data transmission. An additional feature includes signal decimation to reduce the data samples. The flow chart of one embodiment of data processing by the firmware is shown in FIG. 8. In some embodiments, the firmware receives digitized data from an analog-to-digital converter (ADC). If the firmware is ready to process the data, the data is written to a memory, for example, a first in, first out (FIFO) type memory. If the firmware is not ready or the data is not suitable, the firmware returns to the standby state waiting for data from the ADC. After the data is written to the FIFO memory, a determination is made regarding whether preview should be provided. Depending on the determination, preview mark packet is sent as preview packet. If the transmission is successfully, data is read from the FIFO memory. If it is determined that preview is not to be provided, the firmware reads data from the FIFO memory. After data is read from the FIFO memory, record mark packet is sent as record packet. If the sending is successful, the firmware returns to the standby state awaiting data from the ADC. Otherwise, the sending is repeated.

Figure 9:
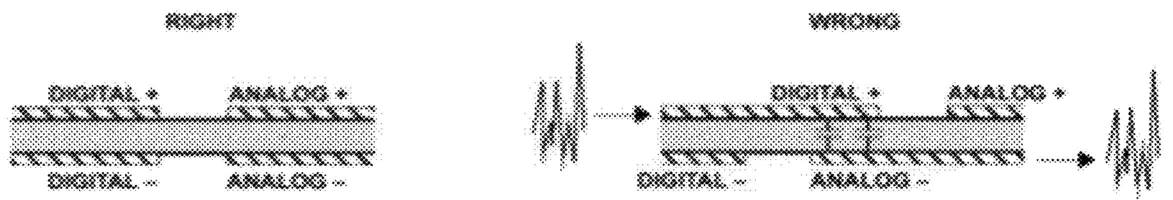
FIG. 9 shows noise reduction by prevention of overlap between different grounds planes.
Figure 10:
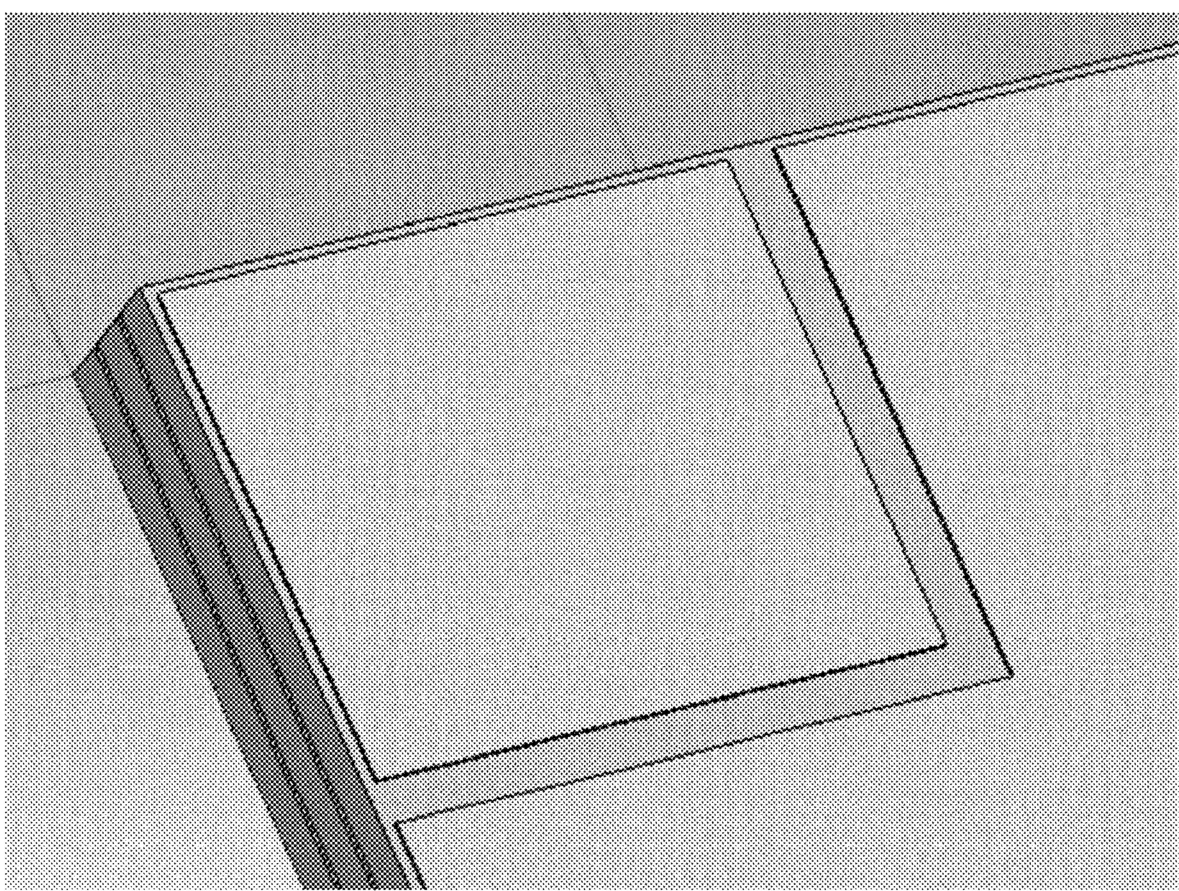
FIG. 10 shows a perspective view of one embodiment of the shielding polygon for the device.
Figure 11:
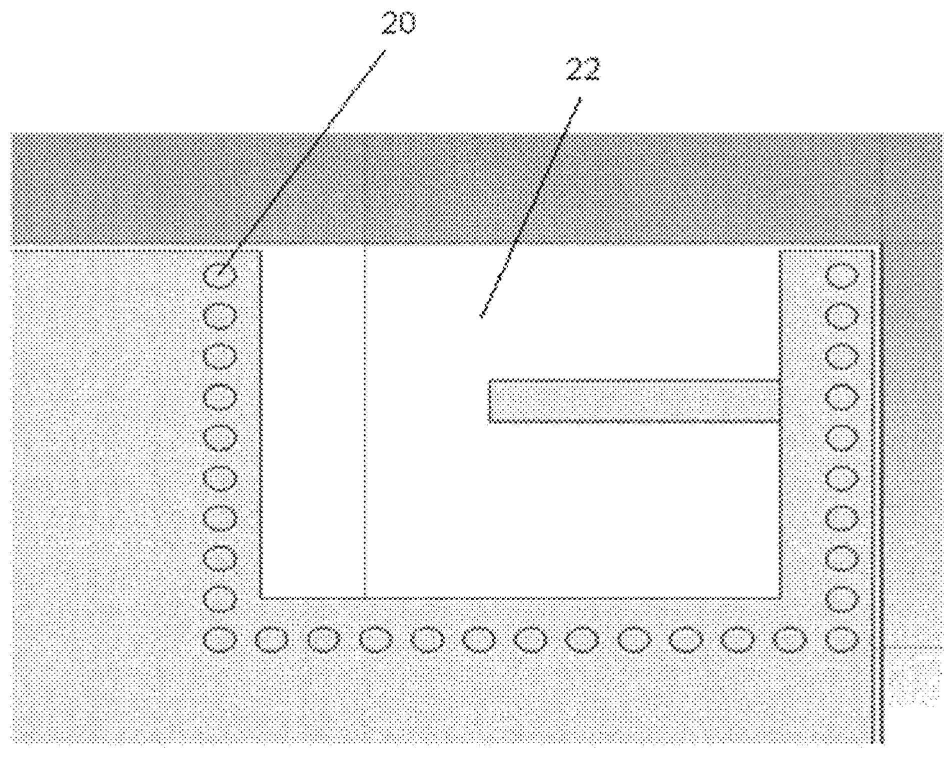
FIG. 11 shows the arrangement of one embodiment of the shielding.

Noise Reduction Methods and Considerations: One method of noise reduction is the prevention of overlap between different grounds planes. One example embodiment is shown in FIG. 9. 1) The board has 3 grounds: signal, digital and analog. No overlap is allowed between different grounds for the methods of this disclosure. 2) No traces are in the gaps between grounds except traces associated with components, located on the border between grounds. 3) All ground borders, as shown in FIG. 9, should be surrounded by vias (with small gap. 4) Analog and power grounds may be surrounded by about polygon with a thickness of about 1 mm for shield covers soldering. It may be mirrored on both top and bottom layers, the shielding covers must be connected with each other by vias with small gaps, for example, about 0.1-1 mm, 0.2-0.9 mm, 0.3-0.8 mm, 0.4-0.8 mm, 0.5 mm, 0.6 mm, or 0.7 mm. The shielding polygons must not be connected to any ground, or having any overlaps with any ground. For example, FIG. 10 shows a perspective view of the shield and FIG. 11 shows a configuration of the shield with vials 20 and shield 22, in which the vials 20 do not overlap the shield 22.

Determine the Signal by the Wearable band unit on a Single Arm: A location of interest for the device is around the wrist of a user. It is found that a periodic signal (roughly 1 Hz in frequency) is produced here, similar to that of an ECG. Although the frequency seem to suggest the signal is ECG, its shape does not follow a common ECG pattern. In fact, the shape of this signal seem to suggest it is a pulse oximeter (PO) signal, which is also typically collected in this area. This section explains a benchmark test to determine whether the signals collected by the device in this location is PO or ECG data.

Figure 12:
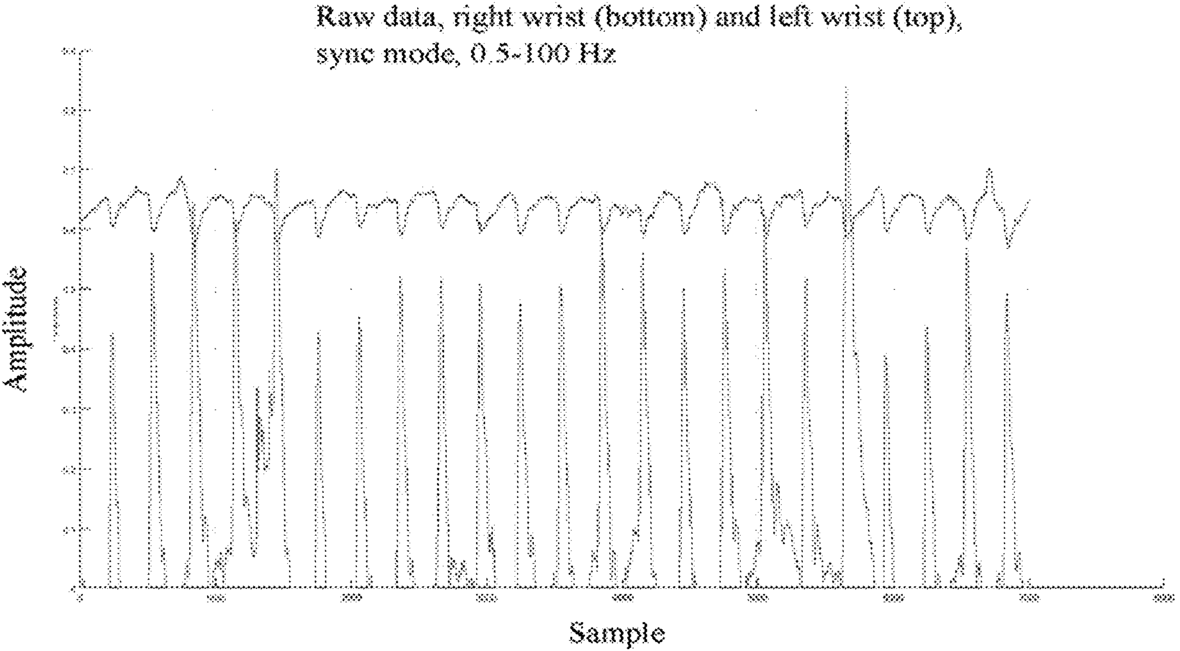
FIG. 12 shows the raw data collected from a single arm from a user using the device of this disclosure.
Figure 13:
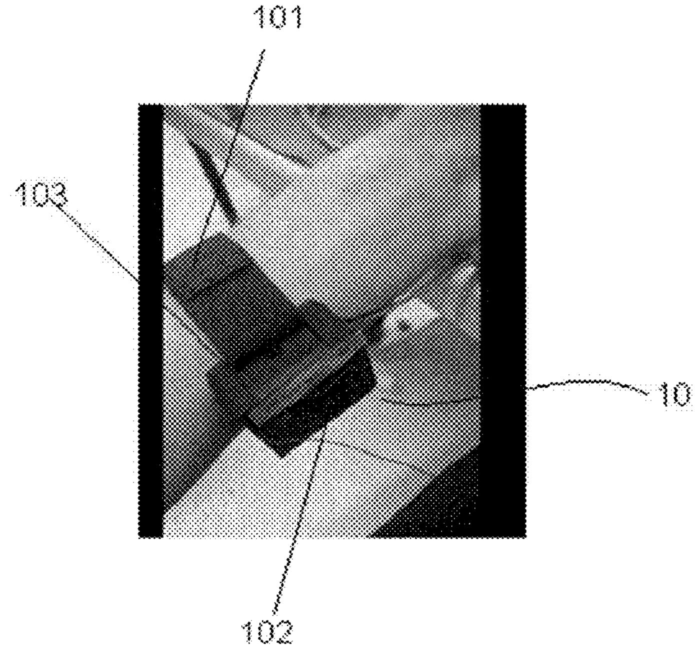
FIG. 13 shows the attachment of the device on the wrist of a user.
Figure 14:
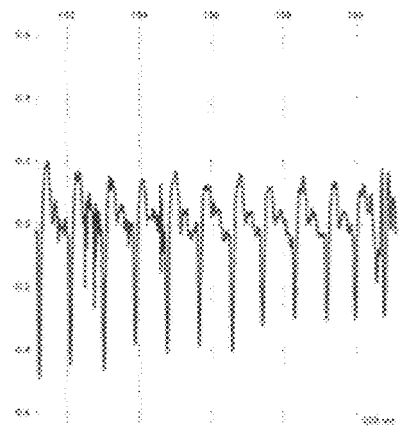
FIG. 14 shows the peaks detected at the wrist.

Wearable band unit Signal: User comfort is a key value attribute of the device. To this end, in some embodiments, the device is a wearable band unit. One pathway to achieve this is collecting a single lead ECG from a location on a single arm. Extensive experimental testing was conducted in developing the device into a configuration to gather a strong ECG signal from one arm. Through the testing a roughly 1 Hz periodic peak was discovered around the wrist of a single arm (FIG. 12, 14) when signals were collected in this area, resembling a heartbeat. In this configuration, the main capacitive sensor 103 of the device 10 was placed on the medial side of the arm (near the radial artery). In some embodiments, the sensor 103 is disposed in the device body 102. In some embodiments, the sensor 103 is configured to collect signals at this position to get a reliable signal. In some embodiments, the second sensing plate was placed opposite to the main sensor 103 with respect to the arm and secured to the arm, for example, by the device's strap 101 (see FIG. 13) such that the sensor 103 collects signals from the position that the sensor 103 is in contact with the user. In some embodiments, an electrode may extend from the sensor, the electrode being in contact with the user such that the sensor 103 collects signals from the user. ECG signals can be constructed without the user having to use their opposite hand to touch the device. As such, the device can be configured to operate on a peripheral of the user, in an open loop or open circuit configuration in relation to parts of the body other than this peripheral, for example, the other peripherals and the chest of the user. The device only requires contact with the single peripheral of the user, and does not require contact with the other peripherals or the chest of the user.

Signal Type ECG: The signal may be ECG for a couple of reasons. The signals seemed to detect peaks that coincide with heartbeats at roughly a 1 Hz frequency. Second, the device had already been proven to be capable of collecting ECG signal between two wrist and around the chest. Although there is little resemblance of the signal to a complete ECG (PQRST trace, for example, as shown in FIG. 4), there was no prior knowledge of what an ECG would look like around a wrist. It is safe to say (as ECG are spatial electrical depictions of the heart) that collecting a signal from two locations down the same arm may look very different from a typical ECG. Additionally, more filtering or amplification may reveal the remaining ECG features. Finally, a physiological phenomenon that a blood vessel pulsing would create an electrical signal was not known that.

Signal Type Pulse Oximetry (Pulse ox): On the other hand, there were reasons to believe that the signal can be a pulse ox signal. Pulse ox signals are only capable of achieving heart rate as it measures when the blood vessel pulse. Currently, the device of this disclosure can only measure heart rate. In addition, the PO waveform was wide and triangular in shape with no deflection on the y-axis, which is very similar to the signal collected by the device of the disclosure. Lastly, it could be a PO signal as the location of the sensors is around the radial blood vessel, typical in getting an accurate measurement. This is the only location to get a strong signal where a large blood vessel exists.

Bench Test—Theory: A key differentiating factor between pulse ox and ECG signals is the timing in which the peaks occur. ECG signals are measurements of the electrical signals as they pass through the body, which are capable of reaching the wrist very quickly after a heartbeat. PO signals are measures of the flow of blood through a blood vessel, which takes much longer to reach the distal locations of the body such as the wrist. Thus, by comparing the signals collected by the device to a typical PO sensor and ECG sensor, a conclusion can be drawn. One can determine what type of signal it is by determining if the peak time of the signals by the device occurs at the same time of the ECG or PO signal.

Setup: To test the signals of the device against the signals of a typical ECG and PO sensor for time correlation, a common measuring device was needed. The ECG device used was a classical ECG base Circuit as it has been previously been validated to work well. The PO device is a simple LED and Photodiode system setup as it is easy to implement. To collect the signals from each of the devices the signals were sampled using computer based measurement tools. The set up sampled the data at a rate of 300 Hz, which was then converted into a digital signal. In order to prevent crosstalk between the devices, two USB-231 samplers were needed, each powered through an isolated source. In some embodiments, two individual computer were used for powering the samplers. Both data streams enter into the same computer to link the timing clocks of the recording devices. To ensure the two devices were isolated, a data stream USB isolator was used. For each analog-digital-converter (ADC) sampler, the Channel 0 was used. The device used a differential configuration with the SIG trace of the board connected to the CH0H and the ground of the board connected to the CH0L. An ECG Click™ was used, as understood in the art. Both the ECG Click and PO sensor used a single-ended configuration with their output going into the CH0H pin. The ADC sampler was the power supply for both the ECG Click and PO sensor. The test recorded 1 minute of data comparing two of the devices at one time.

Additional filtering was applied using Matlab™ to the signal of the device to eliminate 60 Hz and other noise.

Figure 15:
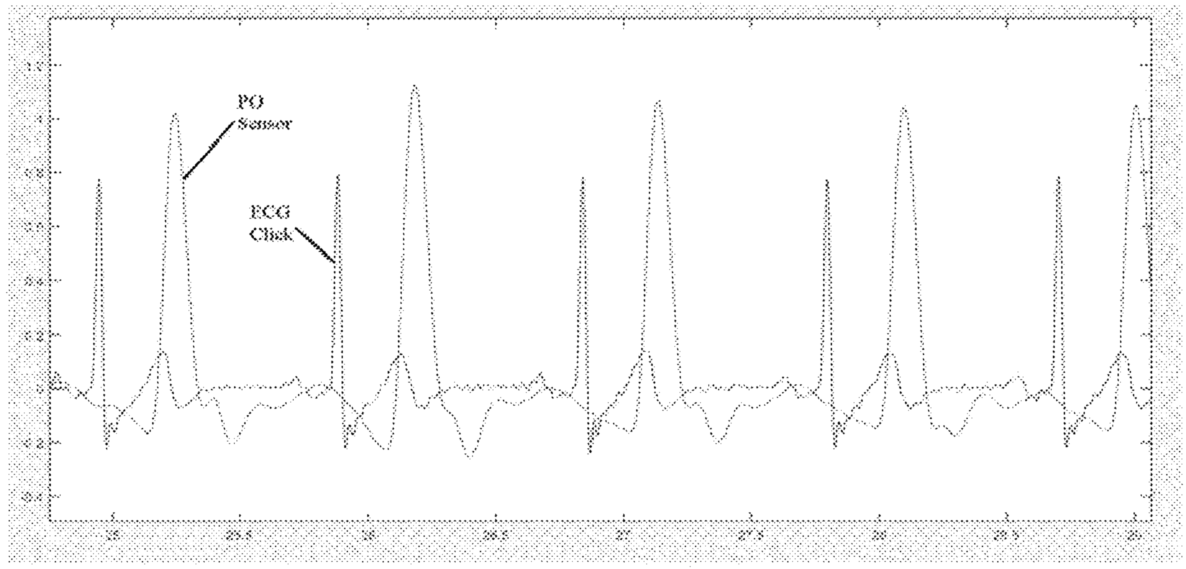
FIG. 15 shows the Pulse Oximetry (PO) and ECG Click signals.

Results: ECG Click vs Pulse Ox: This test serves as a benchmark between a known PO and an ECG sensor. This test will show the variance in time of the peak occurrence. For the ECG Click, two electrodes were placed on each arm and third place was placed on the left lower torso. The PO sensor was placed on the index finger of the left arm. The results are shown in FIG. 15. The first trace is the ECG Click, and the second trace is PO.

As shown in FIG. 15, there was a discrepancy in time between the peaks of the two signals. The PO peak occurred slight after the ECG peak and occurred around the time of the T wave of the ECG. This confirmed that the test should be able to differentiate between the PO and ECG signals.

Figure 16:
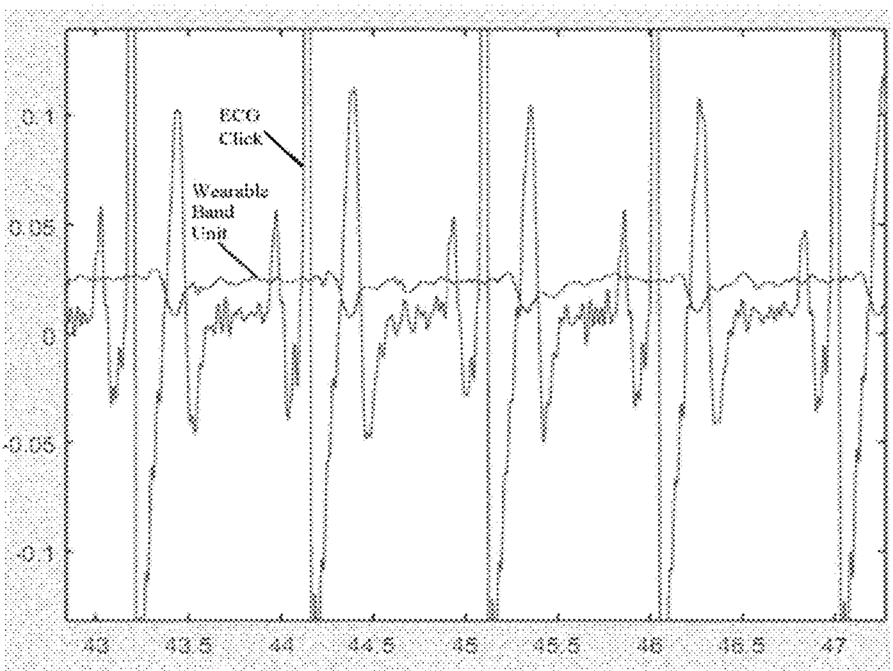
FIG. 16 shows the comparison between the signals collected by an ECG Click and the device of this disclosure.

Results: ECG Click vs Wearable band unit: This test compared the signals of a wearable band unit placed on a single wrist (as explained in Section: Wearable band unit Signal) and the ECG Click placed at the same location. The results are shown in FIG. 16. The first trace is ECG Click and the blue trace is the wearable band unit.

The results showed that the peak of the wearable band unit did not match up with the peak of the ECG Click. This suggests that the signals gathered from the wearable band unit is not an ECG signal. In addition the wearable band unit's peak coincides closely to the T wave of the ECG, which suggests that it may be a PO signal. ECG signal from ECG Click was collected from a mid-location around the chest. This was not a true representation of a true ECG around the wrist (which is not detectable by a current off-the-shelf product). However, it was safe to say the timing of the peak between a chest base ECG and wrist based ECG would coincide because the electrical signals pass through the body very quickly.

Figure 17:
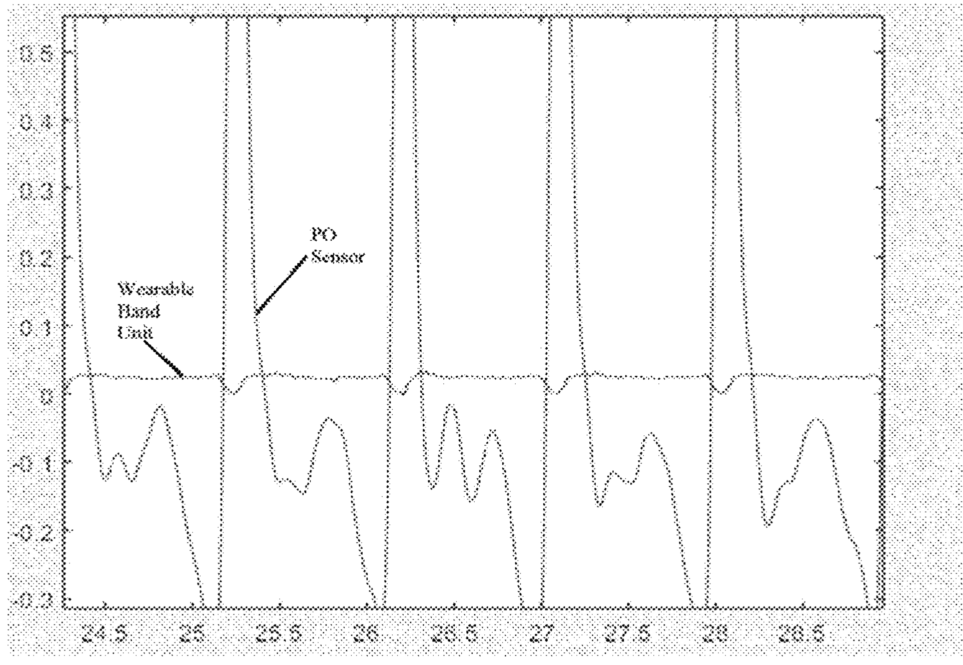
FIG. 17 shows the comparison between the signals collected by the PO sensor and the device of this disclosure.

PO vs. Wearable band unit: This test compared the wearable band unit placement on a single wrist (as explained in Section: Wearable band unit Signal) and the PO sensor. The same location was used to gather signals from the PO sensor (the index finger of the left hand). The results are shown in FIG. 17. The first trace is from the PO sensor and the second trace is from the wearable band unit.

The results show the peak of the PO sensor and the wearable band unit coincide. This suggests the signal from the wearable band unit is indeed a PO signal. The width of the pulse signal is much larger than the wearable band unit signal. It is believed that this is because the two method the wearable band unit of collecting the pulse is through measuring electrical pulses of the radial blood vessel and not through sending light as completed in the Pulse Ox sensor. Thus the signal are likely to look different, but the timing of the occurrence should match up.

Discussion: The results suggest that the signals detected by the wearable band unit placed in the wrist was in fact a PO signal. Although the timings match, there are still some questions to be answered. The most important one is how exactly is a capacitive sensor detecting an electrical signal from the radial blood vessel pulsing. Without being bound to a particular theory, there are two hypotheses. The first is that there is a pressure applied to the capacitive sensor while the blood vessel expands, leading to an electrical spike. The second is that blood contains many charged ions and as the blood flow increases as the vessel pulses, the capacitive sensor can detect these charges. An additional question is how the grounding plate contributes to the gathering of the pulse ox signal. In theory, the signal should be able to be gathered without a second sensor (the grounding).

Figure 18:
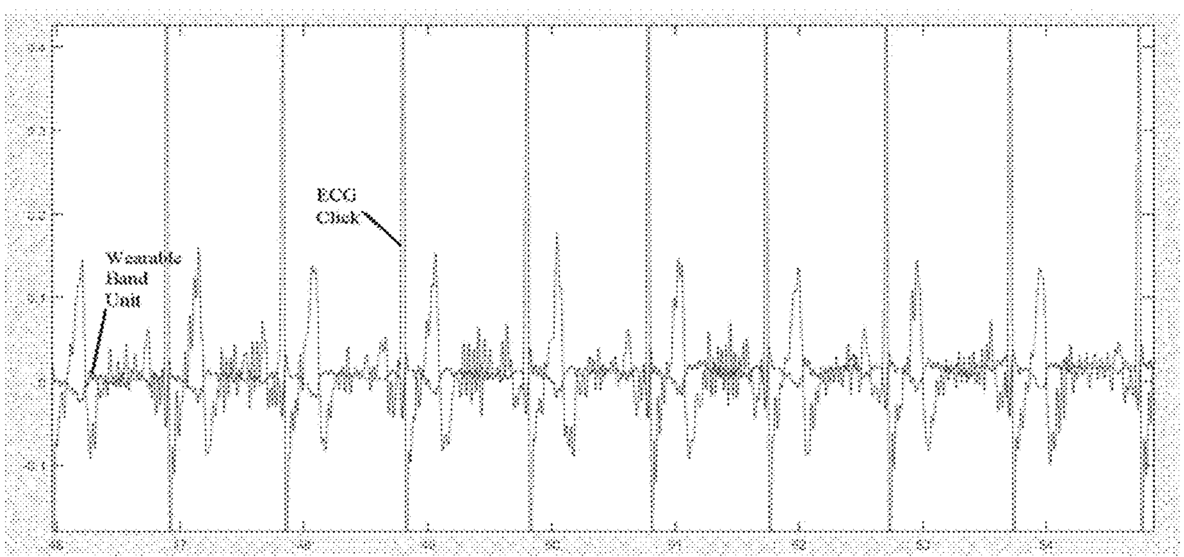
FIG. 18 shows the signals collected by an ECG Click and the device of this disclosure with placed on the wrist of a user.

A second test was conducted to determine whether the wearable band unit is able to detect any ECG signals at the wrist. This test compared the ECG Click (used in the same configuration) against the wearable band unit in which both wrist were used (the capacitive sensor on the left wrist and the grounding plate on the right). The results are shown in FIG. 18. The first trace is ECG Click and the Blue trace is the wearable band unit.

The results show the between two wrist (wired), the wearable band unit does produce an ECG signal. This confirms that a PO signal is produced only when the device collects data from a single wrist in the current configuration (location).

The wearable band unit is able to collect a small 1 Hz periodic triangle shaped signal when placed on a single wrist. This location is of interest because it can drastically improve the comfort and adoptability of the wearable band unit and eliminate the need of creating a wireless system comprising multiple wireless sensors. However, this signal must be confirmed to be an ECG signal in order to proceed with trying to extract ECG features from it. To identify this, the timing of the wearable band unit peak was compared against the timing of ECG Click and PO sensor. By utilizing an isolated, two ADC sampler test configuration, the signals can be overlaid and to correlate with the timing of each other's peak. The results show that the wearable band unit's peak occur as the same time as the PO sensor. Additionally, it seemed to occur around the T wave of the ECG Click, which was also seen when comparing the ECG Click signal to the PO sensor. This suggests that the signals from wearable band unit at this location is a PO signal.

Based on these results, two paths can be taken. The first is to continue working on developing a wireless system which implements multiple sensor place around the body (likely one on each wrist and possibly a reference RLD sensor). The second is moving along with collecting ECG signals from a single arm but at a different location when the much smaller ECG signal will not be masked by the PO signal, which would require a much higher amplification of the gathered signal with highly sophisticated filtering in order to extract an ECG signal.

Determine Sensor Locations of the Wearable band unit on a Single Arm: Sensor testing on a single arm was conducted to determine optimal areas for reading ECG signals along the same arm. The signals from different areas were recorded so that they could be analyzed to determine the type of biometric gathered. (ECG vs. Pulse Oximetry) In theory, an increased distance between the electrodes will result in a larger amplitude signal.

Testing Method includes the following steps: 1) Strap the wearable band unit onto location one; 2) Strap/hold the electrode onto location two; 3) On the external application select the wearable band unit being used; 4) Select "Stream"; 5) Stay as still as possible and wait for a consistent signal; and 6) Record data and assign a file name/link to the recorded data.

Figure 19:
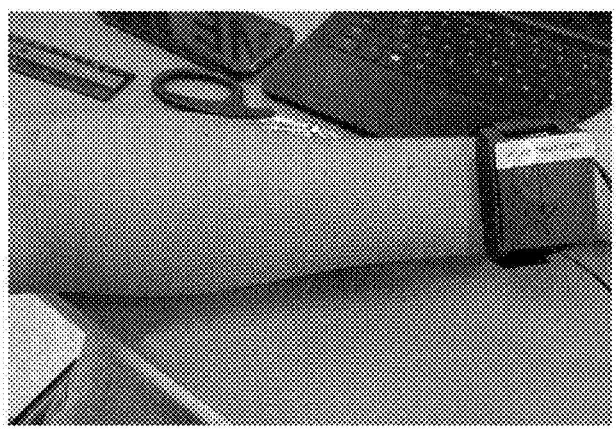
FIG. 19 shows the device worn on the bottom side (palm side) of the wrist.
Figure 20:
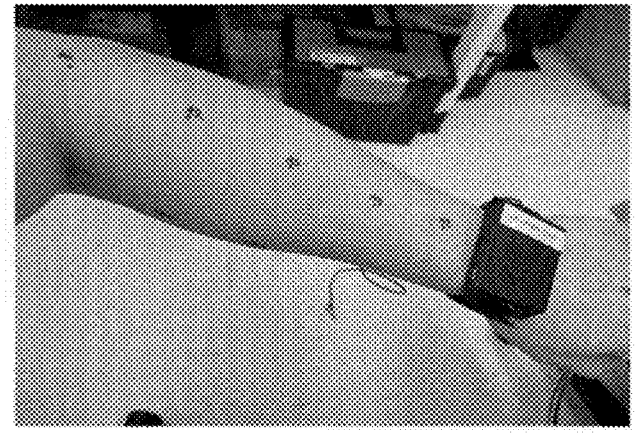
FIG. 20 shows the device worn on the top side (knuckle side) of the wrist.

Location 1 of the Device:

In some testing, the band of the wearable band unit was placed on the wrist because it is an area of high interest. User A's tests were primarily with the band on the bottom of the wrist (palm side, FIG. 19). User B's test were primarily with the band on the top of the wrist (knuckle side, FIG. 20). For the grounding plate locations (location two), coordinates were drawn on the arm to have consistent testing locations.

Figure 21:
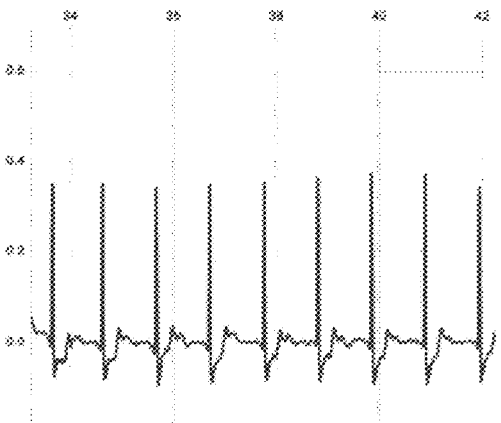
FIG. 21 shows data collected by the device from around the chest.
Figure 22:
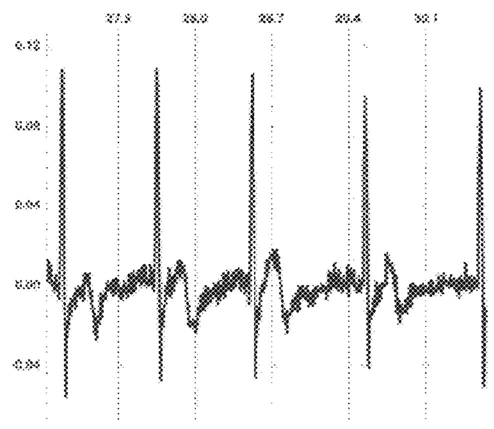
FIG. 22 shows data collected by the device from opposite wrists.

Data around the chest and opposite hands: Data was collected in areas around the chest by placing the wearable band unit proximate to the heart and the electrodes directly below the ribs (FIG. 21). Data was also collected from the opposite hands by placing the wearable band unit on the right wrist and the grounding plate on the left wrist (FIG. 22). The data collected as illustrated in FIGS. 21-22 can be used as a reference when analyzing data that came from just the single arm. Results from the chest area and opposite hands were consistent, and periodic in nature, thus serving as a reliable benchmark when collecting data along the single arm.

Figure 23:
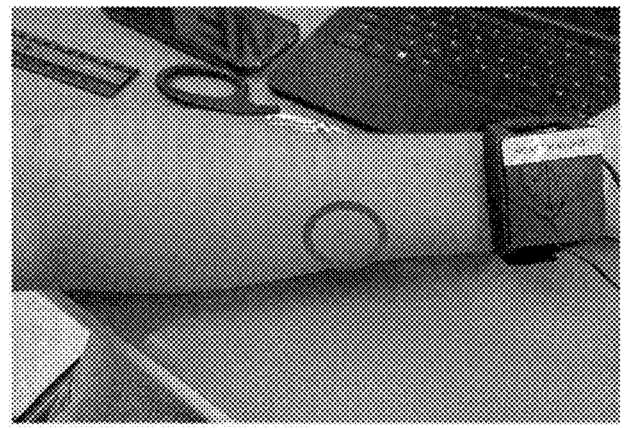
FIG. 23 shows attachment of the device on the wrist of the user and the location of the electrode at D3.
Figure 24:
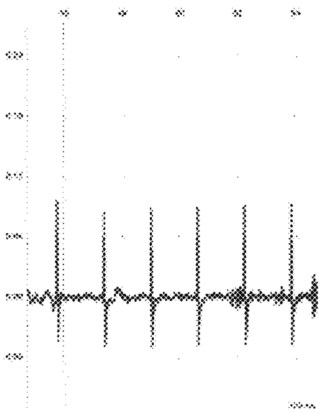
FIG. 24 shows signal found around D3.

Data around the forearm: Some of the data around the forearm did not yield ECG or pulse ox like signals. On the other hand, some spot, for example, spot D3 (shown in the circle) on the inner forearm as shown in FIG. 23 that would yield consistent, periodic results as shown in FIG. 24. When the data was collected, an electrode was strapped to the D3 spot.

The signal displayed in FIG. 24 has a period of about 1.8 seconds, which is unusually long for an ECG or PO. The amplitude of this graph is also relatively high compared to signals around the chest (where one would expect amplitude to be the highest). This finding means that the peaks shown in the FIG. 24 is not actually an ECG or PO, but rather a result of interference from an outside source during testing.

Figure 25:
FIG. 25 shows the positions for attachment of the sensors on the left bicep of the user.
Figure 26:
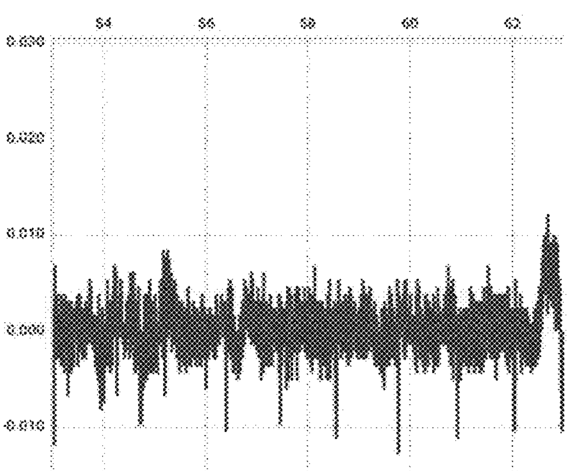
FIG. 26 shows the signals detected at the H2 position.

Data around the upper arm: Some of the data around the upper arm did not yield ECG or PO signals. On the other hand, some spot, for example, spot H2 (FIG. 25) on the bicep that yielded a periodic signal a couple times, peaking every second (FIG. 26). The results were not consistent and difficult to repeat. The signal was also not strong or very clear.

Figure 27:
FIG. 27 shows the attachment of the electrode of the device strapped to mid-bicep (G1), with relaxed muscles and hand.
Figure 28:
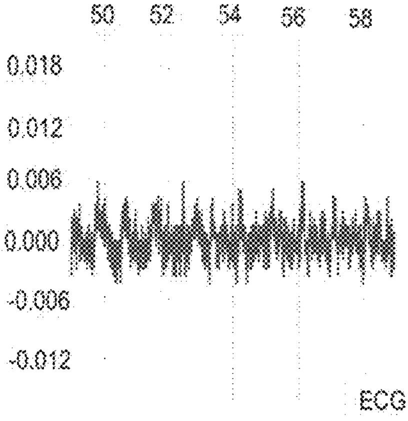
FIG. 28 shows the signals detected location near G1.

FIG. 27 shows the electrode attached to a particular spot G1 at the mid-bicep, with relaxed muscles and hand. The signals collected are shown in FIG. 28 had peaks with a period of ~1 second, which resembles the peaks of an ECG or PO. However, the peaks of this graph were relatively low compared to the rest of the data in FIG. 28. The amplitude of the peaks are ~0.006V which is low compared data found around the chest (~0.35V).

Data around the shoulder: The data collected around the shoulder yielded ECG or pulse ox signals quite consistently. The front shoulder area yield the best quality of results with the most consistency.

Figure 29:
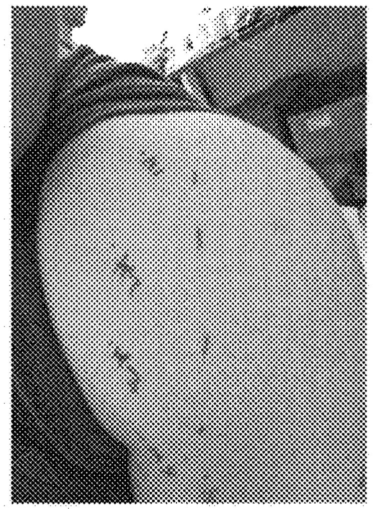
FIG. 29 shows attachment of the location K3 at the centre of the shoulder belly and a few centimeters above the upper arm.
Figure 30:
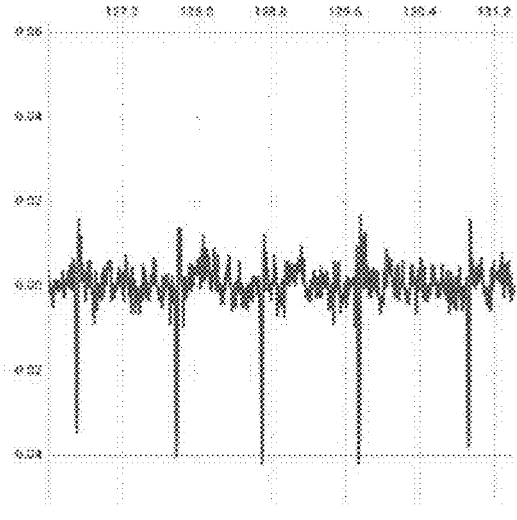
FIG. 30 shows the signals detected at location K3.

FIG. 29 shows the example location K3 at the centre of the shoulder belly and a few centimeters above the upper arm, where the signals were collected. FIG. 30 shows that the signal had an amplitude of peaks averaged at 0.04, the greatest around the shoulder area.

Figure 31:
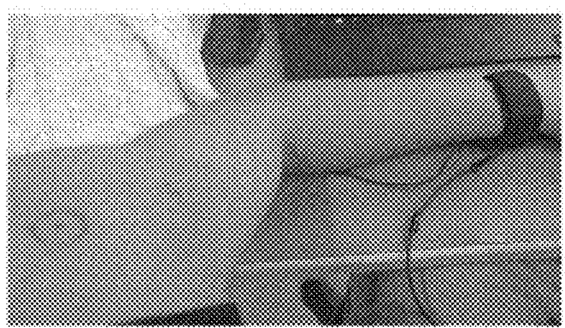
FIG. 31 shows the location I1 as identified by the circle on the shoulder of the user.
Figure 32:
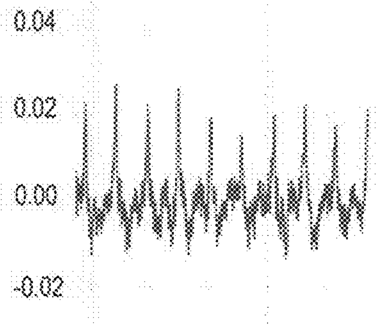
FIG. 32 shows the signals collected at location I1.
Figure 33:
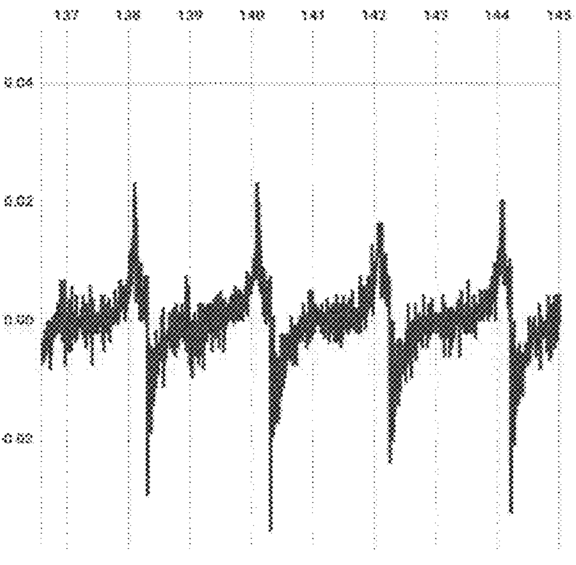
FIG. 33 shows ascending wave before peak.
Figure 34:
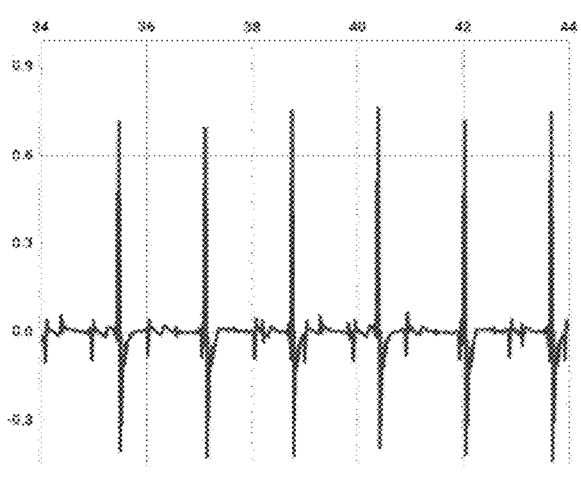
FIG. 34 shows large signals covering ECG.
Figure 35:
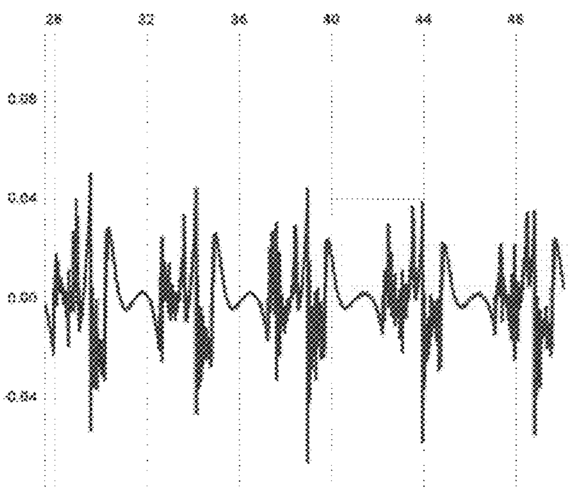
FIG. 35 shows the curve between peaks
Figure 36:
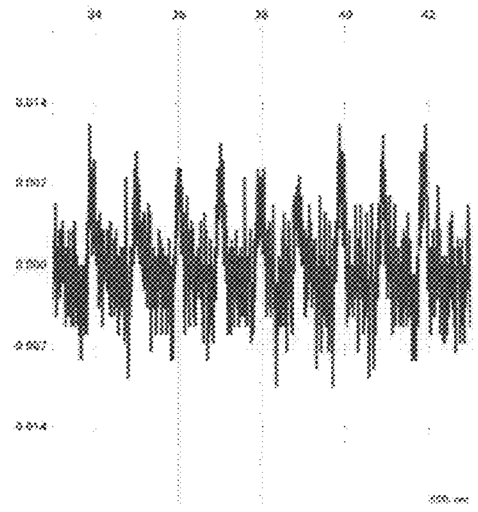
FIG. 36 shows the descending wave before peaks.

FIG. 31 shows an example location I1 (circled dot) on the front shoulder where the signals were collected as shown in FIG. 32. The signals show clear, periodic results coming from I1, with peaks about every 1 second.

Other signals: While testing, other periodic signals were found. They were reasoned not to be ECG or pulse ox since their signal have a period of 1.5 to 4 seconds whereas, heart rate is around 1 second per beat. There was a range of amplitudes and shapes of these signals. Some of these signals are shown in FIGS. 33-36.

Conclusion: The clearest and most consistent signal was found when the grounding plate was on the front shoulder and the band was on the wrist. The forearm and upper arm were unsuccessful in producing an ECG like signal consistently and clearly. This result is in agreement with the theory stated in the purpose, but more trials need to be conducted in order to further confirm it. Another possible reasoning for the strong signals is that the electrode was placed near the axillary artery, a large blood vessel found near the shoulder.

Comparison between the ECG Click and Wearable band unit around the Armpit: The purpose of the test is to compare the ECG Click against the wearable band unit located around the armpit, in order to time-correlate features between the two signals. In particular, there seems to be a p wave inflection on the wearable band unit signals collected from the armpit. However, the signal is quite small, on the same magnitude of the noise. If the time the suspected wearable band unit P wave occurs correlates with the time the p wave is detected on the ECG Click, it will build confidence that it is P wave. In addition, understanding the correlation of all other ECG features between the two devices will be of value in determining the ability of the wearable band unit located at the armpit.

Setup: A setup similar to previous comparison was used. To test the wearable band unit signal at the armpit, the ECG Click was used, a common measuring device was also needed. This set up sampled the data at a rate of 300 Hz, then the data was converted into a digital signal. In order to prevent crosstalk between the devices, two computer ADC samplers were used, each powered through an isolated power source. In some embodiments, the ADC samplers were powered by two individual computers. Both data streams enter into to same computer to permit time syncing of the devices. To ensure that the two devices were isolated, a data stream USB isolator was used. For each ADC sampler, the Channel 0 was used. The wearable band unit used a GND trace and the SIG trace into the ADC Sampler. The ECG Click was powered by the ADC sampler, thus only required a single analog output trace to be used. Channel 0 displayed on TRACER was the signal from the ECG Click board and Channel 1 displayed on TRACER software was the signal from the wearable band unit placed on the armpit. The wearable band unit was tested with both an electrically coupled capacitive sensor (having capacitively coupled electrode leads) and the conventional industry capacitive sensors. The test recorded 1 minute of data comparing two of the devices at one time. Additional filtering was applied to the wearable band unit data by Matlab™ to eliminate 60 Hz and other noise.

Results: The test was conducted 3 times for the configuration using the capacitive sensor and 3 times for the configuration using the electrically coupled capacitive sensor, which provides stable signals. The results are shown FIGS. 37-40C. Individual data is shown for both the ECG Click and wearable band unit with capacitive sensor and with electrically coupled capacitive sensor and then some dataset showing the time correlations between the results.

Figure 37:
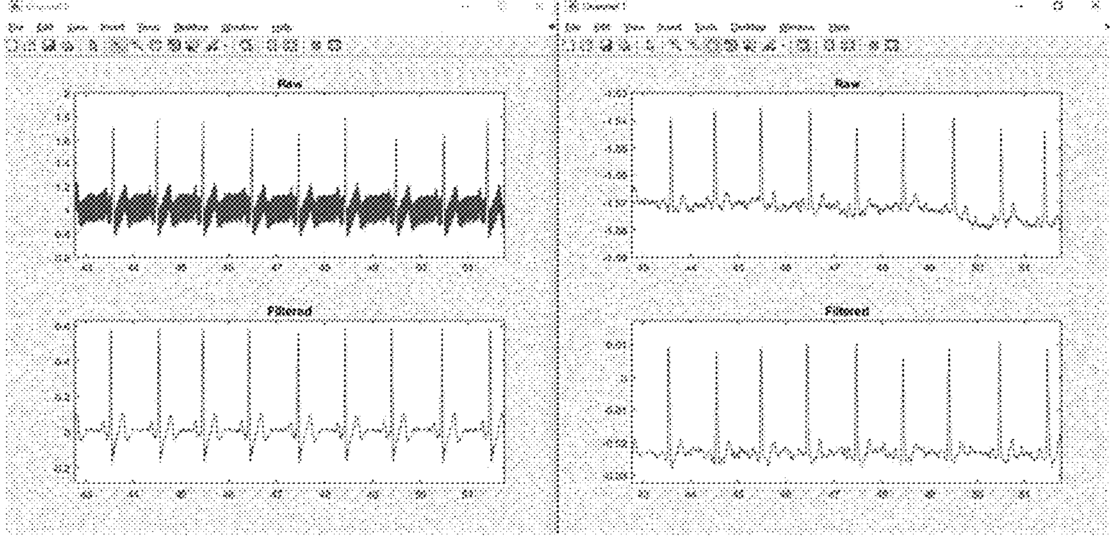
FIG. 37 shows the isolated data set at the armpit by ECG Click and the device of this disclosure.
Figure 38A:
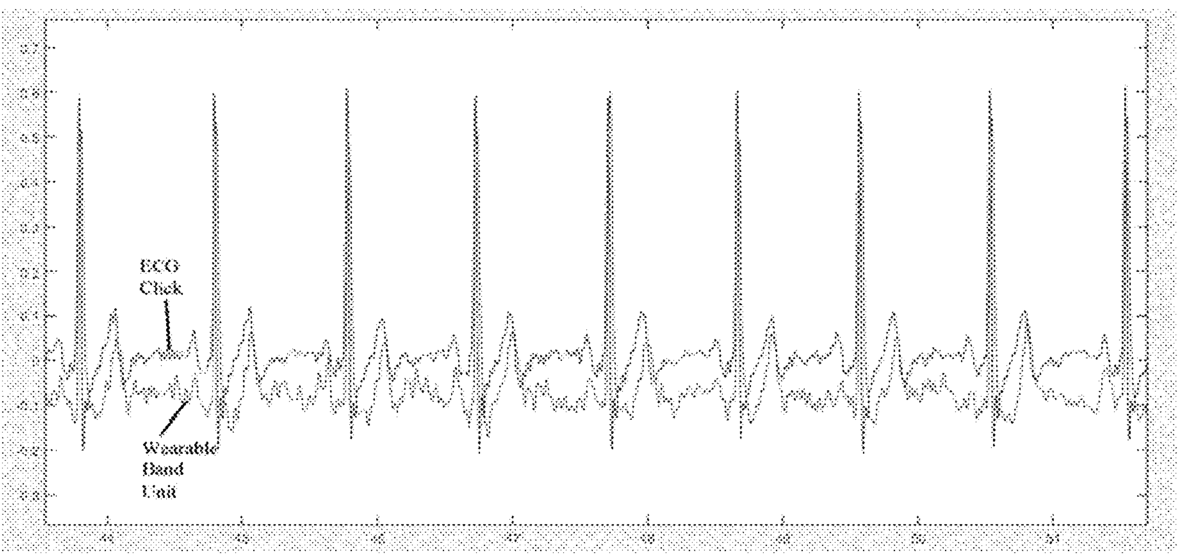
FIG. 38A-38C show the comparison of results in Test 1.
Figure 38B:
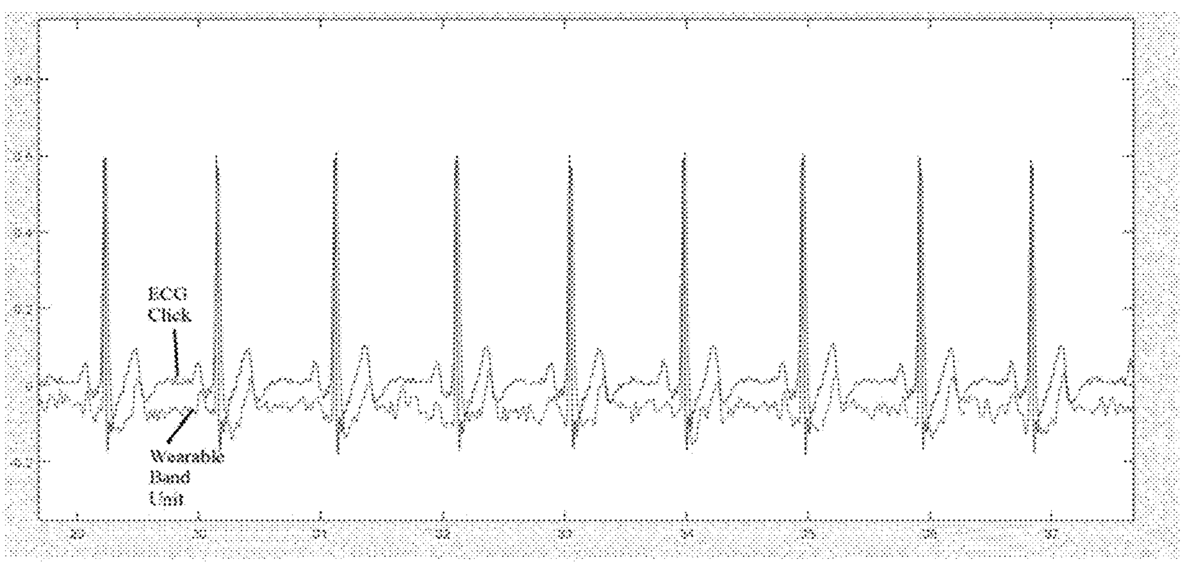
Figure 38C:
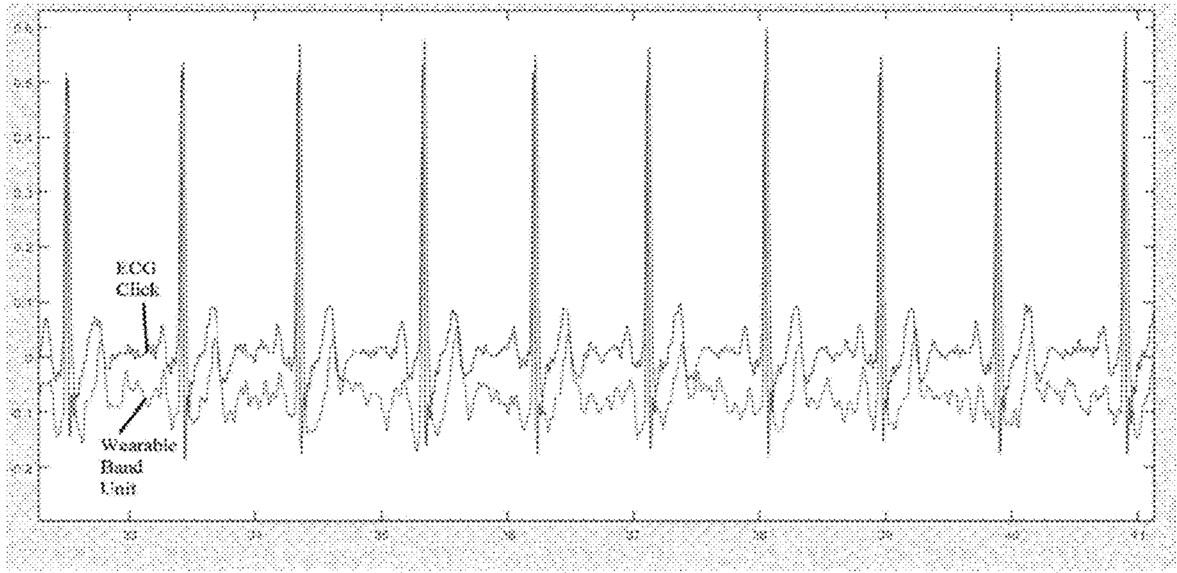

Capacitive Sensor vs. ECG Click: Isolated Data set are shown in FIG. 37, Channel 0 is ECG Click, and Channel 1 is wearable band unit with capacitive sensor. The comparison data is shown in FIGS. 38A-38C (first signal is ECG Click, second signal is the wearable band unit).

Figure 39:
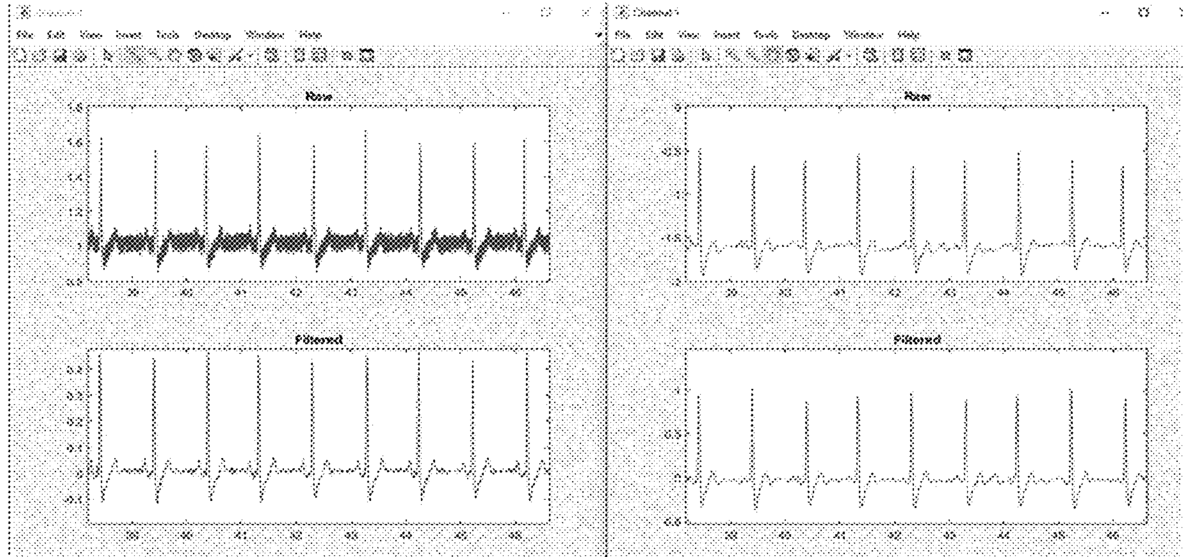
FIG. 39 shows isolated data set at the armpit by Modified electrically coupled capacitive sensor vs ECG Click.
Figure 40A:
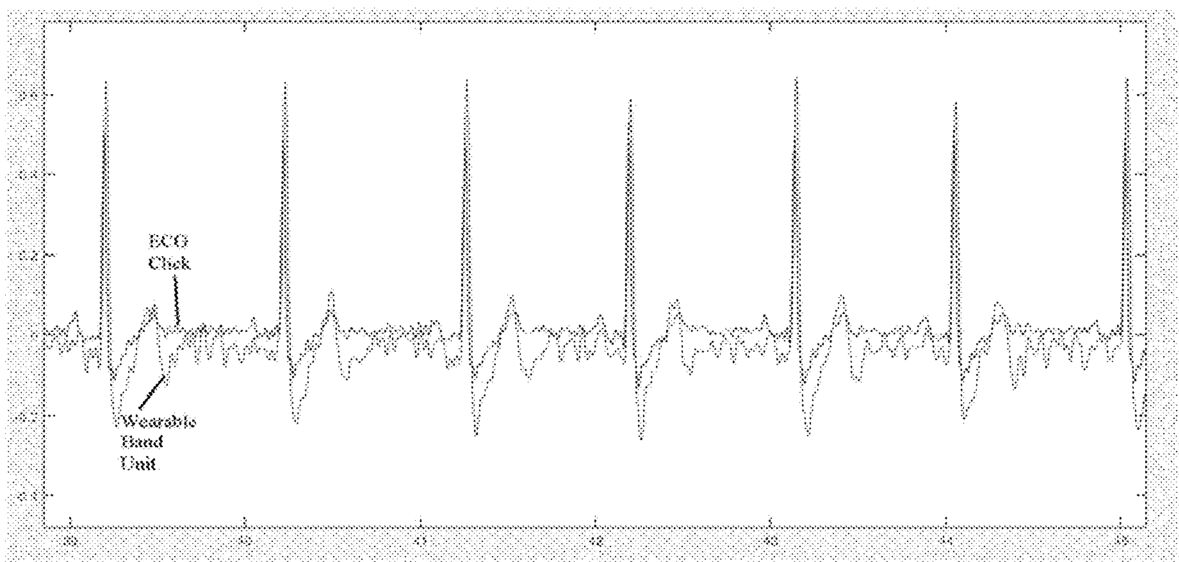
FIGS. 40A-40C show the comparison of the data from the device of this disclosure and the ECG Click.
Figure 40B:
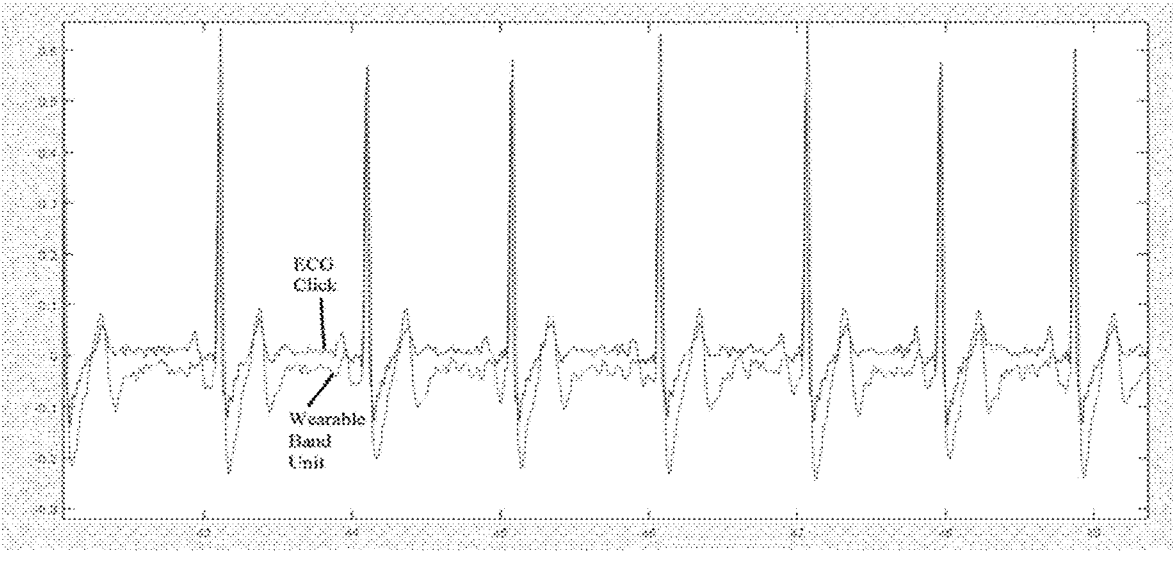
Figure 40C:
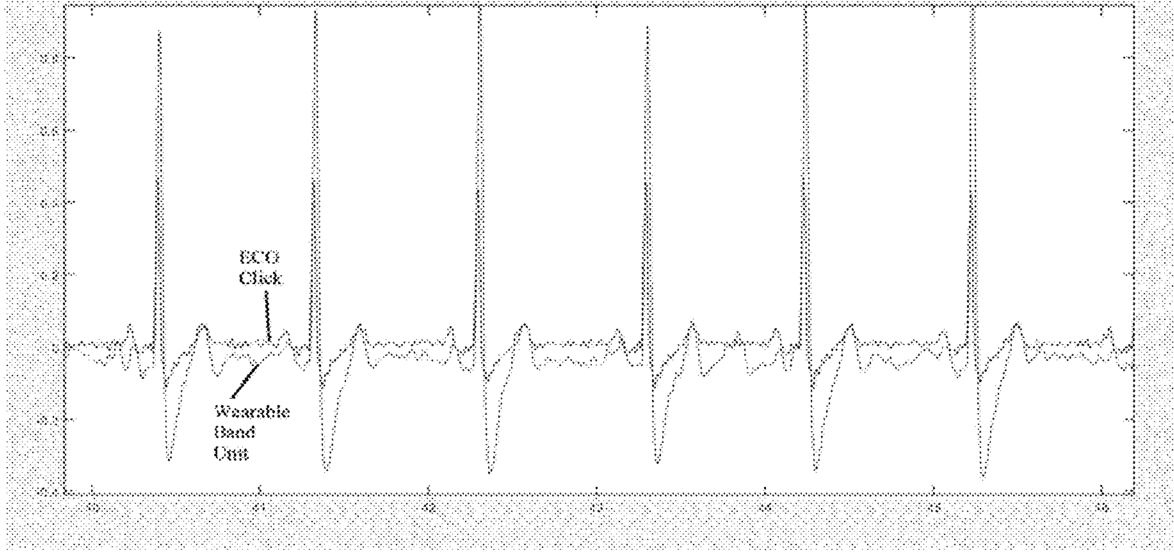

Modified electrically coupled capacitive sensor vs ECG Click: Isolated Data set is shown in FIG. 39, in which Channel 0 is ECG Click and Channel 1 is wearable band unit with modified electrically coupled capacitive sensor. Comparison Data sets are shown in FIGS. 40A-40C, in which the first signal is from the wearable band unit and the second signal is from the ECG Click.

Discussion: It can be seen that the signal produced from the wearable band unit (be it from the conventional capacitive sensor or the electrically coupled capacitive sensor) correlate in time when analyzing the QRS complex and T wave. One thing to notice is there is a delay between the ECG Click data and the wearable band unit data. However, this is consistently noticed between all features of the ECG.

It is believed this could be cause by multiple things. Without being bound to a theory, the first and more likely is that the wearable band unit signal is processed through the USB isolator, which can induce a delay; the second is that the filtering system is causing the delay; and the final is that the signal is delayed due to the location of the wearable band unit being place on the armpit instead of the chest.

It is also conclusive that the p wave-looking signal from the wearable band unit match up directly with p wave recorded from the ECG Click (of course with the slight delay). This suggests that the signal from the wearable band unit, be it electrically coupled capacitive sensor or Capacitive Sensor, can produce P wave.

Comparing the electrically coupled capacitive sensor to the capacitive sensor, the electrically coupled capacitive sensor has a higher gain (not seen in the graphs as an added gain is applied to the software to view comparable results). The signal from the electrically coupled capacitive sensor had larger noise but with a smaller frequency. The signal from the capacitive sensor is of a smaller magnitude but with a high frequency. However, both are quite comparable.

Conclusion: In conclusion, the P wave is detectable in both setups. Using the ECG Click to correlate when a P wave is occurring makes it easier to identify P waves on the wearable band unit system. Two methods may be used to improve detectability of the p wave: 1) Increase the gain on the initial differential to reduce the influence of the noise applied to the system after the initial gain stage. 2) Apply strong software filters on the data specific to identifying the P wave.

Instrumentation Amplifier vs. Opamp: Experiments were conducted to compare the signal quality from an instrumentation amplifier IC and an op amp IC used for the differential of the two sensor signals.

Figure 41A:
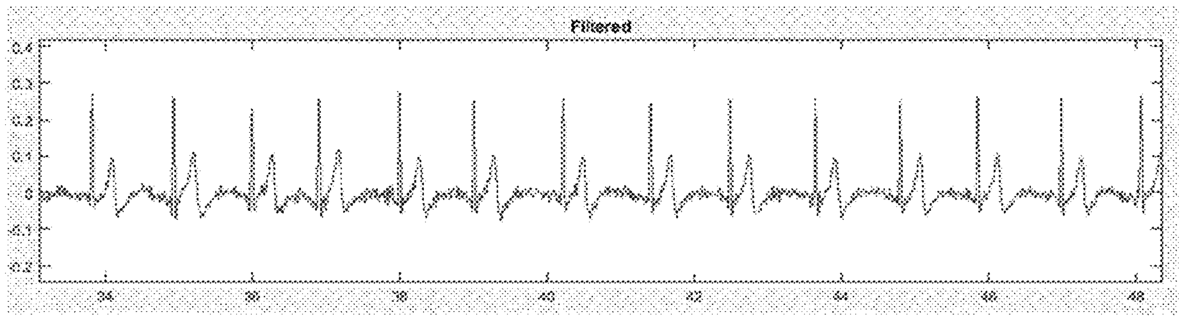
FIG. 41A shows the signal from INA116PA.
Figure 41B:
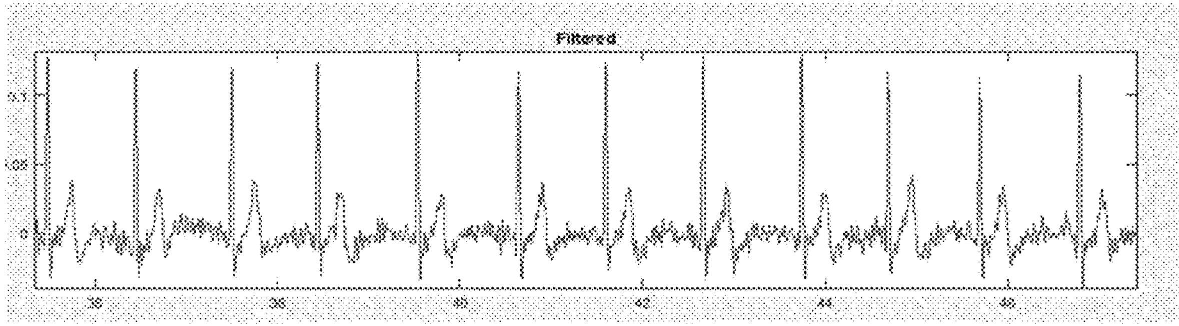
FIG. 41B shows the signal from LMV832.

Procedure: The instrumentation amplifier tested was the INA116PA from Burr-Brown and the op amp used was the LMV832 from Texas Instruments. The modular electrically coupled capacitive sensor setup was used to input the signals into the ICs. An electrode was placed on each thumb. The data was collected through the MC ADC and filtered through MatLab™. The results of each IC are shown FIGS. 41A and 41B.

The results show that the signal from the INA116 (FIG. 41A) and LMV832 (FIG. 41B) improves the signal quality outputted. However, in some embodiments, LMV832 may be preferable considering form factor, power drain, and cost. It is contemplated that other op amp may have more favourable features compared to LMV832.

Mapping Wearable band unit Arm Data: The device of this disclosure is able to gather clean ECG data from the axillary area. The results obtained from the device over various positions on the upper arm are summarized below.

The results received from thumb data were used as the benchmark standard to which the wearable band unit data across various parts of the arm will be compared. A good signal is deemed to be received when a clear QRS complex, and T wave are seen. If a notable p wave is seen, then the results can be considered to be more preferable.

Figure 42A:
FIG. 42A shows the device attached at the shoulder.
Figure 42B:
FIG. 42B-42K show the positions of the sensors and the corresponding signals when the device was attached at the shoulder as shown in FIG. 42A, in which 1 means lateral and m means medial.

Three locations axially along the arm of a user were tested. The first location is at the shoulder as shown in FIG. 42A. The second location is at the upper part of the upper arm, as shown in FIG. 43A, for example, the upper ⅓ of the upper arm, or the upper ½ of the upper arm. The third location is at the lower part of the upper arm as shown in FIG. 44A. The positions of the sensors at these locations around the arms and the corresponding signals are shown in FIGS. 42B-42K, 43B-43K, and 44B-44K, respectively. Sensor Positions at Each Location: In the figures, 1 means lateral (on the other side of the arm relative to the radial artery), and m means medial (on the side of the arm close to the radial artery).

Conclusion: It is evident that the obtained signal quality diminishes as the sensors were placed further and further away from the armpit location. Nonetheless, it is clear that placing sensors around certain positions of the arm in certain orientations yields better signal quality overall. The next stage of this experiment is to study whether the signal quality obtained at these particular locations are reproducible. If the signal quality is deemed to be reproducible, then the device can be further modified in order to better the signal obtained from the determined location.

Figures 42C, 42D, 42E, 42F:
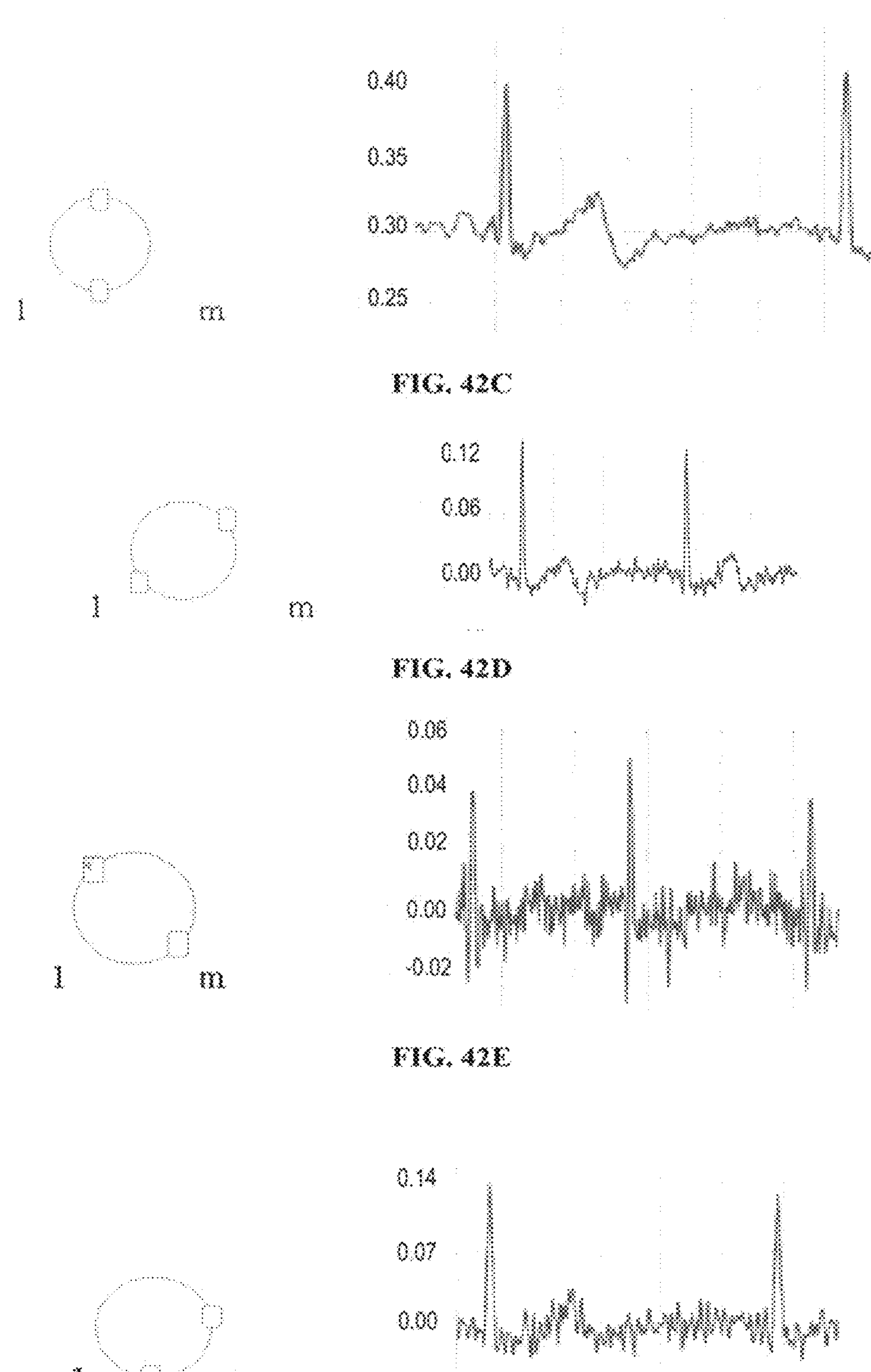
Figure 42G:
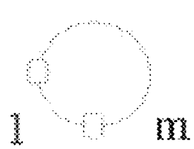
Figure 42G:
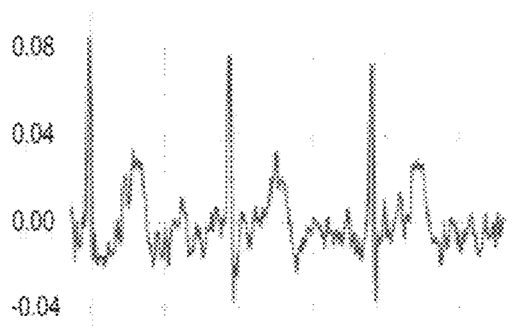
Figure 42H:
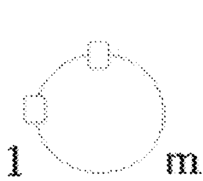
Figure 42H:
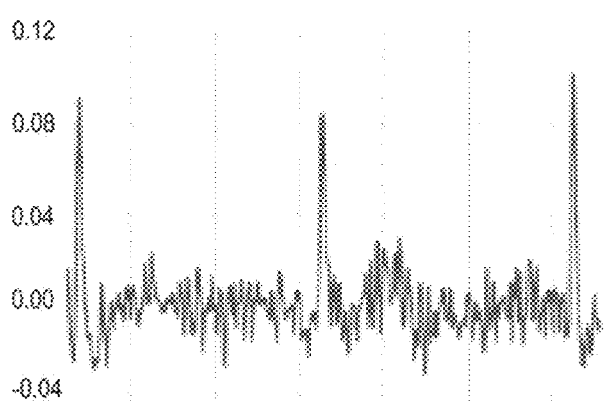
Figure 42I:
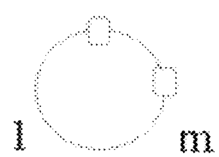
Figure 42I:
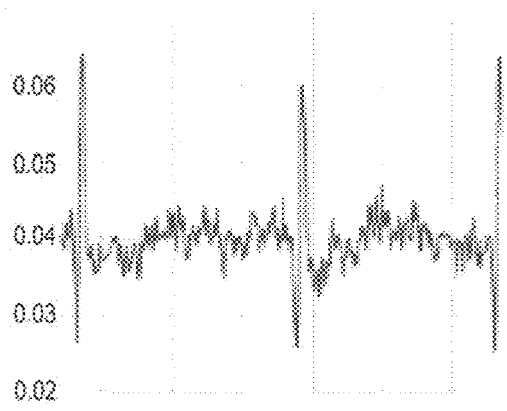
Figure 42J:
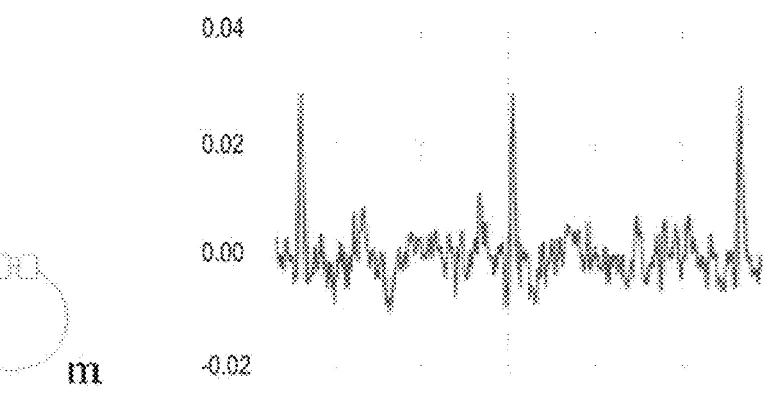
Figure 42K:
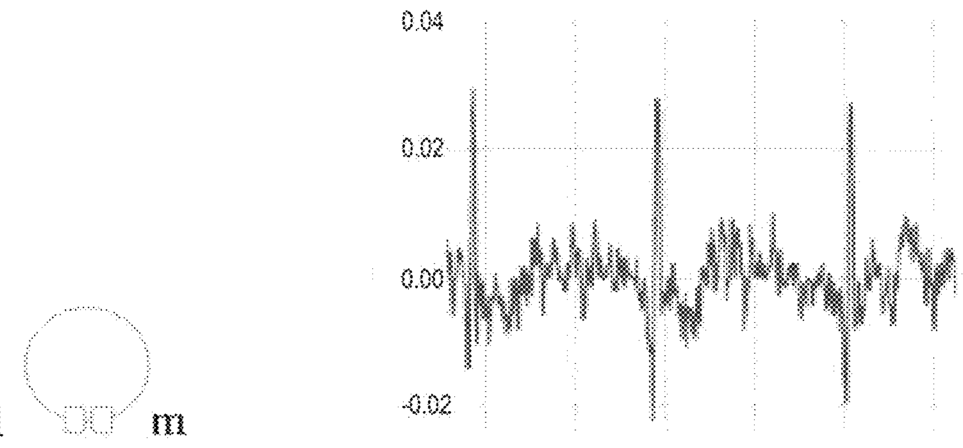
Figure 43A:
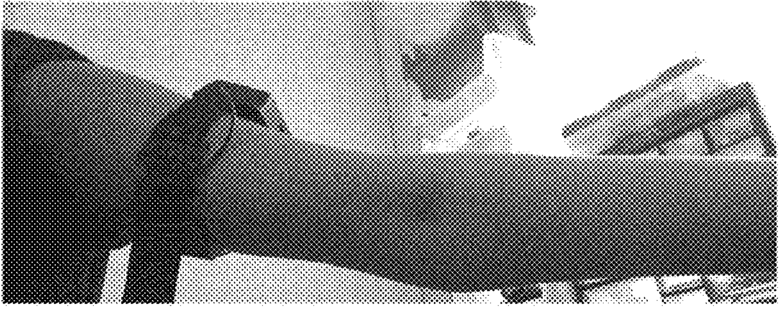
FIG. 43A shows the device attached at the upper part of the upper arm.

It is determined that the when the device is attached at the shoulder as shown in FIG. 42A, the preferred positions of the sensors are those shown in FIGS. 42C, 42D, and 42G.

Figures 43B, 43C, 43D:
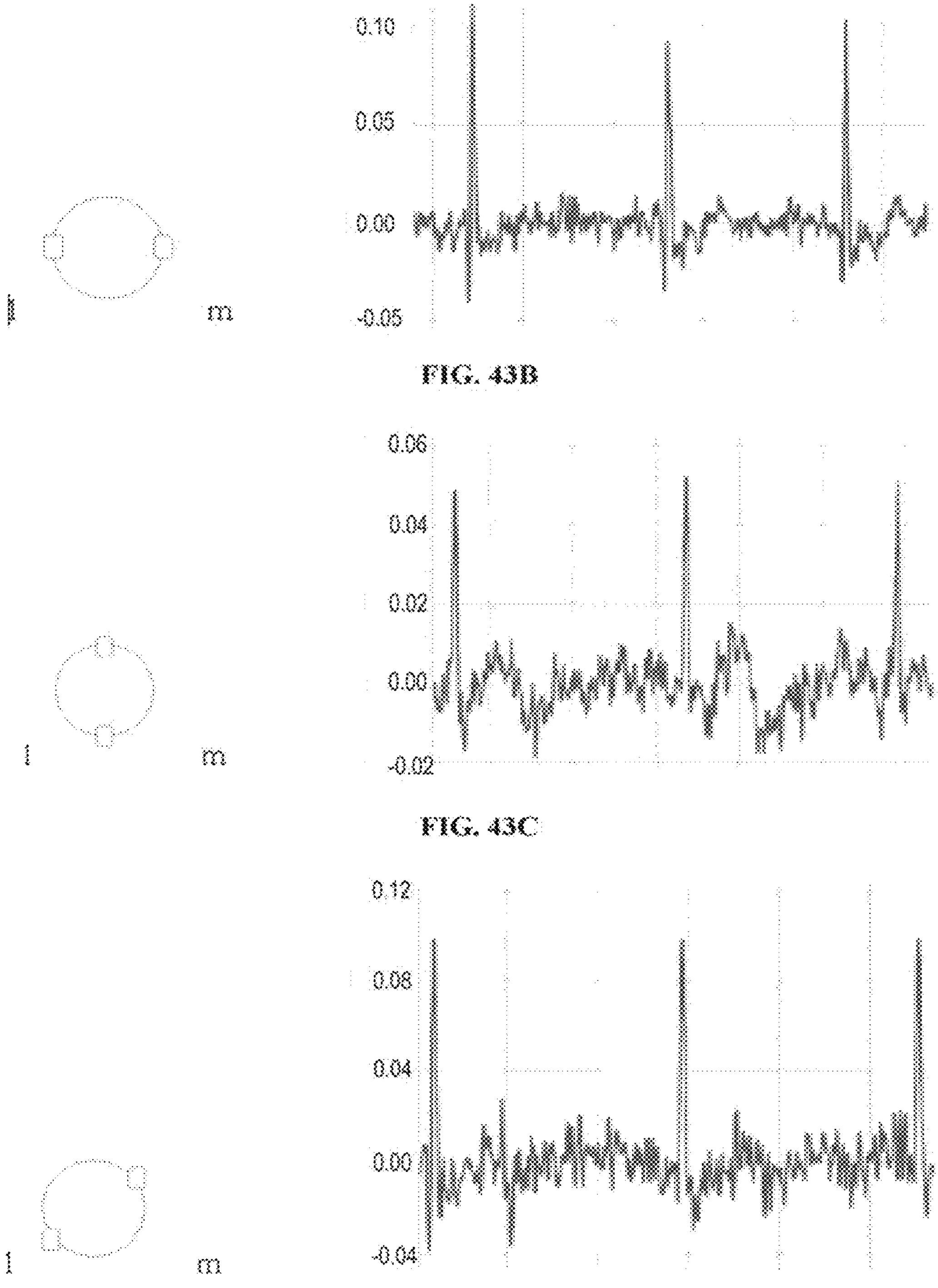
Figures 43E, 43F, 43G:
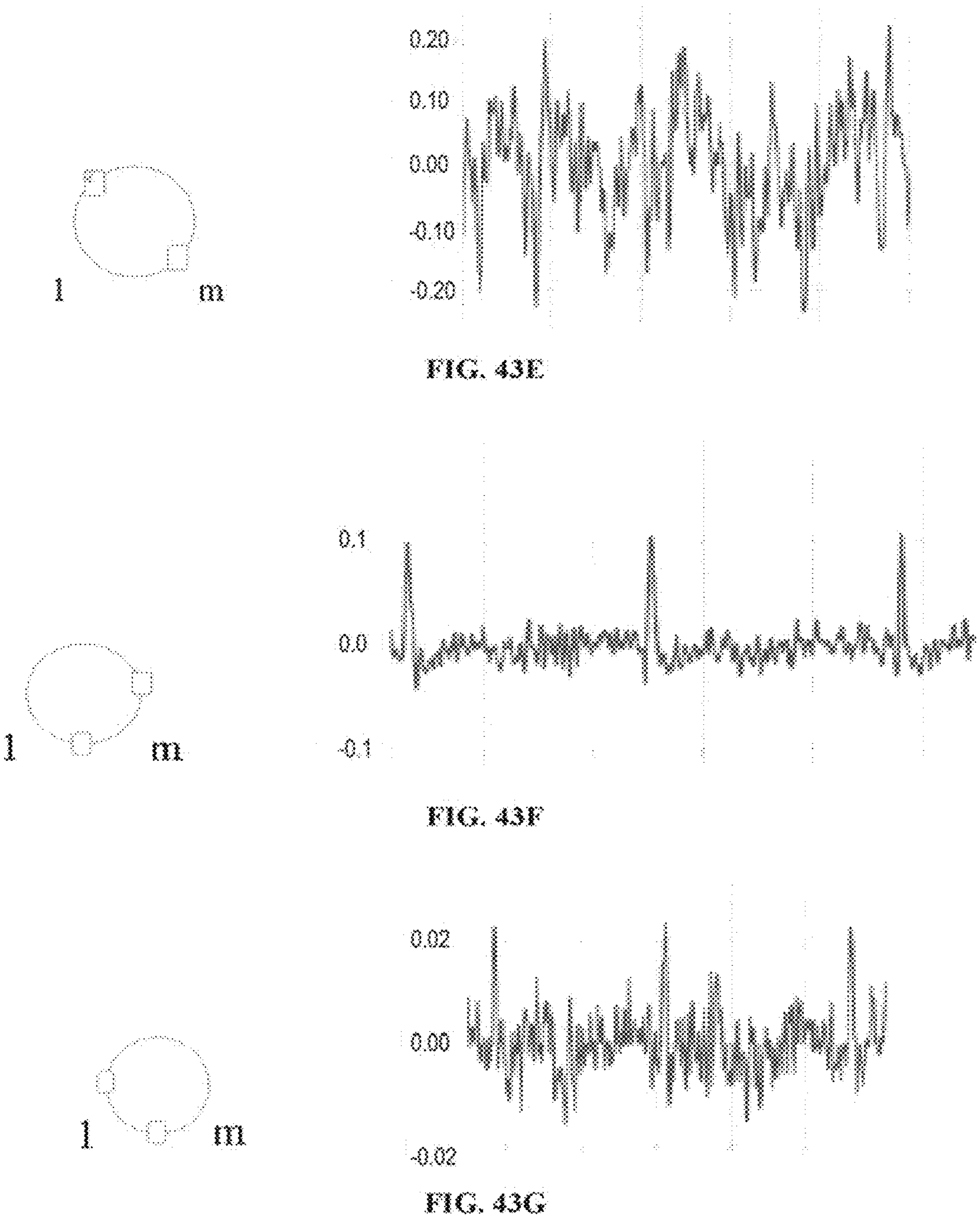
Figures 43H, 43I, 43J:
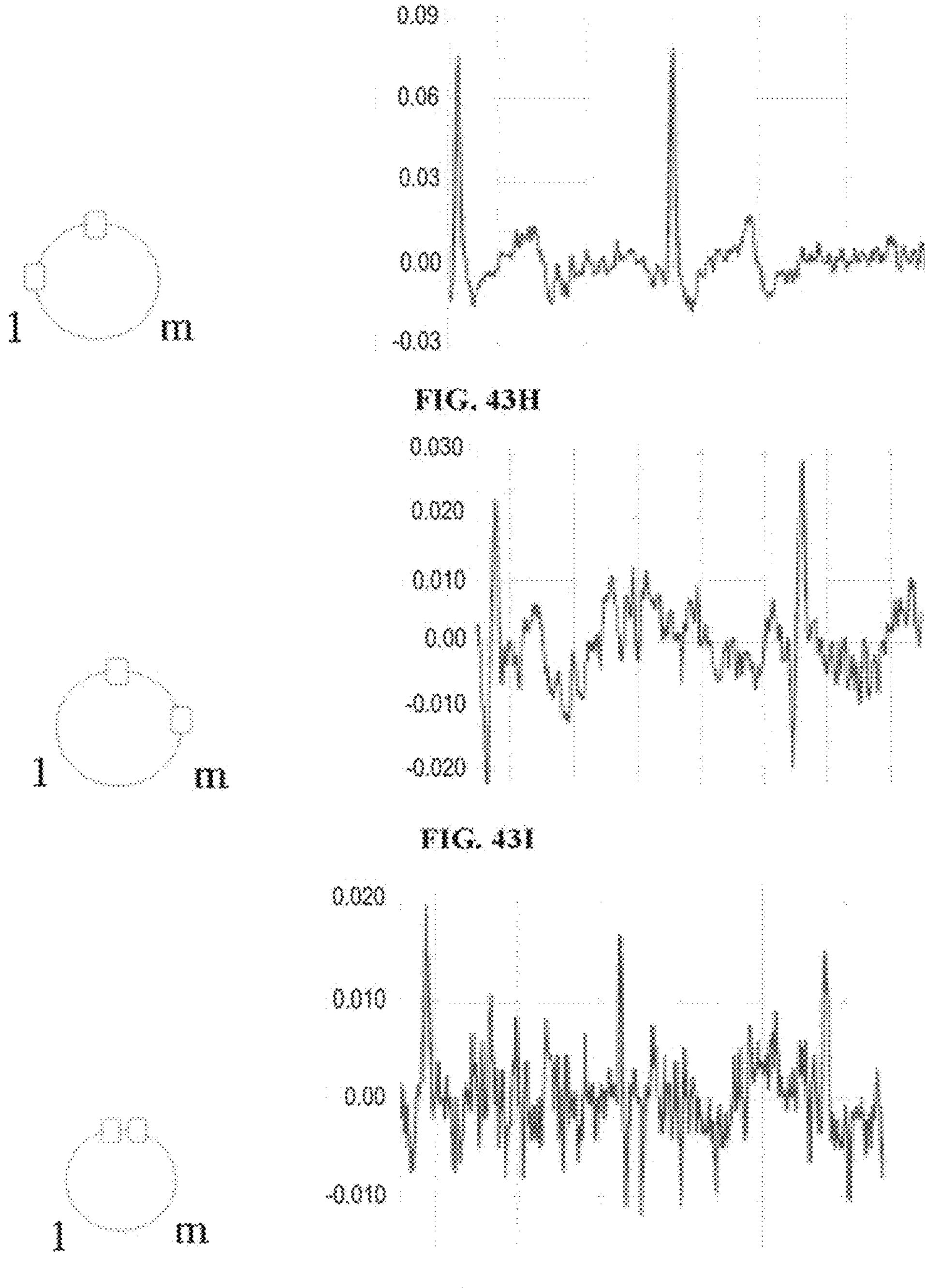
Figures 44C, 44D, 44E:
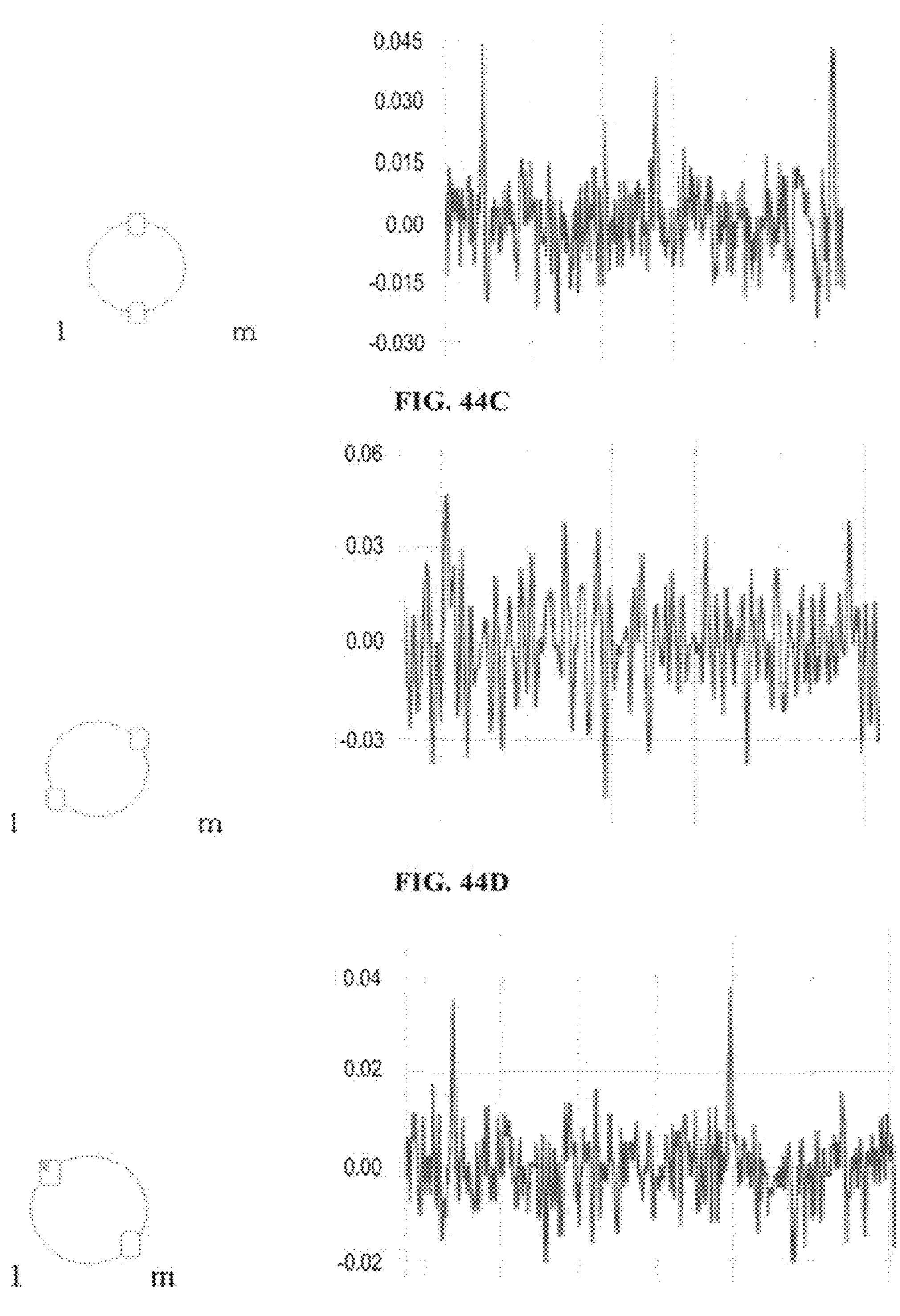
Figures 44F, 44G, 44H:
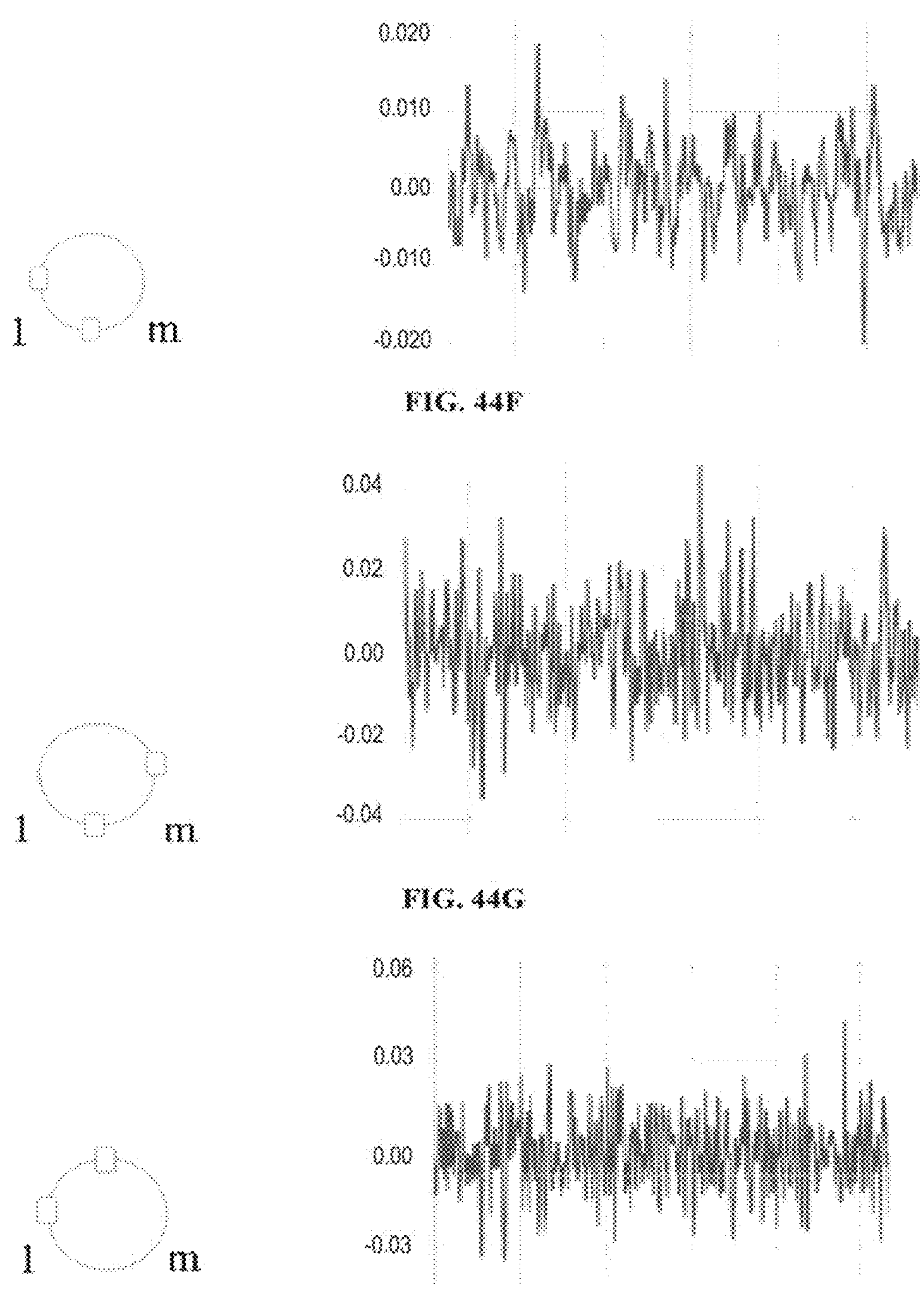
Figures 44I, 44J, 44K:
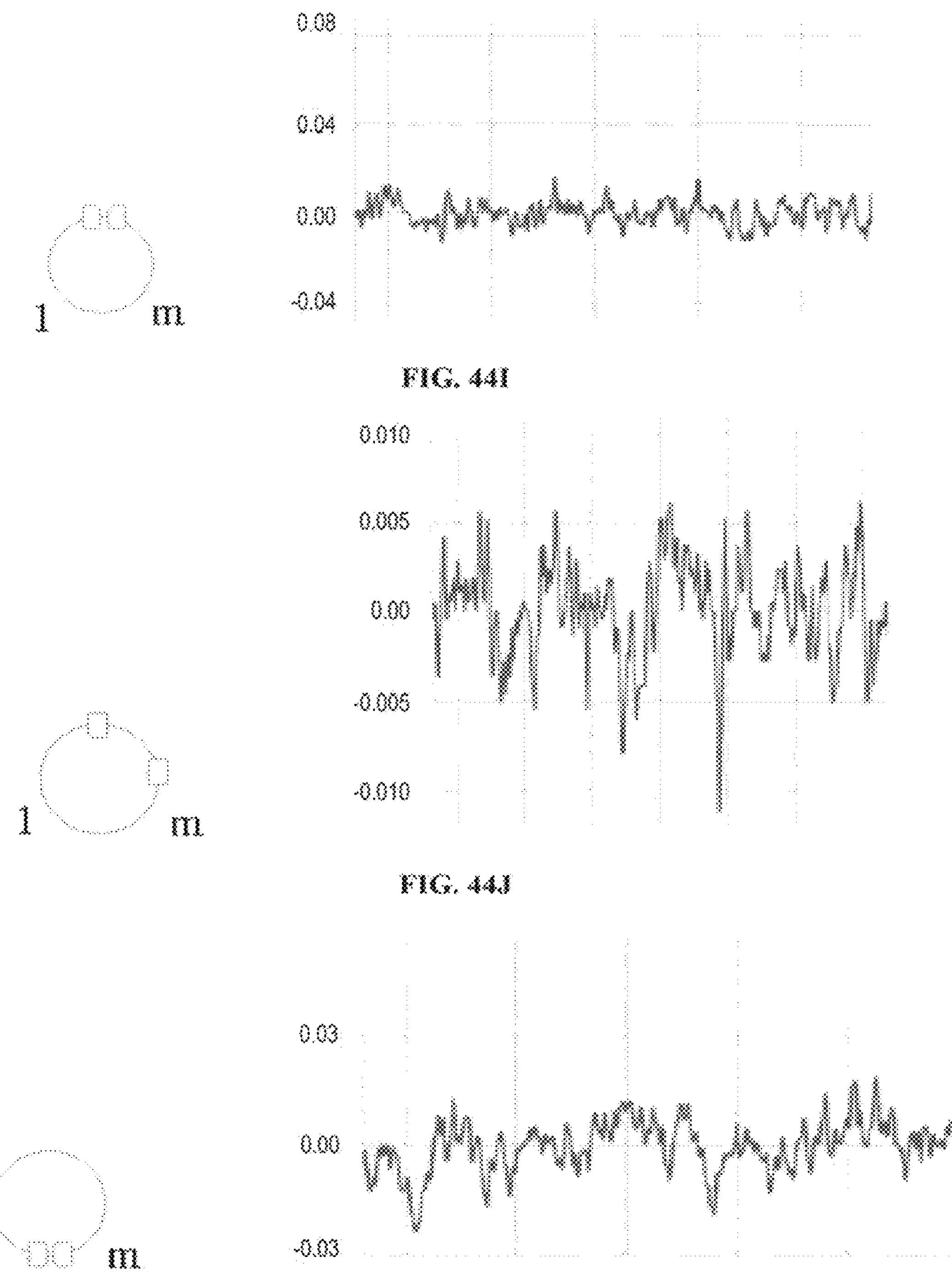

When the device is attached at the upper part of the upper arm as shown in FIG. 43A, the preferred positions of the sensors are those shown in FIGS. 43C, 43F, and 43H.

Fixed Sensor Location Signal Quality Test: The variance in signal quality that persists between patients while the device sensors are fixed at single location was evaluated.

The goal of this test is to determine whether there is a large variance in the signal quality of the device when a single fixed sensor location is chosen and applied to different arm sizes. It is hypothesized that the location of the sensors may be critical to getting ECG data. Due to the variance in the sizes and other characteristics of the users' arms, the optimal sensor location may be difficult to achieve on all users. How large an impact will this issue cause is unknown. If the impact is minor, a fixed sensor distance will likely be chosen due to the much like complex design required.

Test Setup: This test was divided into two use-cases: 1) Maintaining a fixed distance between the two sensors; 2) Maintaining a fixed distance between each sensor and central printed circuit board (PCB) of the device, for example, as shown in FIG. 6.

The ECG recording was conducted for 2 minutes. The baseline test was conducted on the user with the smallest arm (Subject A) measuring only 7 cm between the 2 positions that the sensors detect signals from, the first position being on the medial side of the bicep below the armpit, the second position on the opposing side of the bicep. Additionally, on Subject A, the sensors were placed close to the central P. The device was then placed on users with increasingly larger arm width. These locations along the longitudinal axis of the arm were then fixed with respect to the physiological features of the arm and were not altered for the each of the subjects.

Figure 45A:
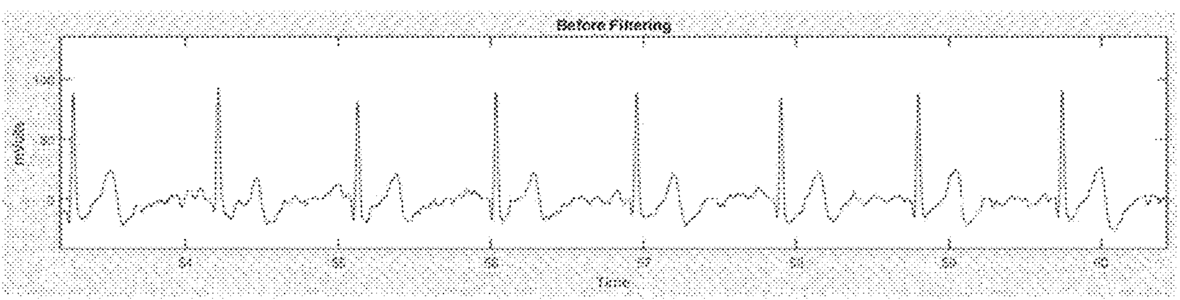
FIGS. 45A-45G show the results of using the device on different arm sizes.
Figure 45B:
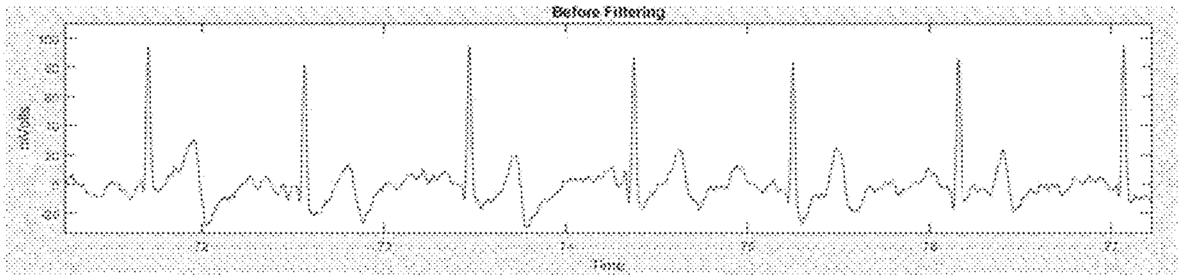
Figure 45C:
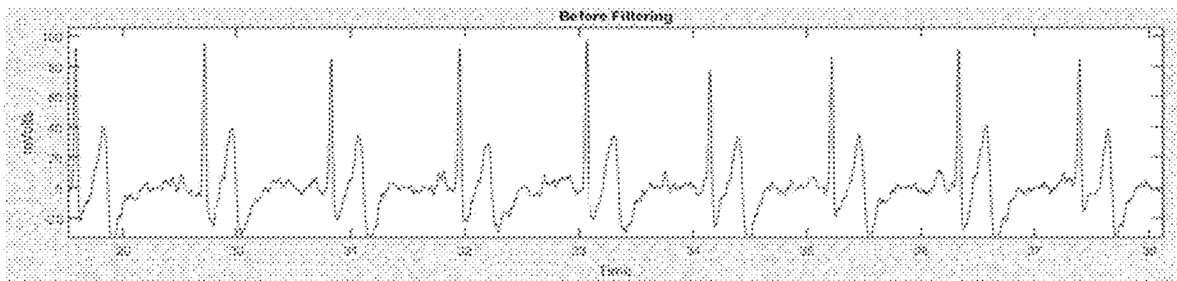
Figure 45D:
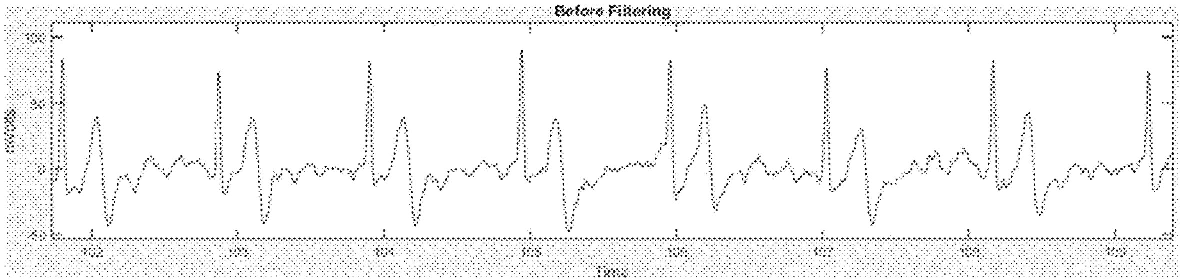
Figure 45E:
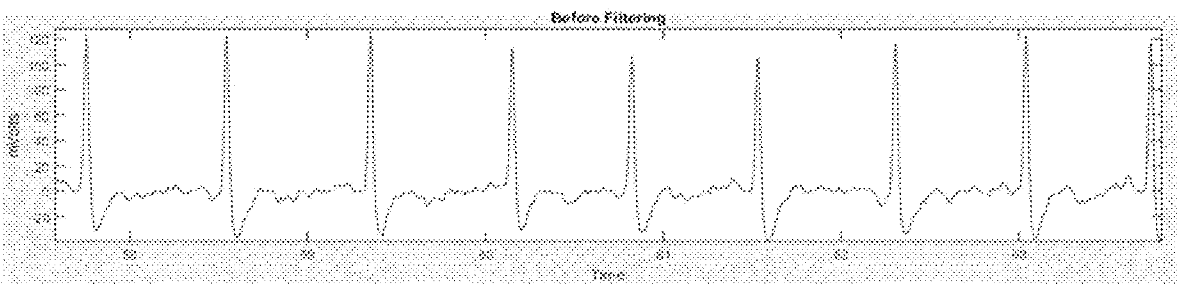
Figure 45F:
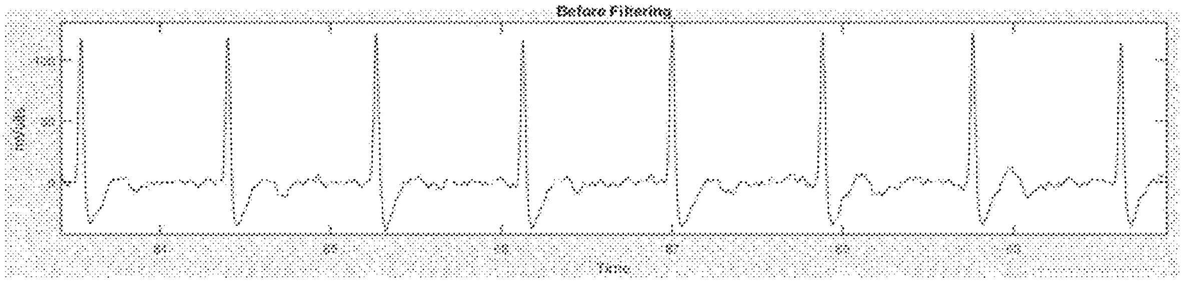
Figure 45G:
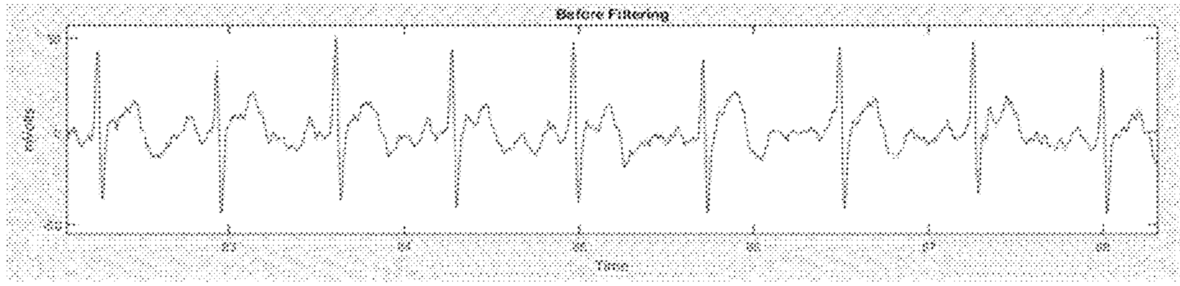

Results: The results from each of the test, and each person are shown in FIGS. 45A-45G. FIGS. 45A and 45B show the results for Subject A, FIGS. 45C and 45D show the results for Subject B, FIGS. 45E and 45F show the results for Subject C, and FIG. 45G show the result for Subject D.

Comparing Shielding Materials: Multiple shielding materials were tested for use in the device system to determine which materials improve the overall signal quality. The material that produced the preferred results is utilized in all devices.

Background: Noise could influence the signals detected by the device due to the very small amplitude of the signals. Thus, it may be advantageous to reduce the noise. One means to reduce noise is to apply noise reducing shields. There exist many materials that may be used as a noise-reducing shield. Five materials were tested: 1) MU Metal (approximately 77% nickel, 16% iron, 5% copper, 2% chromium) EMI-Shielding Nickel Alloy. 2) RF Absorbing Material. 3) Copper Tape. 4) Metal Shield cans. 5) Conductive fabric and Thread.

All the material were tested on in these combinations: 1) Standard—Metal Shield can with RF absorbing material inside. 2) Metal shield can with the MU metal on the inside. 3) Metal shield can with the MU metal on the outside. 4) Metal shield can with all shielding materials packed on the inside. 5) Metal shield can with all shielding materials packed on the inside with MU metal on the outside of the can. 6) Metal shield with all shielding materials packed on the inside with MU metal on the inside of the can.

The testing procedure is as follows. 1) Collect 1 minute of data in standard collection positions. 2) Have someone move a lot with the system attached thereto, to increase fluctuation in EMI for 30 seconds, in which process the sensors do not move and the positions where the signals are collected do not change. 3) Collect 30 second of data in the standard collection position.

Figure 46A:
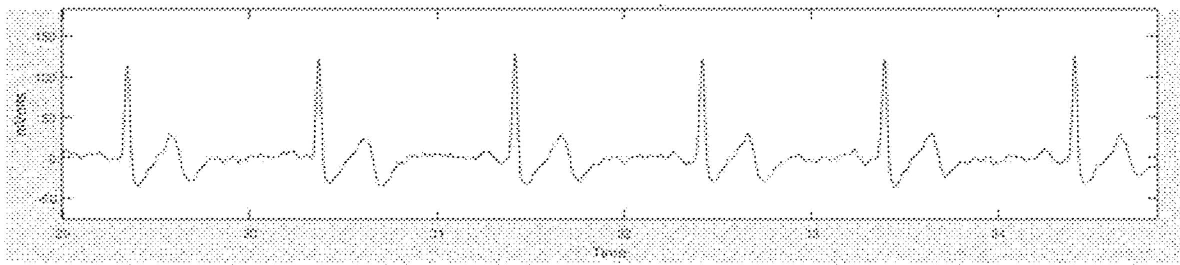
FIGS. 46A-46B show the results when in the standard.
Figure 46B:
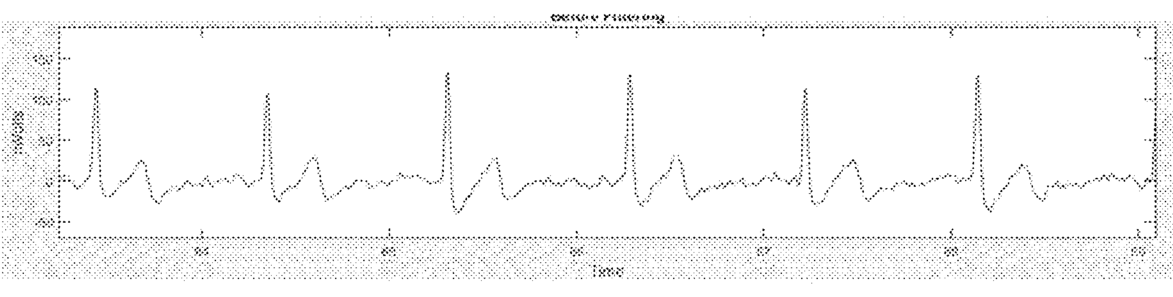
Figure 47A:
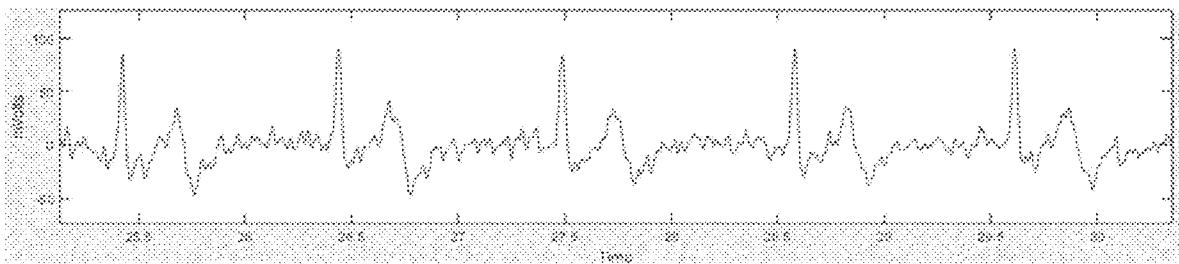
FIGS. 47A-47B show the result when the noise-reducing material is Metal shield can with the MU metal on the outside.
Figure 47B:
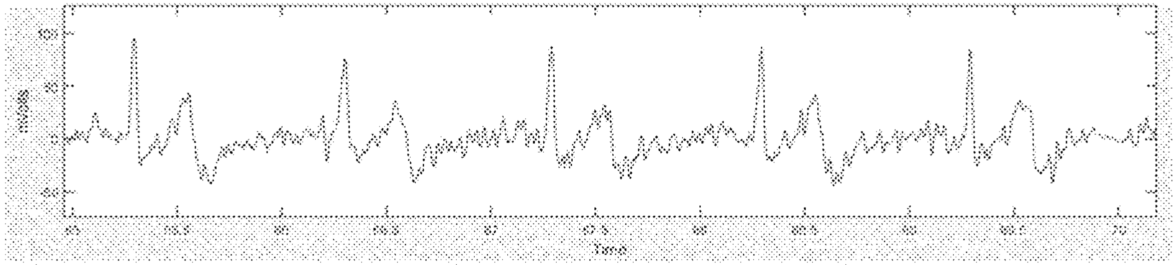
Figure 48A:
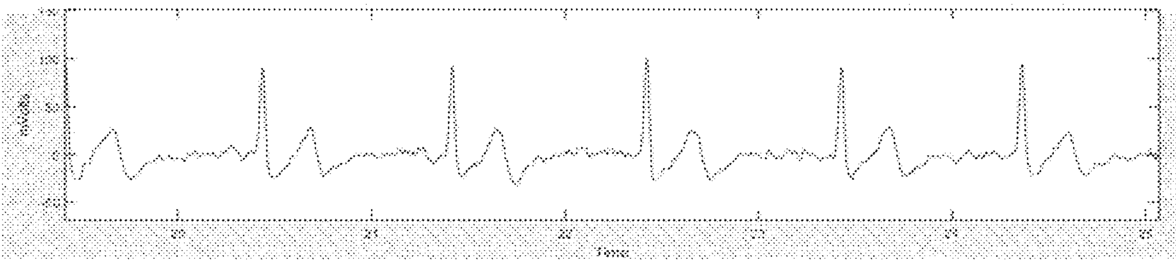
FIGS. 48A-48B show the results when the noise-reducing material is metal shield can with the MU metal on the inside.
Figure 48B:
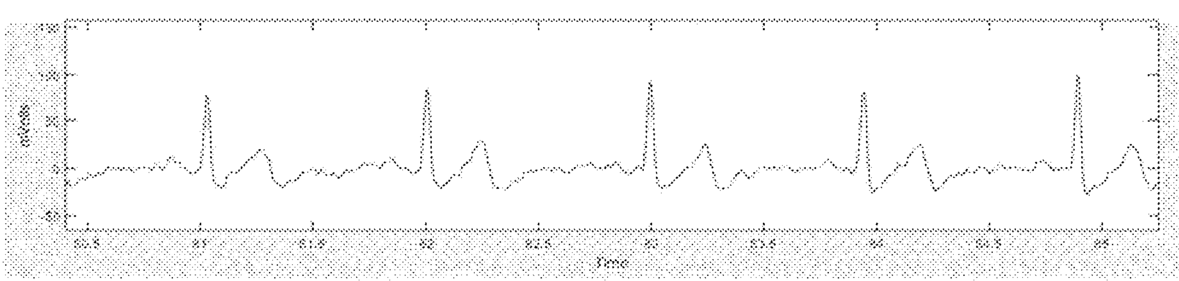
Figure 49A:
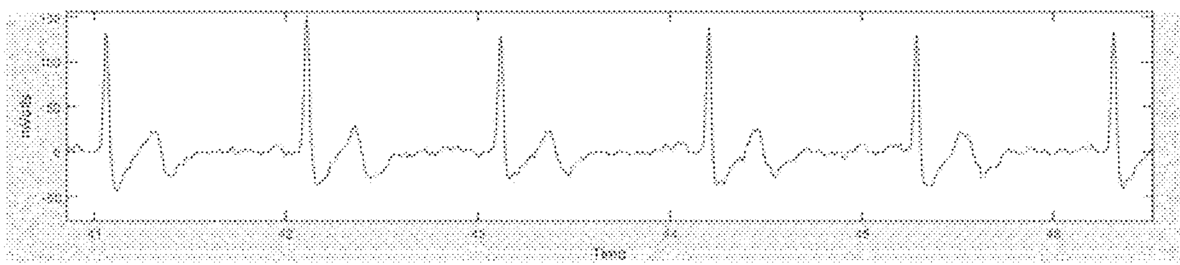
FIGS. 49A-49B show the results when the noise-reducing shield is made of Metal shield can with all shielding materials packed on the inside.
Figure 49B:
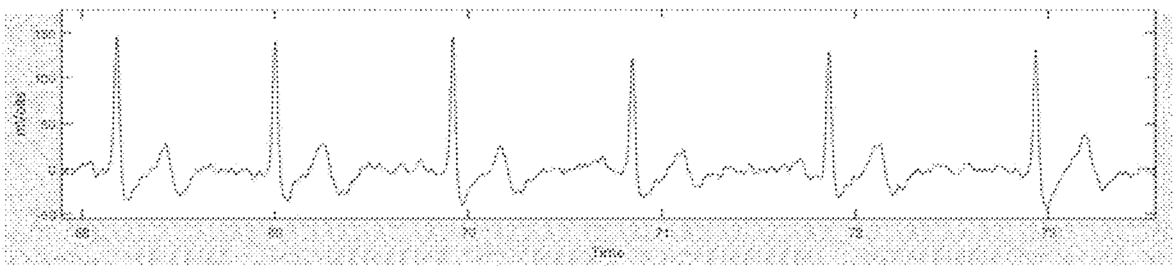
Figure 50A:
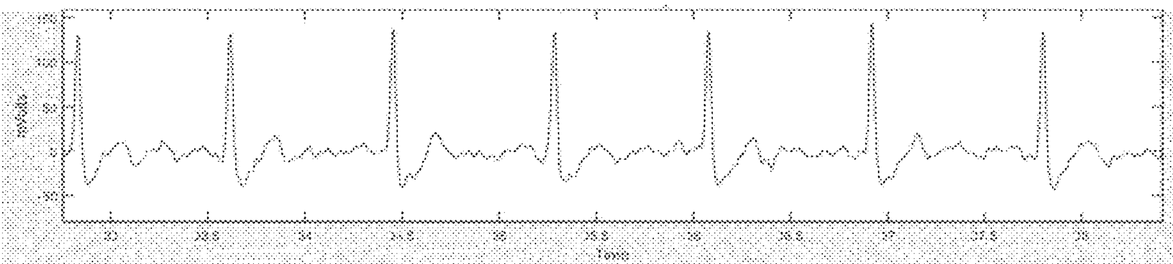
FIGS. 50A-50B show the results when the noise-reducing shield is made of Metal shield can with all shielding materials packed on the inside with MU metal on the outside of the can.
Figures 50B, 51A, 51B:
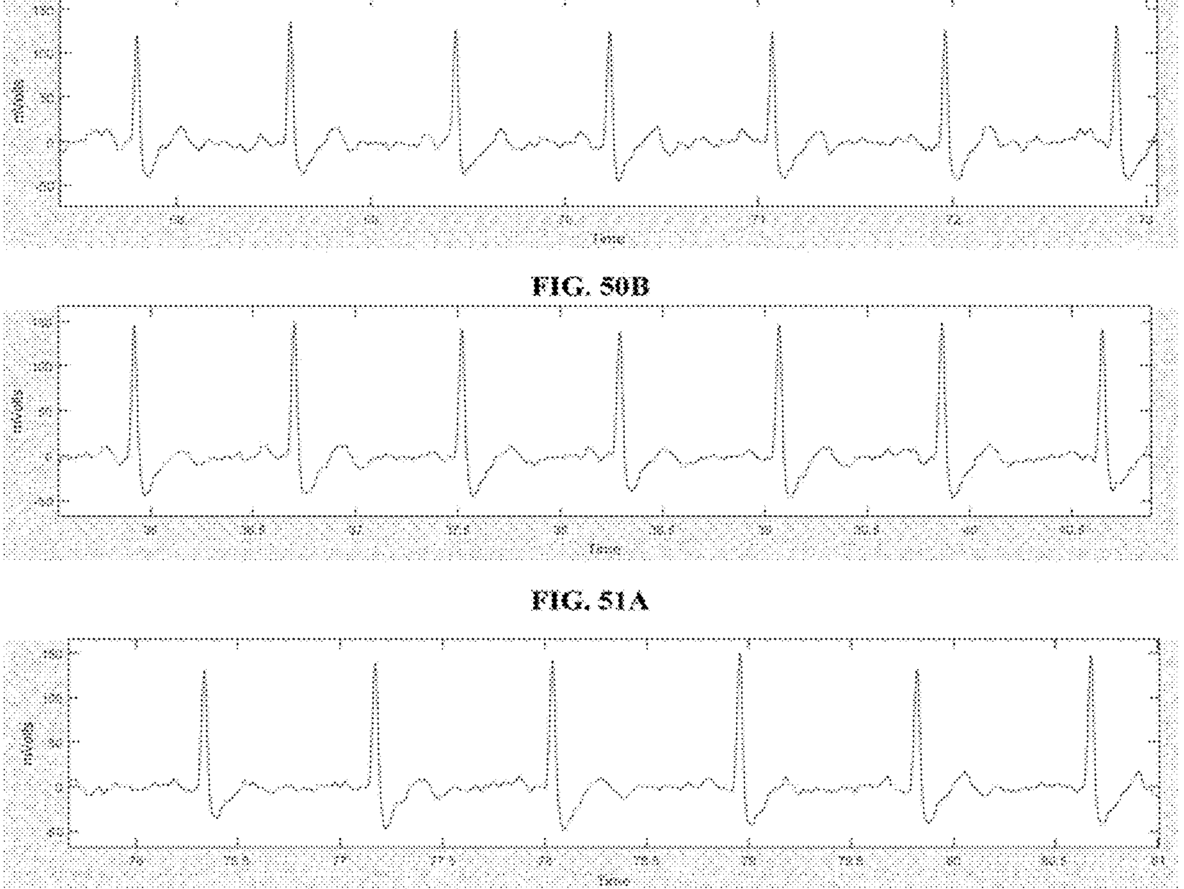
FIGS. 51A-51B show the results when the noise-reducing shield is made of Metal shield with all shielding materials packed on the inside with MU metal on the inside of the can.

Results: The test results are shown in FIGS. 46A-51B. The results are analyzed to see how the noise in the first minute of data (the first images, i.e., FIGS. 46A, 47A, 48A, 49A, 50A, and 51A), and during the increases in fluctuation (the second images, i.e., FIGS. 46B, 47B, 48B, 49B, 50B, and 51B). All results were compared to the standard case that is used in the current system. FIGS. 46A and 46B shows the results for standard (combination 1). FIGS. 47A and 47B show the results when the noise-reducing shield is made of Metal shield can with the MU metal on the outside (combination 3). FIGS. 48A and 48B show the results when the noise-reducing shield is made of metal shield can with the MU metal on the inside (combination 2). FIGS. 49A and 49B show the results when the noise-reducing shield is made of Metal shield can with all shielding materials packed on the inside (combination 4). FIGS. 50A-50B show the results when the noise-reducing shield is made of Metal shield can with all shielding materials packed on the inside and the MU metal on the outside of the can (combination 5). FIGS. 51A-51B show the results when the noise-reducing shield is made of Metal shield with all shielding materials packed on the inside with MU metal on the inside of the can (combination 6).

Observations: It is observed that the MU metal on the outside of the can leads to poor results as shown in FIGS. 47A-47B and 50A-50B (combinations 2 and 5). There is better SNR when using the MU metal on the inside without the presence of the RF absorbing material, as shown in FIGS. 48A-48B (combination 3). The results from the RF absorbing material alone in the metal can (FIGS. 47A-47B), metal can with all materials (FIGS. 49A-49B), and the metal can with MU metal on the inside and all materials inside (FIGS. 51A-51B) look similar. RF absorbing material alone in the metal can has the best SNR for the initial minute of data collection. However, with the increased fluctuation of EMI the results of RF absorbing material alone in the metal can become similar to metal can with all materials and metal can with MU metal on the inside and all materials inside. This suggests that the MU metal on the inside can reduce the impact of the increase EMI noise, yet reducing the signal quality in a standard setting.

Conclusion: Combination 1 (using the RF absorbing material in the metal can) is the chosen material to be used in the system. This is due to the fact it produced the best results for the initial minute of data collection. In addition, it produce the similar result to combinations 4 and 6 when higher EMI was introduced.

Figure 52A:
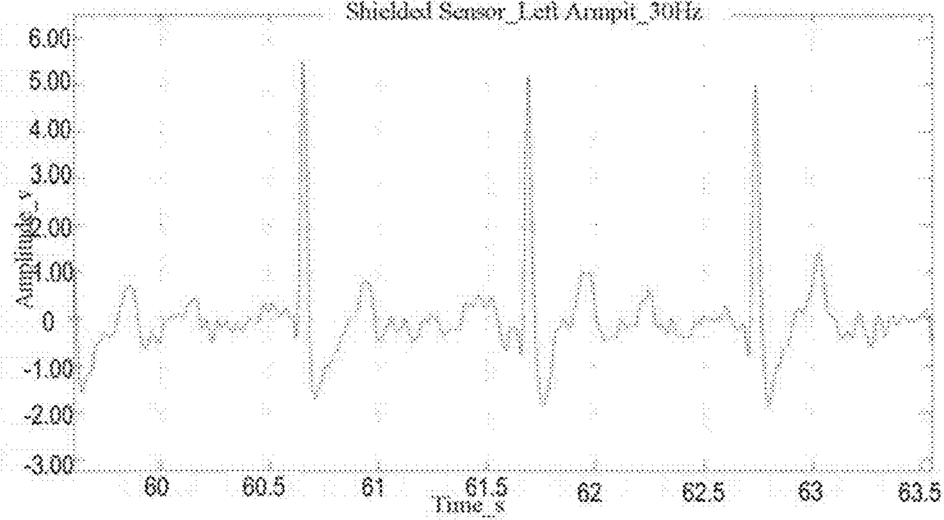
FIG. 52A shows the results using shielded electrodes at the left armpit.
Figure 52B:
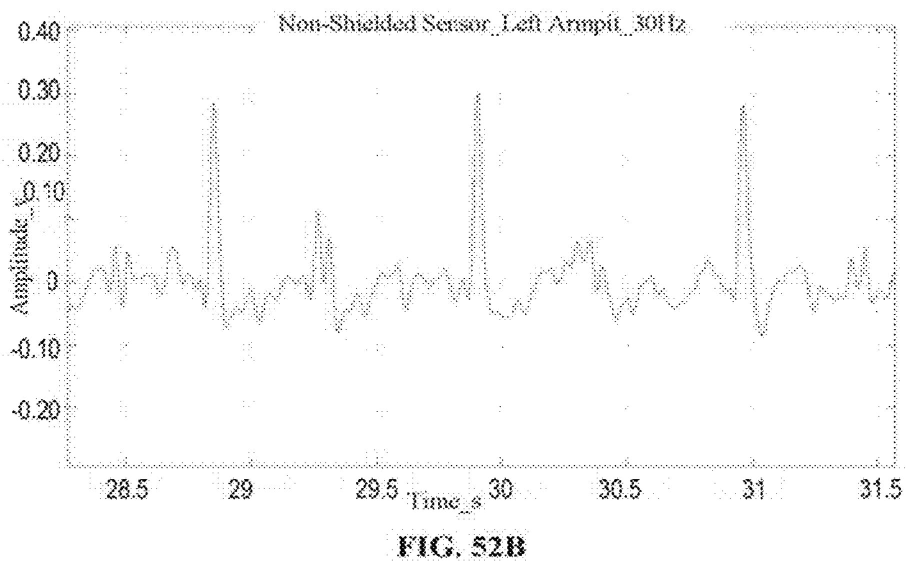
FIG. 52B shows the results using non-shielded electrodes at the left armpit.

With combination 1 (the RF absorbing material and the metal can) there was noticeable change when a larger fluctuations of EMI was created. This change was less noticeable when using the MU-metal on the inside of the metal can. For the amounts of EMI fluctuations in this test, the shield of combination 1 was the preferred option. However if the increase in EMI fluctuation is proportional to the amount increased noise, then combination 1 may become a worse option than combination 4 or 6. In this situation, a larger SNR may occur leading to a less accurate ECG signal Comparisons between shielded electrodes on system to non-Shielded electrodes: Signals were collected from the left armpit of a user using shielded electrodes (FIG. 52A) and exposed electrodes (FIG. 52B). Shielding provided an improvement in both the features of the ECG signal and the amplitude of the signal.

Figure 53:
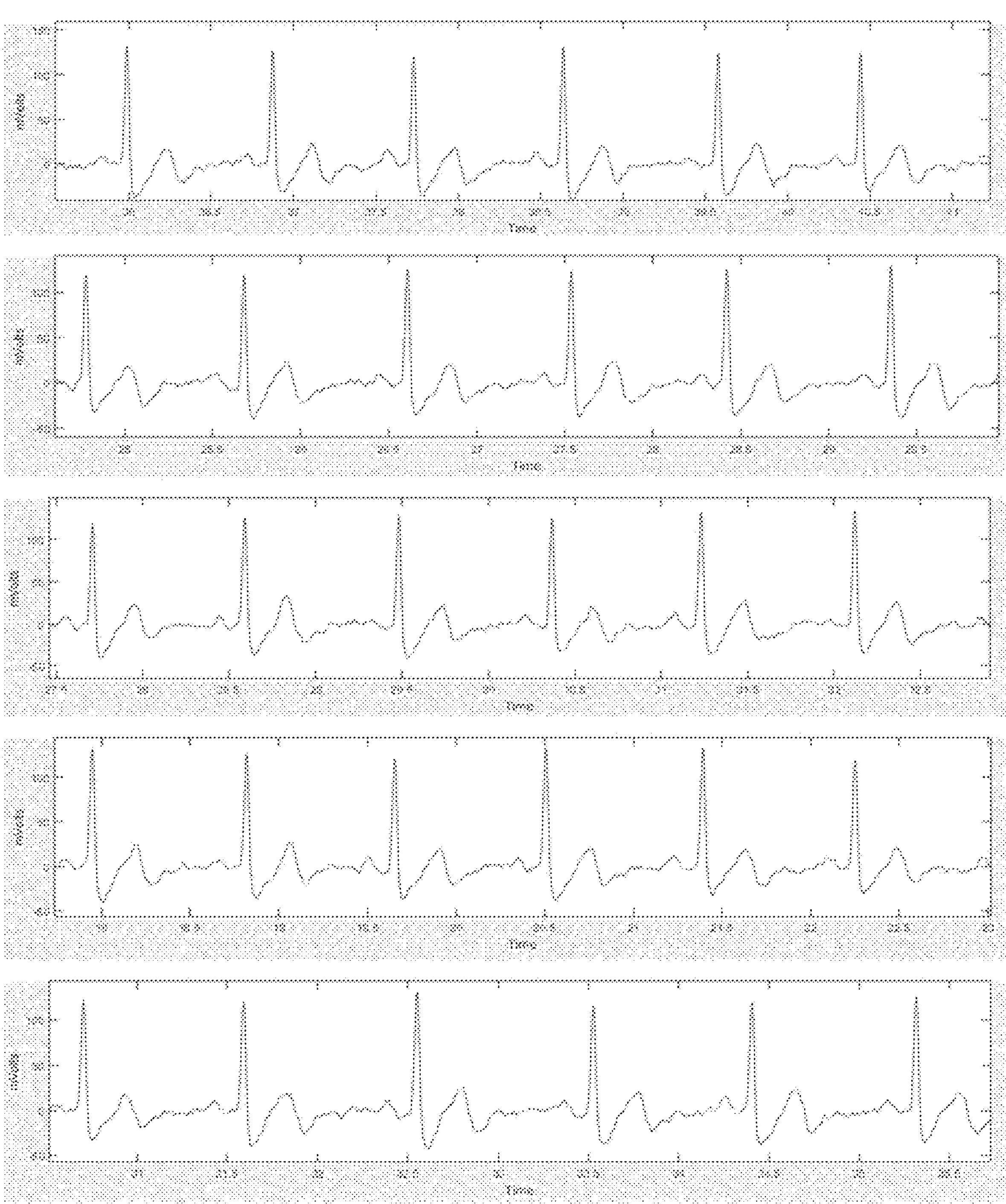
FIG. 53 shows the typical results of the ECG results by one embodiment of the device of this disclosure.

Typical Results Coming from the Wearable band unit: FIG. 53 shows some of the typical results collected using the wearable band unit system. The device was removed and replaced for each test, however the data was gathered from the same user. A clear QRS and T wave was detectable. P wave is detectable for a large portion of the signals. These signals can be used as reference as to the wearable band unit's capabilities.

Results from the electrically coupled capacitive sensor+ Wearable band unit: This section explores the setup of implementing the electrically coupled capacitive sensor into the wearable band unit system and its initial results. Based on these results, a conclusion was made on whether the implementation of the electrically coupled capacitive sensor will become the main sensor for the wearable band unit system.

The Setup: In some embodiments, the device comprises two electrically coupled capacitive sensors, two electrically coupled capacitive sensor electrodes, a differential circuit, device body, and a phone. The sensors were powered from an iteration board providing +−3.1V and GND. The sensor and electrode were then connected. The output of the two sensor were sent to the inputs of a differential OP Amp with a unity gain. The LMV832 was used due to its high EMI reduction and low noise. The output of the Op Amp was soldered to the capacitive Sensor test pin on the wearable band unit board. The signal from the differentiated electrically coupled capacitive sensor proceeds normally through the remainder of the wearable band unit. That is, the signal traveled through a hardware filter, into the ADC and Bluetooth™ module. Then the signal was sent to the phone where software filters are applied and the resulting data is shown on a graph.

Test with this setup was completed on the three areas of interest: the chest, the wrist and the armpit region. The raw data files, filtered data files and screenshot of the data presented on the app were collected.

Figures 54A, 54B, 54C:
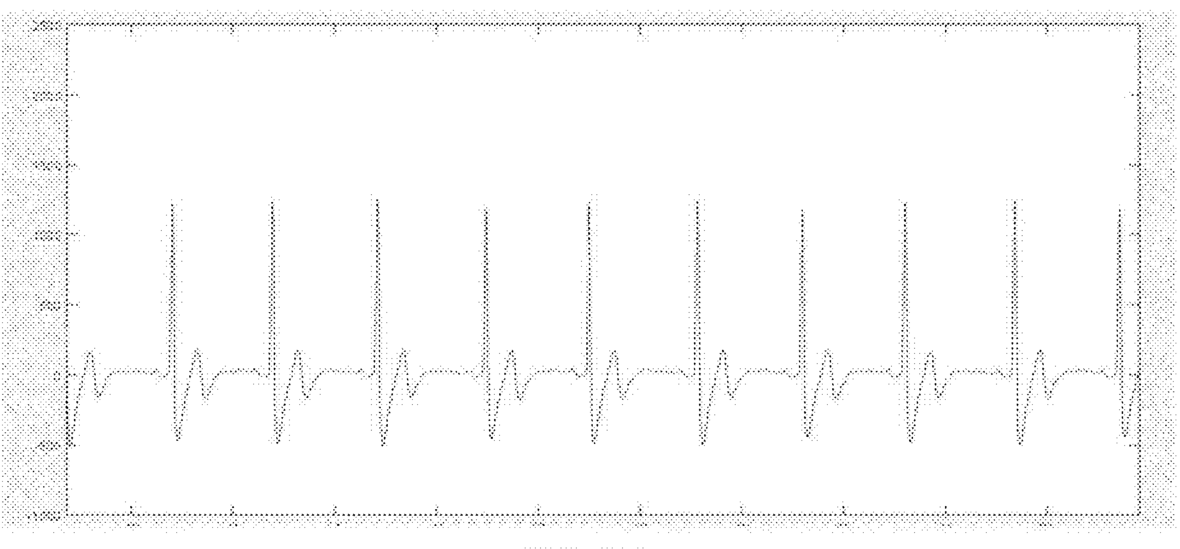
FIGS. 54A-54C show the results from the chest using one embodiment of the device of this disclosure comprising capacitive sensors.

Results: The Chest: Observations: FIGS. 54A-54C show the results of the signals collected at the chest. The signal from the chest are quite promising. There was a clear and consistent ECG with high signal to noise ratio, and both the T and P wave were clearly identified. It is observed that the T wave has a slight dip below the baseline. Without being bound to a theory, it is hypothesized that one potential reason could be the sensor producing oscillation that may be produce a false T wave.

Figure 56A:
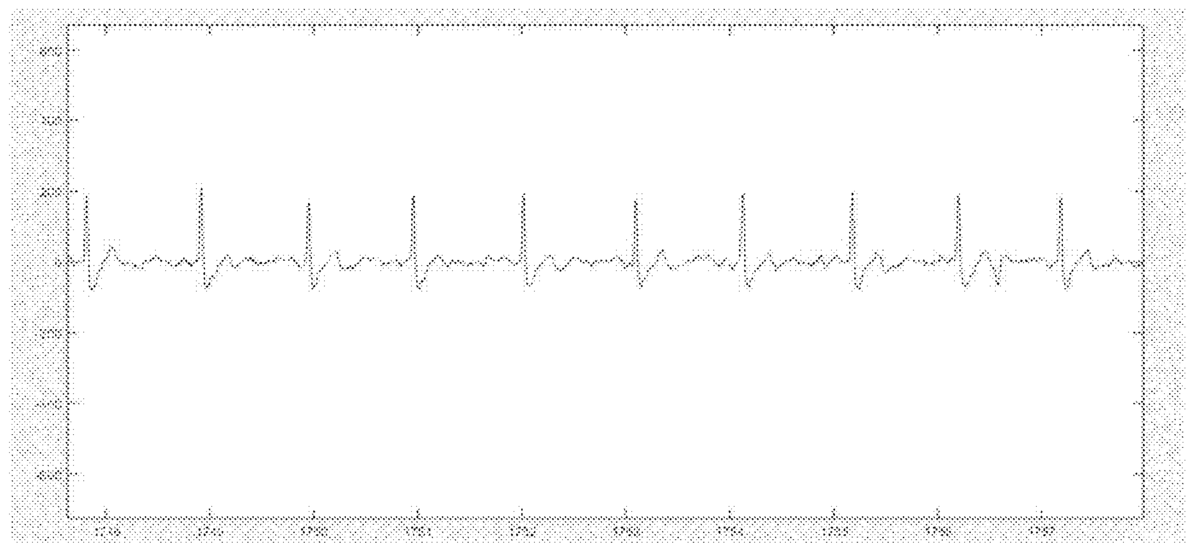
FIGS. 56A-56C show the results from the armpit using one embodiment of the device of this disclosure comprising capacitive sensors.
Figures 56B, 56C:
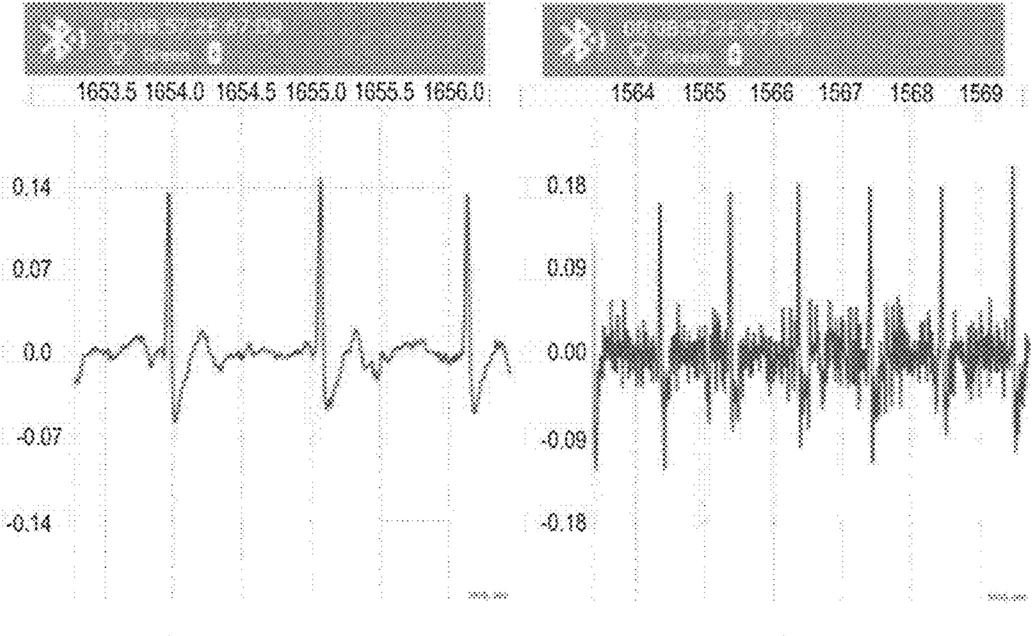

FIGS. 55A-55C show the result of the signals collected at the wrist. FIGS. 56A-56C show the result of the signals collected at the armpit.

Electrically coupled capacitive sensor in Wearable band unit Configuration Testing on Upper Arm: The purpose of testing the electrically coupled capacitive sensors is to determine the areas along the arm that are optimal for obtaining ECG results. Further identifying and narrowing these spots is vital for future testing and sensor placement. This section reports areas of interest, where strong signals were found.

Background: Testing was done on both arms. A coordinate system was put in place to identify the area from which results were obtained, as shown in FIGS. 57A-57B. FIG. 58 shows the method of strapping used to hold the electrodes in place.

Notable Results: FIG. 59 shows the result when the one sensor was placed at A0 and another sensor was placed at A3 in the coordination system shown in FIGS. 57A-57B. FIG. 60 shows the result when one sensor was placed at B0 and another sensor was placed at B1 in the coordination system of FIGS. 57A-B. FIG. 61 shows the result when a sensor was placed at B0 and another sensor was placed at B2 in the coordination system of FIGS. 57A-57B. FIG. 62 shows the result when a sensor was placed at B0 and another sensor was placed at B4 in the coordination system of FIGS. 57A-57B. FIG. 63 show the result when a sensor was placed at C0 and another sensor was placed at C4 in the coordination system of FIGS. 57A-57B.

Conclusions: The preferred results were obtained on the left arm, concentrated around the mid bicep/armpit area.

Wearable band unit Different EMI setting validation: This test was done to see how the power station affects the noise of the signal. There seemed to be no to very little noticeable different in the SNR.

| Test Time | Position |
|---|---|
| 0-60 seconds | Stand with arm in pocket Near power station |
| 60-100 second | Stand with arm crossed Near power station |
| 100-190 second | Sitting with arm crossed Near power station |
| 190-230 second | Walking inside (no data) |
| 230-260 second | Stand with arm in pocket Inside |
| 260-300 seconds | Sitting with arm crossed inside |

With Arms in Pocket: FIG. 64A shows the result when the arms are at the Power Station. FIG. 64B shows the result when the arms are away from the power station.

Figure 65A:
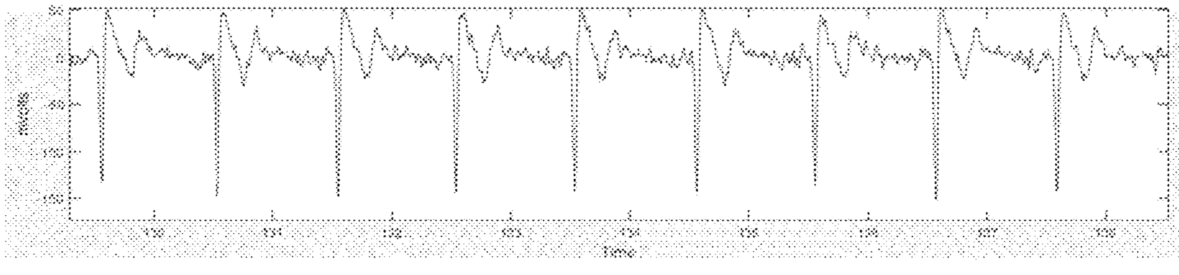
FIG. 65A shows the result when the user is sitting with arms crossed and at the power station.
Figure 65B:
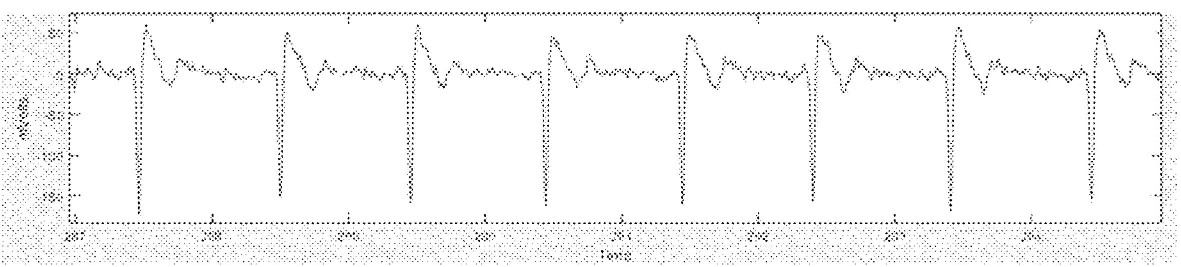
FIG. 65B shows the result when the user is sitting with arms crossed and away from the power station.

Sitting with Arm Crossed: FIG. 65A shows the result when the arms are at the Power Station. FIG. 65B shows the result when the arms are away from the Power Station.

Figure 66:
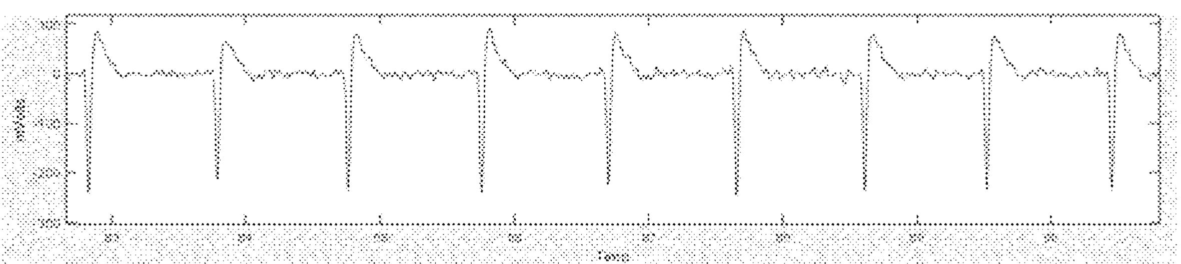
FIG. 66 shows the result when the user's arms are crossed and at the power station.

With Arms Crossed while both arms are close to the power station: FIG. 66 shows the results when the arms are at the Power Station.

Figure 67:
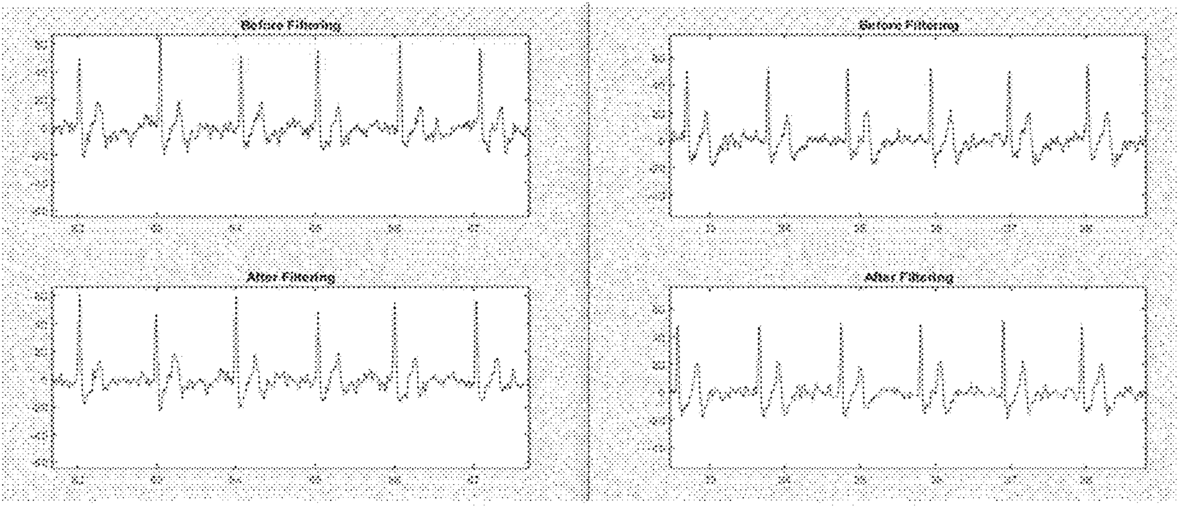
FIG. 67 shows the result when the device is used with and without and RF shield, the left side shows results with the RF shield, while the right side shows results without the RF shield.

Comparing The Wearable band unit with and without an RF shield: Tests were conducted to compare the results of the wearable band unit with and without an RF shield (FIG. 67) and no real noticeable difference.

Figure 68:
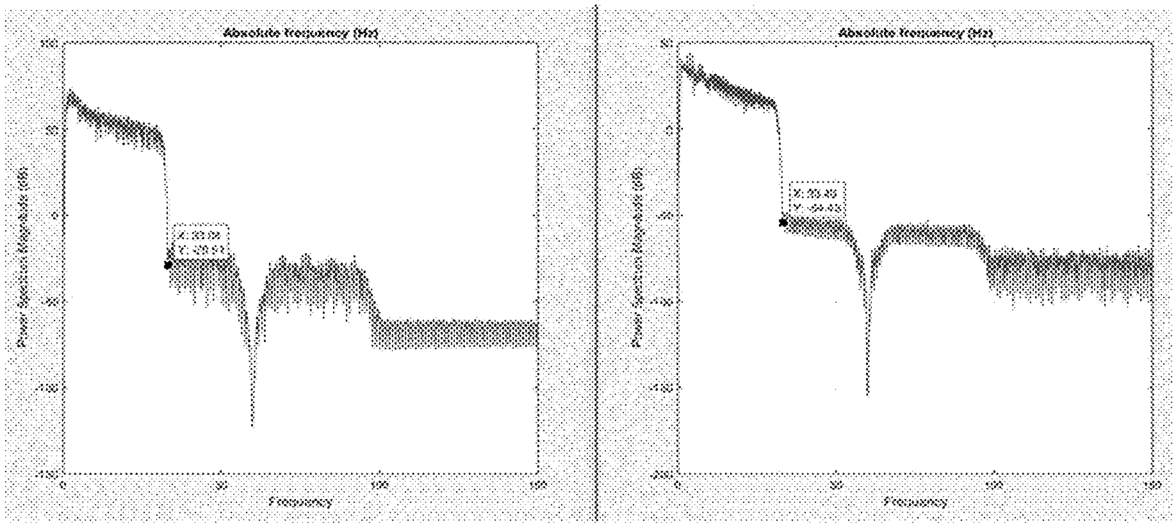
FIG. 68 shows the enlarged view of the comparison of the results with and without the RF shield, with the results the left side shows results with the RF shield, while the right side shows results without the RF shield.
Figure 71A:
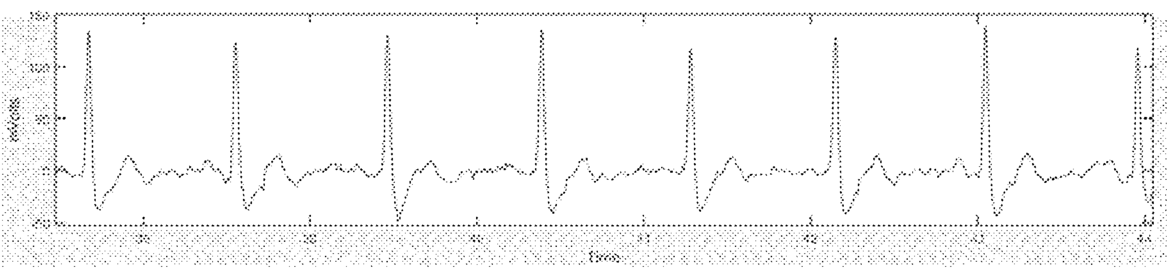
FIGS. 71A-71C show the result by one embodiment of the device of this disclosure.
Figure 71B:
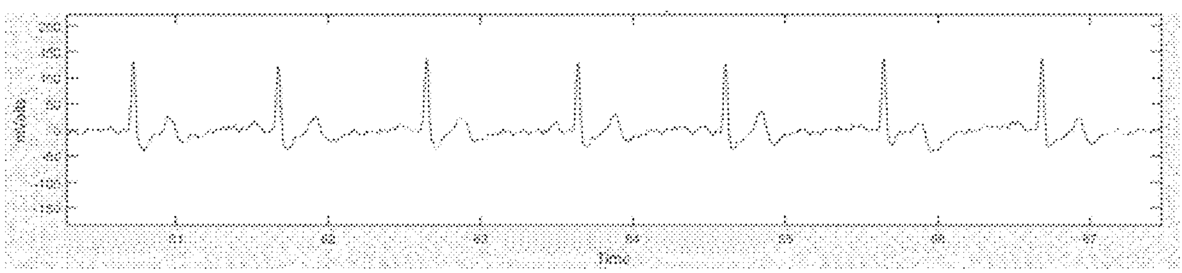
Figure 71C:
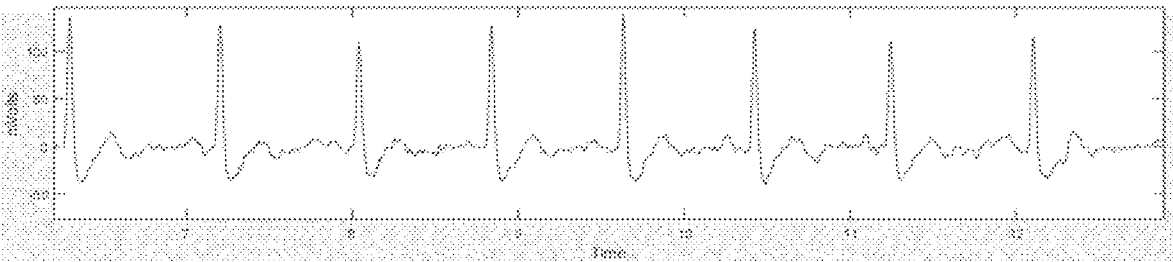
Figure 72:
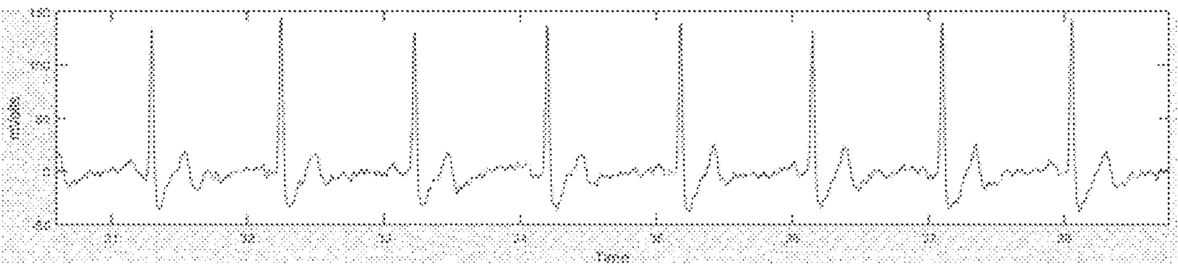
FIG. 72 shows the result by another embodiment of the device of this disclosure.

FIG. 68 shows a change of rough 75 dB for both (the left is with and the right is without RF shield). There seems to be less bounce when there was an RF shield.

FIG. 69 shows another comparison between the results with and without the RF shield. Three distinct peaks are found at roughly areas that an ECG signal is expected.

Based on the Power Spectrum density graph the RF shield improved the signal, but the Time series of the ECG does not appear to add any feature.

Signals obtained while in different states of motion: FIGS. 70A and 70B show a comparison between the data from a conventional wet electrode based system obtained from classical Lead 1 locations (FIG. 70A) and the data collected using the device of this disclosure (FIG. 70B). The user was in normal walking motion. The former has no true distinct features, while the latter has both detectable signals and features.

Device iteration comparisons: Multiple embodiments of the device of this disclosure were tested and the results are shown in FIGS. 71A-71C and 72A. The data was collected in the standard position, with a mock up enclosure (an elastic strap and two electrode housing boxes).

Figure 73:
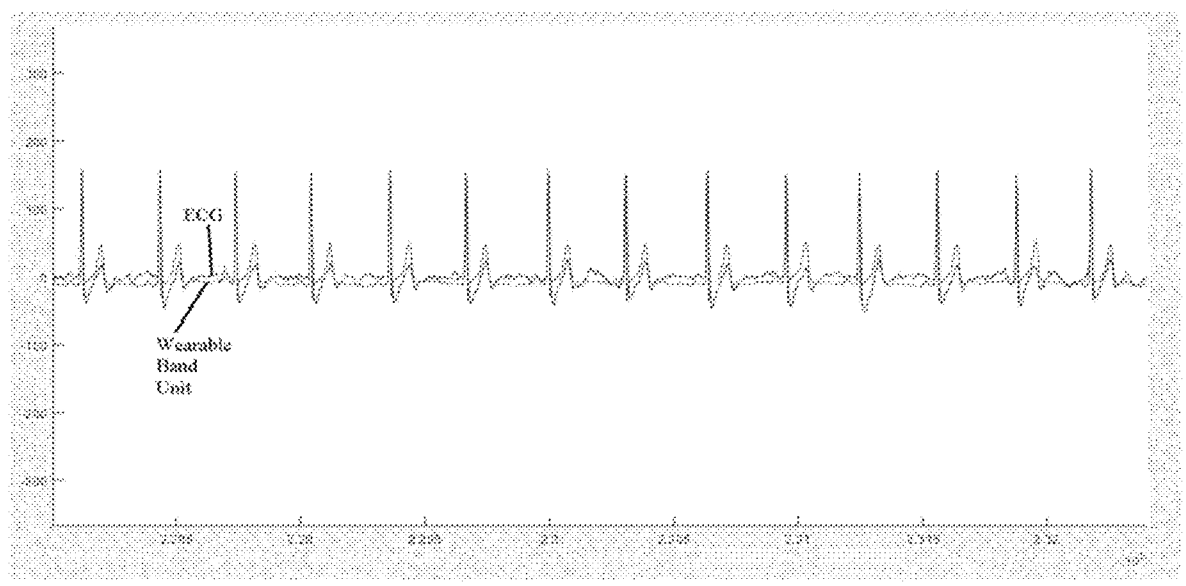
FIG. 73 shows the comparison of the data of the device of this disclosure and the classical ECG.

Comparison data between Wearable band unit and Classical ECG data: The data from the wearable band unit and the Classical ECG monitor were compared as shown in FIG. 73. The first signal is Classical ECG and the second signal is wearable band unit. The ECG data collected by the wearable band unit is very comparable and has all the features compared to a classical ECG data.

Figure 74A:
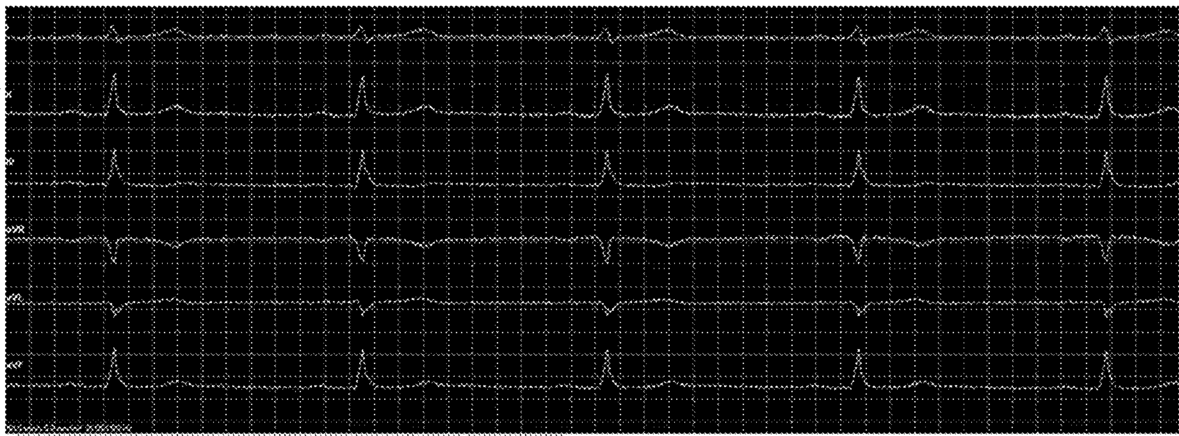
FIG. 74A shows the ECG data from a 13 lead ECG monitor.
Figure 74B:
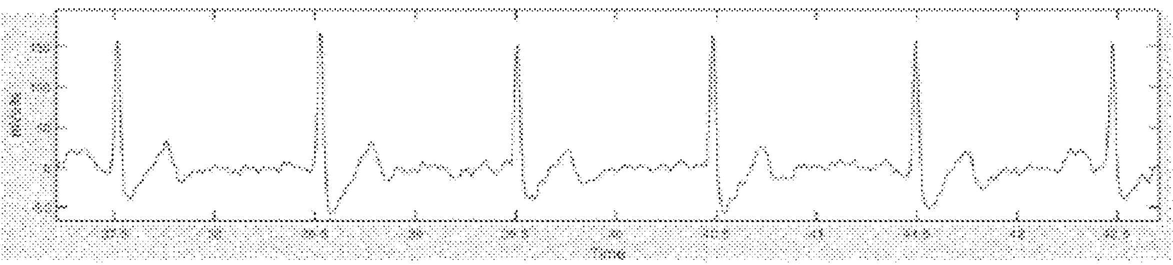
FIG. 74B shows the ECG data from the device of this disclosure.

Comparison to Holter Monitor: In this validation test, the data for the wearable band unit device (FIG. 74B) is compared against data collected a 13 lead ECG monitor (FIG. 74A).

Re-programmable/Automatic Gain Control System: The device collects very small signals, around the range of the resolution of the ADC. In this aspect, digitization of the signal is potentially noticeable, resulting in poor signal quality. In designing the device, an easy control of the board gain may be a desirable feature to alleviate this problem will little detrimental effect. Secondly, it is understood that amplifying the signal as early as possible reduces the influence of any noise collected afterwards. Thus, it may be preferable to amplify the signal on the hardware as early as possible after collection. Having control on this process through the app would be convenient. Therefore, an automatic gain control circuit may be implemented into the hardware in which the microcontroller can control. The system may be able to achieve different gain setting jumps. This may be controlled through the app in the setting of each device. The device is placed on the arm where a strong ideal signal is achieved. The arm is rested on a table to achieve better data. The gain setting is increased in step.

Figure 75:
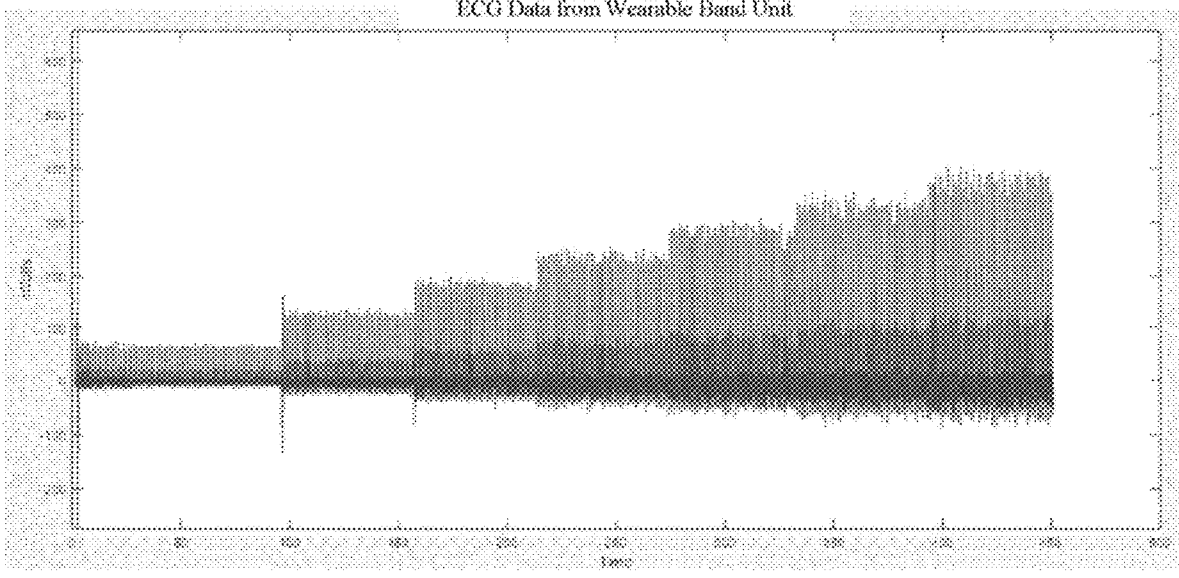
FIG. 75 shows the enlarged view of amplified results.

FIG. 75 shows the blown up view of the complete dataset. It is noticeable that the gain getting larger every minute of data.

In example embodiments, as appropriate, each illustrated block or module may represent software, hardware, or a combination of hardware and software. Further, some of the blocks or modules may be combined in other example embodiments, and more or less blocks or modules may be present in other example embodiments. Furthermore, some of the blocks or modules may be separated into a number of sub-blocks or sub-modules in other embodiments.

While some of the present embodiments are described in terms of methods, a person of ordinary skill in the art will understand that present embodiments are also directed to various apparatus such as a server apparatus including components for performing at least some of the aspects and features of the described methods, be it by way of hardware components, software or any combination of the two, or in any other manner. Moreover, an article of manufacture for use with the apparatus, such as a pre-recorded storage device or other similar non-transitory computer readable medium including program instructions recorded thereon, or a computer data signal carrying computer readable program instructions may direct an apparatus to facilitate the practice of the described methods. It is understood that such apparatus, articles of manufacture, and computer data signals also come within the scope of the present example embodiments.

While some of the above examples have been described as occurring in a particular order, it will be appreciated to persons skilled in the art that some of the messages or steps or processes may be performed in a different order provided that the result of the changed order of any given step will not prevent or impair the occurrence of subsequent steps. Furthermore, some of the messages or steps described above may be removed or combined in other embodiments, and some of the messages or steps described above may be separated into a number of sub-messages or sub-steps in other embodiments. Even further, some or all of the steps of the conversations may be repeated, as necessary. Elements described as methods or steps similarly apply to systems or subcomponents, and vice-versa.

In example embodiments, the one or more controllers can be implemented by or executed by, for example, one or more of the following systems: Personal Computer (PC), Programmable Logic Controller (PLC), Microprocessor, Internet, Cloud Computing, Mainframe (local or remote), mobile phone or mobile communication device.

The term "computer readable medium" as used herein includes any medium which can store instructions, program steps, or the like, for use by or execution by a computer or other computing device including, but not limited to: magnetic media, such as a diskette, a disk drive, a magnetic drum, a magneto-optical disk, a magnetic tape, a magnetic core memory, or the like; electronic storage, such as a random access memory (RAM) of any type including static RAM, dynamic RAM, synchronous dynamic RAM (SDRAM), a read-only memory (ROM), a programmable-read-only memory of any type including PROM, EPROM, EEPROM, FLASH, EAROM, a so-called "solid state disk", other electronic storage of any type including a charge-coupled device (CCD), or magnetic bubble memory, a portable electronic data-carrying card of any type including COMPACT FLASH, SECURE DIGITAL (SD-CARD), MEMORY STICK, and the like; and optical media such as a Compact Disc (CD), Digital Versatile Disc (DVD) or BLU-RAY (RTM) Disc.

Variations may be made to some example embodiments, which may include combinations and sub-combinations of any of the above. The various embodiments presented above are merely examples and are in no way meant to limit the scope of this disclosure. Variations of the innovations described herein will be apparent to persons of ordinary skill in the art having the benefit of the present disclosure, such variations being within the intended scope of the present disclosure. In particular, features from one or more of the above-described embodiments may be selected to create alternative embodiments comprised of a sub-combination of features which may not be explicitly described above. In addition, features from one or more of the above-described embodiments may be selected and combined to create alternative embodiments comprised of a combination of features which may not be explicitly described above. Features suitable for such combinations and sub-combinations would be readily apparent to persons skilled in the art upon review of the present disclosure as a whole. The subject matter described herein intends to cover and embrace all suitable changes in technology.

Certain adaptations and modifications of the described embodiments can be made. Therefore, the above discussed embodiments are considered to be illustrative and not restrictive.

What is claimed is:

1. An electrocardiogram (ECG) system for detecting ECG signals from a user, comprising:

at least two contacts for disposition on only one peripheral of the user which is a left arm;

at least two sensors for detecting electrical signals from the at least two contacts when disposed on the only one peripheral of the user;

at least two shielded electrodes;

a wearable band on which at least two of the at least two sensors and at least two of the at least two shielded electrodes are disposed, the wearable band being wearable on the one peripheral of the user, wherein the contacts are configured to be positioned on a same axial length along the one peripheral of the user, are distally offset from one another, and have different radial positions on the same axial length, wherein the same axial length is from mid biceps to an armpit of the left arm of the user, and wherein the at least two shielded electrodes are distally offset from each of the contacts and each other of the shielded electrodes;

a board disposed on the wearable band for receiving the electrical signals;

a hardware filter including a low pass hardware filter and shielding disposed on the wearable band for reducing noise from the electrical signals detected by the at least two sensors; and at least one controller for determining a differential signal between a first electrical signal detected by a first sensor of the at least two sensors and a second signal detected by a second sensor of the at least two sensors, the first sensor being different than the second sensor, and for constructing an ECG signal from the differential signal, wherein no sensors are collecting the electrical signals from any other parts of the user for the constructing of the ECG signal.

2. The ECG system of claim 1, wherein each of the at least two sensors comprises a dry capacitive electrode sensor.

3. The ECG system of claim 1, wherein each of the at least two sensors comprises an electrically coupled capacitive sensor.

4. The ECG system of claim 1, wherein the at least one controller includes a differential amplifier for the determining of the differential signal.

5. The ECG system of claim 1, further comprising a wireless communication module for transmitting information including the electrical signals.

6. The ECG system of claim 5, wherein the at least one controller is configured to wirelessly receive the information and perform the constructing of the ECG signal from the information.

7. The ECG system of claim 6, wherein the at least one controller comprises a software application for the constructing of the ECG signal from the information.

8. The ECG system of claim 1, further comprising an amplifier that is disposed in the wearable band.

9. The ECG system of claim 1, further comprising one or more sensors that are disposed in the wearable band for determining pulse oximetry.

10. The ECG system of claim 1, wherein the radial positions are radially opposite to each other with respect to the peripheral of the user.

11. The ECG system of claim 1, wherein the radial positions are about 90° to each other on the different radial positions of the peripheral of the user.

12. The ECG system of claim 1, further comprising a re-programmable gain control system interposed between the at least two sensors and the at least one controller.

13. The ECG system of claim 1, wherein the at least two sensors are in an open circuit configuration with respect to remaining parts of the user other than the only one peripheral.

14. The ECG system of claim 1, wherein the board comprises a plurality of separate ground planes including a signal ground, a digital ground, and an analog ground, and wherein no overlap is allowed between the different ground planes.

15. A method for electrocardiogram (ECG) monitoring of a user, comprising:

providing, on only one peripheral of the user which is a left arm, at least two contacts, at least two sensors for detecting electrical signals from the only one peripheral of the user, and at least two shielded electrodes;

positioning, on the one peripheral of the user, a wearable band on which at least two of the at least two sensors and at least two of the at least two shielded electrodes are disposed, the wearable band being wearable on the one peripheral of the user, wherein the contacts are configured to be positioned on a same axial length along the one peripheral of the user, are distally offset from one another, and have different radial positions on the same axial length, wherein the same axial length is from mid biceps to an armpit of the left arm of the user, and wherein the at least two shielded electrodes are distally offset from each of the contacts and each other of the shielded electrodes;

receiving, with a board disposed on the wearable band, the electrical signals;

detecting, with the at least two sensors, the electrical signals;

applying a hardware filter including a low pass hardware filter and shielding for reducing noise from the electrical signals detected by the at least two sensors;

determining a differential signal between a first electrical signal detected by a first sensor of the at least two sensors and a second signal detected by a second sensor of the at least two sensors, the first sensor being different than the second sensor; and constructing, using at least one controller, an ECG signal from the differential signal, wherein no sensors are detecting the electrical signals from any other parts of the user for the constructing of the ECG signal.

16. The method of claim 15, wherein the at least two sensors are in an open circuit configuration with respect to parts of the user other than the only one peripheral.

* * * * *